United States Patent [19]

Izumi et al.

[11] Patent Number: 5,869,506

[45] Date of Patent: Feb. 9, 1999

[54] FLUOROPROPENE COMPOUND, AN INSECTICIDE CONTAINING THE SAME AND AN INTERMEDIATE FOR PRODUCTION THEREOF

[75] Inventors: Keiichi Izumi, Osaka; Hiroshi Ikegami; Masaya Suzuki, both of Hyogo; Noriyasu Sakamoto, Osaka; Hirotaka Takano, Hyogo, all of Japan

[73] Assignee: Sumitomo Chemical Company, Limited, Osaka, Japan

[21] Appl. No.: 790,665

[22] Filed: Jan. 30, 1997

[30] Foreign Application Priority Data

Jan. 31, 1996 [JP] Japan ..................... 8-015224

[51] Int. Cl.$^6$ ................. A01N 43/40; A01N 37/10; A01N 31/00; C07D 215/00

[52] U.S. Cl. ................. 514/345; 514/532; 514/713; 514/720; 546/152; 546/153; 546/159; 546/160; 546/168; 546/290; 546/293; 546/301; 546/302; 546/303; 546/304; 546/326; 546/329; 546/339; 546/346

[58] Field of Search ................. 568/39, 45, 50, 568/630, 649; 564/440, 442; 560/8, 9, 100, 103, 110, 111; 546/152, 153, 159, 160, 168, 290, 293, 301, 302, 303, 304, 326, 329, 339, 346

[56] References Cited

U.S. PATENT DOCUMENTS

| | | | |
|---|---|---|---|
| 4,048,235 | 9/1977 | Karrer | 260/612 |
| 4,061,683 | 12/1977 | Karrer | 260/613 |
| 4,123,556 | 10/1978 | Karrer . | |
| 4,496,440 | 1/1985 | Campbell et al. | 204/78 |
| 4,714,706 | 12/1987 | Kisida et al. . | |
| 4,847,259 | 7/1989 | Kisida et al. . | |
| 4,914,116 | 4/1990 | Kisida et al. . | |
| 5,389,651 | 2/1995 | Henrick . | |

FOREIGN PATENT DOCUMENTS

| | | |
|---|---|---|
| A-227 369 | 7/1987 | European Pat. Off. . |
| A-55-120565 | 9/1980 | Japan . |
| A-56-29504 | 3/1981 | Japan . |
| A-1 420 171 | 1/1976 | United Kingdom . |
| A-1 424 211 | 2/1976 | United Kingdom . |
| A-1 578 412 | 11/1980 | United Kingdom . |
| WO 96/11909 | 4/1996 | WIPO . |
| WO 96/15093 | 5/1996 | WIPO . |
| WO 96/33160 | 10/1996 | WIPO . |

*Primary Examiner*—Alan Siegel
*Attorney, Agent, or Firm*—Pillsbury Madison & Sutro LLP

[57] ABSTRACT

The present invention provides a fluoropropene compound represented by Formula I:

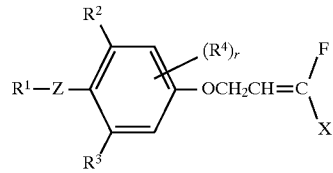

wherein $R^1$ represents a $C_1$–$C_{10}$ alkyl group or other groups, Z represents an oxygen atom or other groups, $R^2$, $R^3$, and $R^4$ each independently represent a $C_1$–$C_3$ alkyl group or other groups, r represents an integer of 0 to 2, and X represents a halogen atom or other groups.

16 Claims, No Drawings

FLUOROPROPENE COMPOUND, AN INSECTICIDE CONTAINING THE SAME AND AN INTERMEDIATE FOR PRODUCTION THEREOF

FIELD OF INVENTION

The present invention relates to a fluoropropene compound, an insecticide containing the same and an intermediate for production thereof

DESCRIPTION OF RELATED ART 1-(3,3-Dichloropropenyloxy)-4-benzyloxybenzene has been known as an insecticidal compound in Japanese Patent Kokai Laid-open Publication No. 49-1526/1974, however, the isecticidal activity of the compound was not always satisfactory. Hence a further compound has been desired.

SUMMARY OF INVENTION

That is, the present invention provides a fluoropropene compound (hereinafter referred to as the "present compound") represented by Formula I:

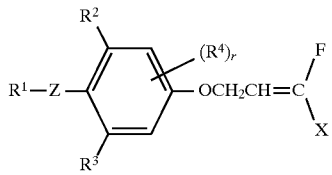

wherein $R^1$ represents, a $C_1$–$C_{10}$ alkyl group, a $C_1$–$C_5$ haloalkyl group, a $C_2$–$C_{10}$ alkenyl group, a $C_2$–$C_6$ haloalkenyl group, a $C_3$–$C_9$ alkynyl group, a $C_3$–$C_5$ haloalkynyl group, a $C_2$–$C_7$ alkoxyalkyl group or a $C_2$–$C_7$ alkylthioalkyl group, a $C_3$–$C_6$ cycloalkyl group which may be substituted with a $C_1$–$C_4$ alkyl group, a $C_1$–$C_3$ alkoxy group or a $C_1$–$C_3$ haloalkoxy group, a $C_4$–$C_9$ cycloalkylalkyl group which may be substituted with a $C_1$–$C_4$ alkyl group;

a $C_5$–$C_6$ cycloalkenyl group which may be substituted with a $C_1$–$C_4$ alkyl group;

a $C_6$–$C_8$ cycloalkenylalkyl group which may be substituted with a $C_1$–$C_4$ alkyl group; or $Q_1$, $Q_2$, $Q_3$, $Q_4$, $Q_5$, $Q_6$, $Q_7$, $Q_8$ or $Q_9$ of Formula II:

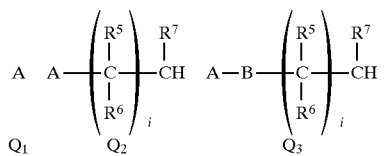

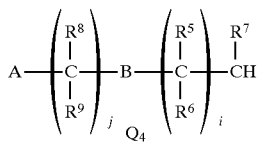

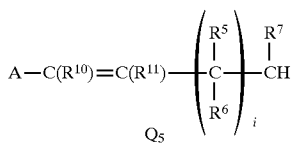

-continued

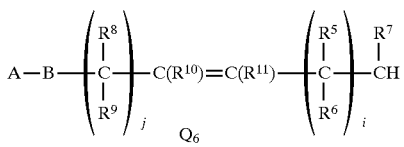

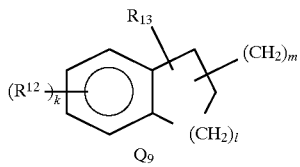

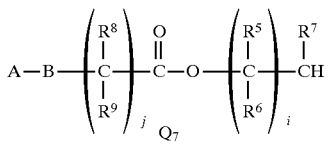

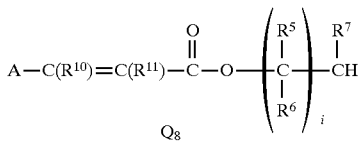

wherein A represents;
a phenyl group which may be substituted with $(R^{16})_q$,
a naphthyl group which may be substituted with $(R^{16})_q$ or
a heterocyclic group which may be substituted with $(R^{16})_q$, q represents an integer of 0 to 7, and
$R^{16}$ represents a halogen atom, a cyano group, a nitro group, a pentafluorosulfanyl group ($F_5S$), a ($C_1$–$C_4$ alkoxy)carbonyl group, a $C_1$–$C_8$ alkyl group, a $C_1$–$C_3$ haloalkyl group, a $C_1$–$C_7$ alkoxy group, a $C_1$–$C_3$ haloalkoxy group, a $C_1$–$C_3$ alkylthio group, a $C_1$–$C_3$ haloalkylthio group, a $C_1$–$C_2$ alkylsulfinyl group, a $C_1$–$C_2$ alkylsulfonyl group, a $C_1$–$C_2$ haloalkylsulfinyl group, a $C_1$–$C_2$ haloalkylsulfonyl group, a $C_3$–$C_6$ alkenyloxy group, a $C_3$–$C_6$ haloalkenyloxy group, a $C_2$–$C_4$ alkenyl group, a $C_2$–$C_4$ haloalkenyl group, a $C_2$–$C_4$ alkynyl group, a $C_2$–$C_4$ haloalkynyl group, a $C_3$–$C_6$ alkynyloxy group, a $C_3$–$C_6$ haloalkynyloxy group, a $C_1$–$C_3$ hydroxyalkyl group, a $C_2$–$C_4$ alkoxyalkyl group, a $C_2$–$C_4$ alkylthioalkyl group, an amino group, a dimethylamino group, an acetamide group, an acetyl group, a haloacetyl group, a formyl group, a carboxyl group, a ($C_1$–$C_2$ alkyl)aminocarbonyl group, [di($C_1$–$C_2$ alkyl)amino]carbonyl group, a $C_3$–$C_6$ cycloalkyl group, a $C_5$–$C_6$ cycloalkenyl group, a $C_3$–$C_6$ cycloalkyloxy group or a $C_5$–$C_6$ cycloalkenyloxy group, or
a phenyl, phenoxy, benzyl or benzyloxy group all of which may be substituted with at least one substituent group selected from a halogen atom, a $C_1$–$C_4$ alkyl group, a $C_1$–$C_3$ haloalkyl group, a $C_1$–$C_3$ alkoxy group and a $C_1$–$C_3$ haloalkoxy group; or
when q is an integer of 2 to 5, two adjacent $R^{16}$ bond together at their terminal ends to form a trimethylene group, a tetramethylene group, a methylenedioxy group which may be substituted with a halogen atom or a $C_1$–$C_3$ alkyl group, or an ethylenedioxy group which may be substituted with a halogen atom or a $C_1$–$C_3$ alkyl group;
B represents an oxygen atom, a $S(O)_n$ group, a $NR^{14}$ group, a $C(=O)G$ group or a $GC(=O)$ group, n represents an integer of 0 to 2 and $R^{14}$ represents a hydrogen atom or a $C_1$–$C_3$ alkyl group;

G represents an oxygen atom or a $NR^{15}$ group; and $R^{15}$ represents a hydrogen atom or a $C_1$–$C_3$ alkyl group;

$R^5$, $R^6$, $R^7$, $R^8$ and $R^9$ independently represent a hydrogen atom, a $C_1$–$C_3$ alkyl group or a trifluoromethyl group;

$R^{10}$ and $R^{11}$ independently represent a hydrogen atom, a $C_1$–$C_3$ alkyl group, a trifluoromethyl group or a halogen atom;

$R^{12}$ represents a halogen atom, a $C_1$–$C_4$ alkyl group, a $C_1$–$C_3$ haloalkyl group, a $C_1$–$C_3$ alkoxy group or a $C_1$–$C_3$ alkoxy group or a $C_1$–$C_3$ haloalkoxy group;

$R^{13}$ represents a hydrogen atom, a halogen atom or a methyl group;

i represents an integer of 0 to 6;

j represents an integer of 1 to 6;

k represents an integer of 0 to 4;

l represents 1 or 2; and m represents an integer of 0 to 2;

provided that $R^1$ does not represent a 3,3-dichloro-2-propenyl group, a 3,3dibromo-2-propenyl group or a 3-bromo-3-chloro-2-propenyl group;

when A is a naphtyl group which may be substituted with $(R^{16})_q$, $R^{16}$ is not a 3,3dichloro-2-propenyloxy group, a 3-,3-dibromo-2-propenyloxy group or a 3-bromo-3chloro-2-propenyloxy group; and when A is a phenyl group which may be substituted with $(R^{16})_q$ for $Q_1$, $Q_3$ and $Q_6$ and $R^{16}$ is a 3,3-dichloro-2-propenyloxy group, a 3,3-dibromo-2-propenyloxy group or a 3bromo-3-chloro-2-propenyloxygroup, q is equal to 1;

Z represents an oxygen atom, a sulfur atom or $NR^{17}$ in which $R^{17}$ represents a hydrogen atom or a $C_1$–$C_3$ alkyl group;

X represents a halogen atom;

$R^2$, $R^3$ and $R^4$ independently represent a $C_1$–$C_3$ alkyl group, a $C_1$–$C_3$ haloalkyl group, a halogen atom or a hydrogen atom; and r represents an integer of 0 to 2;

provided that $R^2$, $R^3$ and $R^4$ do not simultaneously represent a hydrogen atom.

The present invention also provides an insecticide comprising the same as an active ingredient.

The present invention further provides a novel compound represented by Formula III which is useful as an intermediate for production of some of the present compounds.

DESCRIPTION OF PREFERRED EMBODIMENT

In the present compound, examples of the $C_1$–$C_{10}$ alkyl group represented by $R^1$ include methyl group, ethyl group, propyl group, isopropyl group, butyl group, isobutyl group, secbutyl group, tert-butyl group, pentyl group, isopentyl group, neopentyl group, tert-pentyl group, hexyl group, heptyl group, 1-ethylpropyl group, 1,1-dimethylhexyl group, 1-methylbutyl group, 2-methylbutyl group, 1,2-dimethylpropyl group, isohexyl group, 1-methylpentyl group, 2-ethylbutyl group, octyl group, 1-methylheptyl group, 1-methyloctyl group, nonyl group, decyl group and the like.

Examples of the $C_1$–$C_5$ haloalkyl group represented by $R^1$ include trifluoromethyl group, difluoromethyl group, bromodifluoromethyl group, 2,2,2-trifluoroethyl group, 2-fluoroethyl group, 2-chloroethyl group, 2-bromoethyl group, 1-fluoroethyl group, 1-chloroethyl group, 1-bromoethyl group, 3,3,3,2,2-pentafluoropropyl group, 3,3,3-trifluoropropyl group, 1-fluoropropyl group, 2-chloropropyl group, 3-bromopropyl group, 1,1,2,2,2-pentafluoroethyl group, 2-iodoethyl group, 2,2-dichloroethyl group, 2-bromo-1,1,2,2-tetrafluoroethyl group, 1,1,2,2-tetrafluoroethyl group, 2-chloro-1,1,2-trifluoroethyl group, 2-bromo-1,2,2-trifluoroethyl group, 2,2,2-trichloroethyl group, 2,2,2-tribromoethyl group, 3-fluoropropyl group, 3-chloropropyl group, 3-iodopropyl group, 1,1,2,3,3,3-hexafluoropropyl group, 2,3-dibromopropyl group, 2,2,3,3-tetrafluoropropyl group, 2-chloro-1-methylethyl group, 2bromo-1-methylethyl group, 2-fluoro-1-(fluoromethyl)ethyl group, 2-bromo-1-(bromomethyl)ethyl group, 2-chlero-1-(chioromethyl)ethyl group, 2,2,2-trifluoro-1-(trifluoromethyl)ethyl group, 4-fluorobutyl group, 4-chlorobutyl group, 4-bromobutyl group, 4-iodobutyl group, 2-(bromomethyl)propyl group, 2,2,3,4,4,4-hexafluorobutyl group, 3bromo-1-(bromomethyl)propyl group, 2-chloro-2-methylpropyl group, 5-fluoropentyl group, 5-chloropentyl group, 5-bromopentyl group, 5-iodopentyl group, 3-chloro-2,2-dimethylpropyl group, 3-bromo-2,2-dimethylpropyl group, 2,2,3,3,4,4,5,5-octafluoropentyl group and the like.

Examples of the $C_2$–$C_{10}$ alkenyl group represented by $R^1$ include vinyl group, allyl group, isopropenyl group, 2-butenyl group, 3-butenyl group, 1-methyl-2-propenyl group, 2-methyl-2-propenyl group, 2-pentenyl group, 1-methyl-2-butenyl group, 2-methyl-2-butenyl group, 3-methyl-2-butenyl group, 1-ethyl-2-propenyl group, 2-ethyl-2-propenyl group, 1-methyl-3-butenyl group, 2-methyl-3-butenyl group, 3-methyl-3-butenyl group, 2-hexenyl group, 3-hexenyl group, 4-hexenyl group, 5-hexenyl group, 2-methyl-2-pentenyl group, 1,3-dimethyl-2-butenyl group, 1-methyl-4-pentenyl group, 1-ethyl-2-butenyl group, 2-ethyl-2-butenyl group, 1-vinylbutyl group, 2-isopropyl-2-propenyl group, 2-heptenyl group, 1allyl-3-butenyl group, 1-vinylhexyl group, 1,5-dimethyl-4-hexenyl group, 3-nonenyl group, 3-decenyl group, 3,7-dimethyl-6-octenyl group and the like.

Examples of the $C_2$–$C_6$ haloalkenyl group represented by $R^1$ include 2,2-dichloroethenyl group, 2,2-dibromoethenyl group, 2,3-dichloro-2-propenyl group, 2,3-dibromo-2-propenyl group, 2-chloro-2-propenyl group, 3-chloro-2-propenyl group, 2-bromo-2-propenyl group, 3-chloro-2-butenyl group, 2-chloroethenyl group, 3-bromo-2-propenyl group, 3,3-difluoro2-propenyl group, 4-chloro-2-butenyl group, 4,4,4-trifluoro-2-butenyl, 2-(chloromethyl)-2-propenyl group, 3-chloro-4,4,4-trifluoro-2-butenyl group, 4-bromo-3,4,4-trifluoro-2butenyl group, 3,4,4,4-tetrafluoro-2-butenyl group, 4,4-dichloro-3-butenyl group, 4,4dibromo-3-butenyl group, 6,6-dichloro-5-hexenyl group and the like.

Examples of the $C_3$–$C_9$ alkynyl group represented by $R^1$ include 2-propynyl group, 2-butynyl group, 3-butynyl group, 1-methyl-2-propynyl group, 2-pentynyl group, 3-pentynyl group, 4-pentynyl group, 1-methyl-3-butynyl group, 2-methyl-3-butynyl group, 1-ethyl-2-propynyl group, 2-hexynyl group, 3-hexynyl group, 2-heptynyl group, 3-octynyl group, 1-ethynylhexyl group, 3-nonynyl group, 5-hexynyl group and the like.

Examples of the $C_3$–$C_5$ haloalkynyl group represented by $R^1$ include 3-chloro-2-propynyl group, 3-bromo-2-propynyl group, 3-iodo-2-propynyl group, 1-methyl-3-chloro-2-propynyl group, 1-methyl-3-bromo-2-propynyl group, 1-methyl-3-iodo-2-propynyl group, 4-chloro-2-butynyl group, 4-chloro-3-butynyl group, 4-bromo-3-butynyl group, 5-chloro-4-pentynyl group, 5-bromo-4-pentynyl group, 4-chloro-2-methyl-3-butynyl group, 4-bromo-2-methyl-3-butynyl group, 4-chloro-1-methyl-3-butynyl group, 4-bromo-1-methyl-3-butynyl group, 3-chloro-1-ethyl-2-propynyl group, 3-bromo-1-ethyl-2-propynyl group and the like.

Examples of the $C_2$–$C_7$ alkoxyalkyl group represented by $R^1$ include methoxymethyl group, ethoxymethyl group, propyloxymethyl group, isopropyloxymethyl group, 2-methoxyethyl group, 1-methoxyethyl group, 2-ethoxyethyl group, 1-ethoxyethyl group, 3-methoxypropyl group, 2-methoxypropyl group, 1-methoxypropyl group, 2-methoxy-1-methylethyl group, 2-propyloxyethyl group, 2-isopropyloxyethyl group, 2-ethoxy-2-methylethyl group, 2-ethoxy-1-methylethyl group, 2-methoxybutyl group, 1-ethyl-2-methoxyethyl group, 3-ethoxypropyl group, 3-methoxybutyl group, 3-methoxy-2-methylpropyl group, 3-methoxy-1-methylpropyl group, 2-butoxyethyl group 3-methoxy-3-methylbutyl group, 2-butoxy-1-methylethyl group and the like.

Examples of the $C_2$–$C_7$ alkylthioalkyl group represented by $R^1$ include methylthiomethyl group, ethylthiomethyl group, propylthiomethyl group, isopropylthiomethyl group, 2-methylthioethyl group, 1-methylthioethyl group, 2-ethylthioethyl group, 1-ethylthioethyl group, 3-methylthiopropyl group, 2-methylthiopropyl group, 1-methylthiopropyl group, 2-methylthio-1-methylethyl group, 2-propylthioethyl group, 2-isopropylthioethyl group, 2-ethylthiopropyl group, 2-ethylthio-1-methylethyl group, 2-methylthiobutyl group, 1-ethyl-2-methylthioethyl group, 3-ethylthiopropyl group, 3-methylthiobutyl group, 2-methyl-3-methylthiopropyl group, 1-methyl-3-methylthiopropyl group, 4-methylthiobutyl group, 1-methyl-2-methylthiopropyl group, 2-tert-butylthioethyl group, 2-isobutylthioethyl group, 2-sec-butylthioethyl group, 3-tert-butylthiopropyl group, 3-isobutylthiopropyl group, 3-sec-butylthiopropyl and the like.

Examples of the $C_1$–$C_4$ alkyl group in the $C_3$–$C_6$ cycloalkyl group which may be substituted with the $C_1$–$C_4$ alkyl group, $C_1$–$C_3$ alkoxy group or $C_1$–$C$ haloalkoxy group, represented by $R^1$, include methyl group, ethyl group, propyl group, isopropyl group, butyl group, isobutyl group, sec-butyl group or tert-butyl group.

Examples of the $C_1$–$C_3$ alkoxy group in the $C_3$–$C_6$ cycloalkyl group which may be substituted with the $C_1$–$C_4$ alkyl group, $C_1$–$C_3$ alkoxy group or $C_1$–$C_3$ haloalkoxy group, represented by $R^1$, include methoxy group, ethoxy group, propoxy group or isopropoxy group.

Examples of the $C_1$–$C_3$ haloalkoxy group in the $C_3$–$C_6$ cycloalkyl group which may be substituted with the $C_1$–$C_4$ alkyl group, $C_1$–$C_3$ alkoxy group or $C_1$–$C_3$ haloalkoxy group, represented by $R^1$, include trifluoromethoxy group, difluoromethoxy group, bromodifluoromethoxy group, 2,2,2-trifluoroethoxy group, 2,2,2,1,1-pentafluoroethoxy group, 2-chloroethoxy group, 2-bromoethoxy group, 2-chloro-1,1,2-trifluoroethoxy group, 2-bromo-1,1,2-trifluoroethoxy group, 1,1,2,2-tetrafluoroethoxy group, 3,3,3,2,2,1-hexafluoropropoxy group and the like.

Examples of the $C_3$–$C_6$ cycloalkyl group in the $C_3$–$C_6$ cycloalkyl group which may be substituted with the $C_1$–$C_4$ alkyl group, $C_1$–$C_3$ alkoxy group or $C_1$–$C_3$ haloalkoxy group, represented by $R^1$, include cyclopropyl group, cyclobutyl group, cyclopentyl group or cyclohexyl group.

Examples of the $C_1$–$C_4$ alkyl group in the $C_4$–$C_9$ cycloalkyl group which may be substituted with the $C_1$–$C_4$ alkyl group, represented by $R^1$, include methyl group, ethyl group, propyl group, isopropyl group, butyl group, isobutyl group, sec-butyl group or tert-butyl group.

Examples of the $C_4$–$C_9$ cycloalkylalkyl group in the $C_4$–$C_9$ cycloalkylalkyl group which may be substituted with the $C_1$–$C_4$ alkyl group, represented by $R^1$, include cyclopropylmethyl group, 1-cyclopropylethyl group, 2-cyclopropylethyl group, cyclobutylmethyl group, cyclopentylmethyl group, 2-cyclopentylethyl group, 3-cyclopentylpiopyl group, cyclohexylmethyl group, 2-cyclohexylethyl group, 3-cyclohexylpropyl group and the like.

Examples of the $C_1$–$C_4$ alkyl group in the $C_5$–$C_6$ cycloalkenyl group which may be substituted with the $C_1$–$C_4$ alkyl group, represented by $R^1$, include methyl group, ethyl group, propyl group, isopropyl group, butyl group, isobutyl group, sec-butyl group or tert-butyl group.

Examples of the $C_5$–$C_6$ cycloalkenyl group in the $C_5$–$C_6$ cycloalkenyl group which may be substituted with $C_1$–$C_4$ alkyl group, represented by $R^1$, include 1-cyclopentenyl group, 2-cyclopentenyl group, 3-cyclopentenyl group, 1-cyclohexenyl group, 2-cyclohexenyl group or 3-cyclohexenyl group.

Examples of the $C_1$–$C_4$ alkyl group in the $C_6$–$C_8$ cycloalkenylalkyl group which may be substituted with the $C_1$–$C_4$ alkyl group, represented by $R^1$, include methyl group, ethyl group, propyl group, isopropyl group, butyl group, isobutyl group, sec-butyl group or tert-butyl group.

Examples of the $C_6$–$C_8$ cycloalkenyialkyl group in the $C_6$–$C_8$ cycloalkenylalkyl group which may be substituted with the $C_1$–$C_4$ alkyl group, represented by $R^1$, include 1-cyclopentenylmethyl group, 2-cyclopentenylmethyl group, 3-cyclopentenylmethyl group, 1-cyclohexenylmethyl group, 2-cyclohexenylmethyl group, 3-cyclohexenylmethyl group, 2-(3-cyclohexenyl)ethyl group and the like.

Examples of the halogen atom represented by $R^2$, $R^3$, $R^4$, $R^{10}$, $R^{11}$ $R^{12}$, $R^{13}$, X and $R^{16}$ include fluorine atom, chlorine atom, bromine atom or iodine atom. The halogen can be independently selected from these groups.

Examples of the $C_1$–$C_4$ alkyl group represented by $R^{12}$ include methyl group, ethyl group, propyl group, isopropyl group, butyl group, isobutyl group, sec-butyl group or tert-butyl group.

Examples of the $C_1$–$C_8$ alkyl group represented by $R^{16}$ include methyl group, ethyl group, propyl group, isopropyl group, butyl group, isobutyl group, sec-butyl group, tert-butyl group, pentyl group, isopentyl group, neopentyl group, tert-pentyl group, hexyl group, heptyl group, 1,1-dimethylhexyl group, 1-methylbutyl group, 2-methylbutyl group, 1,2dimethylpropyl group, isohexyl group, 1-methylpentyl group, 2-ethylbutyl group, octyl group, 1-methylheptyl group and the like.

Examples of the $C_1C_3$ haloalkyl group represented by $R^2$, $R^3$, $R^4$, $R^{12}$ and $R^{16}$ include trifluoromethyl group, trichloromethyl group, difluoromethyl group, bromodifluoromethyl group, 2,2,2-trifluoroethyl group, 2-fluoroethyl group, 2-chloroethyl group, 2-bromoethyl group, 1-fluoroethyl group, 1-chloroethyl group, 1-bromoethyl group, 3,3,3,2,2-pentafluoropropyl group, 3,3,3-trifluoropropyl group, 1-fluoropropyl group, 2-chloropropyl group, 3-bromopropyl group and the like.

Examples of the $C_1$–$C_3$ alkoxy group represented by $R^{12}$ include methoxy group, ethoxy group, propoxy group, isopropoxy group and the like.

Examples of the $C_1$–$C_3$ haloalkoxy group represented by $R^{12}$ and $R^{16}$ include trifluoromethoxy group, difluoromethoxy bromodifluoromethoxy group, 2-fluoroethoxy group, 2,2,2-trifluoroethoxy group, 2-chloroethoxy group, 2-bromoethoxy group, 2-chloro- 1,1,2-trifluoroethoxy group, 2-bromo-1,1,2-trifluoroethoxy group 1,1,2,2-tetrafluoroethoxy group, 3,3,3,2,2,1-hexafluoropropoxy group, 3-fluoropropoxy group, 3-chloropropoxy group, 3-bromopropoxy group, 3,3,3,2,2-pentafluoropropoxy group, 3,3,3-trifluoropropoxy group, 2,2,2,1,1-pentafluoroethoxy group, 3,3,3,2,1,1-hexafluoropropoxy group and the like.

Examples of the $C_1$–$C_3$ alkyl group represented by $R^2$, $R^3$, $R^4$, $R^5$, $R^6$, $R^7$, $R^8$, $R^9$, $R^{10}$, $R^{17}$, $R^{11}$, $R^{14}$, $R^{15}$ include methyl group, ethyl group, propyl group or isopropyl group.

Examples of the $C_1$–$C_7$ alkoxy group represented by $R^{16}$ include methoxy group, ethoxy group, propoxy group, isopropoxy group, butoxy group, sec-butoxy group, isobutoxy group, tert-butoxy group, pentyloxy group, isopentyloxy group, 1-methylbutoxy group, 1-ethylpropoxy group, neopentyloxy group, tert-pentyloxy group, 1,2-dimethylpropoxy group, hexyloxy group, heptyloxy group and the like.

Examples of the $C_1$–$C_3$ alkylthio group represented by $R^{16}$ include methylthio group, ethylthio group, propylthio group, isopropylthio group and the like.

Examples of the $C_1$–$C_3$ haloalkylthio group represented by $R^{16}$ include trifluoromethylthio group, difluoromethylthio group, bromodifluoromethylthio group, 2,2,2-trifluoroethylthio group, 2-chloro-1,1,2-trifluoroethylthio group, 2-bromo-1,1,2-trifluoroethylthio group, 1,1,2,2-tetrafluoroethylthio group, 2-chloroetliylthio group, 2fluoroethylthio group, 2-bromoethylthio group, 1,1,2,2,2-pentafluoroethylthio group, 3-fluoropropylthio group, 3-chloropropylthio group, 3-bromopropylthio group, 3,3,3,2,2-pentafluoropropylthio group, 3,3,3-trifluoropropylthio group and the like.

Examples of the $C_3$–$C_6$ alkenyloxy group represented by $R^{16}$ include allyloxy group, 2-methyl-2-propenyloxy group, 1-methyl-2-propenyloxy group, 2-butenyloxy group, 3methyl-2-butenyloxy group, 2-methyl-2-butenyloxy group, 2-pentenyloxy group, 2-hexenyloxy group and the like.

Examples of the $C_3$–$C_6$ haloalkenyloxy group represented by $R^{16}$ include 3,3-dichloro2-propenyloxy group, 3,3-dibromo-2-propenyloxy group, 2,3-dichloro-2-propenyloxy group, 2,3-dibromo-2-propenyloxy group, 2-chloro-2-propenyloxy group, 3-chloro-2-propenyloxy group, 2-bromo-2-propenyloxy group, 3-fluoro-3-chloro-2-propenyloxy group, 3-methyl-4,4,4-trifluoro-2-butenyloxy group, 3-chloro-2-butenyloxy group and the like.

Examples of the $C_2$–$C_4$ alkenyl group represented by $R^{16}$ include vinyl group, isopropenyl group, 1-propenyl group, 2-methyl-1-propenyl group, 1-methyl-1-propenyl group, allyl group, 1-methyl-2-propenyl group, 2-butenyl group and the like.

Examples of the $C_2$–$C_4$ haloalkenyl group represented by $R^{16}$ include 2,2-dichloroethenyl group, 2,2-dibromoethenyl group, 3,3-dichloro-2-propenyl group, 3,3dibromo-2-propenyl group, 2,3-dichloro-2-propenyl group, 2,3-dibromo-2-propenyl group, 2-chloro-2-propenyl group, 3-chloro-2-propenyl group, 2-bromo-2-propenyl, 3-chloro-2butenyl group and the like.

Examples of the $C_2$–$C_4$ alkynyl group represented by $R^{16}$ include ethynyl group, 1-propynyl group, 2-propynyl group, 1-methyl-2-propynyl group and the like.

Examples of the $C_2$–$C_4$ haloalkynyl group represented by $R^{16}$ include chloroethynyl, bromoethynyl group, iodoethynyl group, 3-chloro-2-propynyl group, 3-bromo-2-propynyl group, 3-iodo-2-propynyl group, 1-methyl-3-chloro-2-propynyl group, 1-methyl-3-bromo2-propynyl group, 1-methyl-3-iodo-2-propynyl group and the like.

Examples of the $C_2$–$C_4$ alkoxyalkyl group represented by $R^{16}$ include methoxymethyl group, ethoxymethyl group, propyloxymethyl group, isopropyloxymethyl group, 2-methoxyethyl group, 1-methoxyethyl group, 2-ethoxyethyl group, 1-ethoxyethyl group, 3-methoxypropyl group, 2-methoxypropyl group, 1-methoxypropyl group, 2-methoxy-1-methylethyl group and the like.

Examples of the $C_2$–$C_4$ alkylthioalkyl group represented by $R^{16}$ include methylthiomethyl group, ethylthiomethyl group, propylthiomethyl group, isopropylthiomethyl group, 2-methylthioethyl group, 1-methylthioethyl group, 2-ethylthioethyl group, 1-ethylthioethyl group, 3-methylthiopropyl group, 2-methylthiopropyl group, 1-methylthiopropyl group, 2-methylthio-1-methylethyl group and the like.

Examples of the $C_3$–$C_6$ cycloalkyl group represented by $R^{16}$ include cyclopropyl group, cyclobutyl group, cyclopentyl group, cyclohexyl group and the like.

Examples of the $C_5$–$C_6$ cycloalkenyl group represented by $R^{16}$ include 1-cyclopentenyl group, 2-cyclopentenyl group, 3-cyclopentenyl group, 1-cyclohexenyl group, 2-cyclohexenyl group, 3-cyclohexenyl group and the like.

Examples of the $C_3$–$C_6$ cycloalkyloxy group represented by $R^{16}$ include cyclopropyloxy group, cyclobutyloxy group, cyclopentyloxy group, cyclohexyloxy group and the like.

Examples of the $C_5$–$C_6$ cycloalkenyloxy group represented by $R^{16}$ include 1-cyclopentenyloxy group, 2-cyclopentenyloxy group, 3-cyclopentenyloxy group, 1-cyclohexenyloxy group, 2-cyclohexenyloxy group, 3-cyclohexenyloxy group and the like.

Examples of the $C_1$–$C_2$ alkylsulfinyl group represented by $R^{16}$ include methylsulfinyl group or ethylsulfinyl group.

Examples of the $C_1$–$C_2$ alkylsulfonyl group represented by $R^{16}$ include methylsulfonyl group or ethylsulfonyl group.

Examples of the $C_1$–$C_2$ haloalkylsulfinyl group represented by $R^{16}$ include trifluoromethylsulfinyl group, 2,2,2-trifluoroethylsulfinyl group, perfluoroethylsulfinyl group and the like.

Examples of the $C_1$–$C_2$ haloalkylsulfonyl group represented by $R^{16}$ include trifluoromethylsulfonyl group, 2,2,2-trifluoroethylsulfonyl group, perfluoroethylsulfonyl group and the like.

Examples of the ($C_1$–$C_2$ alkyl)aminocarbonyl group represented by $R^{16}$ include methylaminocarbonyl group or ethylaninocarbonyl group.

Examples of the $C_1$–$C_3$ hydroxyalkyl group represented by $R^{16}$ include hydroxymethyl group, 2-hydroxyethyl group, 3-hydroxypropyl group and the like.

Examples of the [di($C_1$–$C_2$ alkyl)amino]carbonyl group represented by $R^{16}$ include dimethylaminocarbonyl group, N-methyl-N-ethylaminocarbonyl group, diethylaminocarbonyl group and the like.

Examples of the $C_1$–$C_4$ alkyl group in the phenyl, phenoxy, benzyl or benzyloxy group which may be substituted with the halogen atom, $C_1$–$C_4$ alkyl group, $C_1$–$C_3$ haloalkyl group, $C_1$–$C_3$ alkoxy group or $C_1$–$C_3$ haloalkoxy group, represented by $R^{16}$, include methyl group, ethyl group, propyl group, isopropyl group, butyl group, sec-butyl group, tert-butyl group or isobutyl group and the like.

Examples of the $C_1$–$C_3$ haloalkyl group in the phenyl, phenoxy, benzyl or benzyloxy group which may be substituted with the halogen atom, $C_1$–$C_4$ alkyl group, $C_1$–$C_3$ haloalkyl group, $C_1$–$C_3$ alkoxy group or $C_1$–$C_3$ haloalkoxy group, represented by $R^{16}$, include trifluoromethyl group, difluoromethyl group, bromodifluoromethyl group, 2,2-difluoroethyl group, 2,2,2-trifluoroethyl group, 2-fluoroethyl group, 2-chloroethyl group, 2-bromoethyl group, 1-fluoroethyl group, 1-chloroethyl group, 1-bromoethyl group, 3,3,3,2,2-pentafluoropropyl group, 3,3,3-trifluoropropyl garoup, 1-fluoropropyl group, 2-chloropropyl group, 3-bromopropyl group and the like.

Examples of the $C_1$–$C_3$ alkoxy group in the phenyl, phenoxy, benzyl or benzyloxy group which may be substituted with the halogen atom, $C_1$–$C_4$ alkyl group, $C_1$–$C_3$ haloalkyl group, $C_1$–$C_3$ alkoxy group or $C_1$–$C_3$ haloalkoxy group, represented by $R^{16}$, include methoxy group, ethoxy group, propoxy group or isopropoxy group.

Examples of the $C_1$–$C_3$ haloalkoxy group in the phenyl, phenoxy, benzyl or benzyloxy group which may be substituted with the halogen atom, $C_1$–$C_4$ alkyl group, $C_1$–$C_3$ haloalkyl group, $C_1$–$C_3$ alkoxy group or $C_1$–$C_3$ haloalkoxy group, represented by $R^{16}$, include trifluoromethoxy group, difluoromethoxy bromodifluoromethoxy group, 2-fluoroethoxy group, 2,2,2-trifluoroethoxy group, 2-chloroethoxy group, 2-bromoethoxy group, 2-chloro-1,1,2-trifluoroethoxy group, 2-bromo-1,1,2-trifluoroethoxy group, 1,1,2,2-tetrafluoroethoxy group, 3,3,3,2,2,1-hexafluoropropoxy group, 3-fluoropropoxy group, 3-chloropropoxy group, 3-bromopropoxy group, 3,3,3,2,2-pentafluoropropoxy group, 3,3,3-trifluoropropoxy group, 2,2,2,1,1-pentafluoroethoxy group and the like.

Examples of the halogen atom in the methylenedioxy group which may be substituted with halogen atom or ethylenedioxy group which may be substituted with halogen atom, which is formed by bonding two adjacent $R^{16}$ together at their terminal ends, when q is from 2 to 5, represented by $R^{16}$, include fluorine atom, chlorine atom, bromine atom or iodide atom.

Examples of the $C_1$–$C_3$ alkyl group in the methylenedioxy group which may be substituted with $C_1$–$C_3$ alkyl group or ethylenedioxy group which may be substituted with $C_1$–$C_3$ alkyl group, which is formed by bonding two adjacent $R^{16}$ together at their terminal ends, when q is from 2 to 5, represented by $R^{16}$, include methyl group, ethyl group, propyl group or isopropyl group.

Examples of the heterocyclic group in the optionally substituted heterocyclic group represented by A include isoxazole, isothiadiazole, thiazole, 1,3,4-thiadiazole, pyrrole, furan, thiophene, pyrazole, imidazole, 1,2,3-triazole, 1,2,4-triazole, 1,2,3,4-tetrazole, pyridine, pyridazine, pyrimidine, pyrazine, 1,2,4-triazine, 1,3,5-triazine, indole, benzofuran, thianaphthalene, indazole, benzirnidazole, benzotriazole, benzisoxazole, benzoxazole, benzothiazole, quinoline, isoquinoline, quinoxaline, quinazoline, piperidine, piperazine, tetrahydrofuran, tetrahydropyran, pyrazoline and the like.

In the present compound, preferred embodiments of $R^1$ include:

$Q_1$ and A is a phenyl group which may be substituted with $(R^{16})_q$ or 2-pyridyl group which may be substituted with $(R^{16})_q$;

$Q_2$ and A is phenyl group which may be substituted with $(R^{16})_q$ or 2-pyridyl group which may be substituted with $(R^{16})_q$;

$Q_3$ and A is a phenyl group which may be substituted with $(R^{16})_q$ or 2-pyridyl group which may be substituted with $(R^{16})_q$;

$Q_4$, $Q_5$, $Q_6$, $Q_7$, $Q_8$ or $Q_9$ and A is a phenyl group which may be substituted with $(R^{16})_q$ or 2-pyridyl group which may be substituted with $(R^{16})_q$.

Preferred embodiments of Z include oxygen atom or a sulfur atom, and more preferred embodiments include an oxygen atom.

Preferred embodiments of B include oxygen atom, $CO_2$ group or CONH group.

Preferred embodiments of X include a chlorine atom and a bromine atom.

In the present compound, examples of the preferred compound include:

a compound wherein $R^1$ is $Q_1$, in which A is a phenyl group which may be substituted with $(R^{16})_q$ or 2-pyridyl group which may be substituted with $(R^{16})_q$, Z is an oxygen atom, r is 0, X is a chlorine atom or a bromine atom, and $R^2$ and $R^3$ do not simultaneously represent a hydrogen atom;

a compound wherein $R^1$ is $Q_2$, in which A is a phenyl group which may be substituted with $(R^{16})_q$ or 2-pyridyl group which may be substituted with $(R^{16})_q$, Z is an oxygen atom, $R^5$, $R^6$ and $R^7$ respectively represent a hydrogen atom, i is an integer of 0 to 3, r is 0, X is a chlorine atom or a bromine atom, and $R^2$ and $R^3$ do not simultaneously represent a hydrogen atom; and a compound wherein $R^1$ is $Q_3$, in which A is a phenyl group which may be substituted with $(R^{16})_q$ or 2-pyridyl group which may be substituted with $(R^{16})_q$, Z is an oxygen atom, B is an oxygen atom, a $CO_2$ group or a CONH group, $R^5$, $R^6$ and $R^7$ independently represent a hydrogen atom, i is 2 to 4, r is 0, X is a chlorine atom or a bromine atom, and $R^2$ and $R^3$ do not simultaneously represent a hydrogen atom.

Among the preferred compounds, $R^{16}$ is more preferably a halogen atom, a $C_1$–$C_3$ haloalkyl group, a $C_1$–$C_4$ alkoxyl group or a $C_1$–$C_3$ haloalkoxy group; $R^2$ and $R^3$ independently represent a $C_1$–$C_3$ alkyl group, a $C_1$–$C_3$ haloalkyl group (e.g., a trifluoromethyl group) or a halogen atom, and more preferably, $R^2$ and $R^3$ independently represent a $C_1$–$C_2$ alkyl group, a trifluoromethyl group or a halogen atom.

The present compound can be produced, for example, by the following processes.
Process A to Process G.
Process A
In the compound of Formula I, when $R^1$ is other than $Q_1$, and Z is an oxygen atom, the following Process A is employed.

Process A for producing the compound of formula 1 comprises reacting an alcohol compound represented by Formula IV:

$$R^1\text{—OH}$$

wherein $R^1$ is as defined above with a compound represented by Formula III.

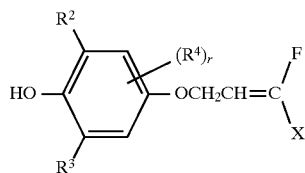

wherein $R^2$, $R^3$, $R^4$, r and X are as defined above,

It is preferred that the above reaction is carried out in an inert solvent in the presence of a suitable dehydrating agent.

Examples of the dehydrating agent used include dicyclohexylcarbodiimide, dialkyl (e.g., $C_1$–$C_4$) azodicarboxylate (e.g., diethylazodicarboxylate, diisopropylazodicarboxylate, etc.), trialkyl (e.g., $C_1$–$C_{20}$) phosphine or triarylphosphine (e.g., triphenylphosphine, trioctylphosphine, tributylphosphine, etc.) and the like.

Examples of the solvent used include hydrocarbons such as benzene, xylene, toluene, etc., ethers such as diethyl ether, diisopropyl ether, tetrahydrofuran, dioxane, etc., or hydrocarbon halides such as carbon tetrachloride, dichloromethane, chlorobenzene, dichlorobenzene, among others, including mixtures of solvents.

The reaction temperature may be normally within a range from −20° C. to 200° C. or the boiling point of the solvent used.

The molar ratio of the compounds of Formula III and IV and dehydrating agent used for the reaction can be appropriately set, but it is advantageous to conduct the reaction using them in an equimolar ratio or substantially equimolar ratio.

After completion of the reaction, the reaction solution can be subjected to a normal post treatment such as organic solvent extraction, concentration, etc. to isolate the desired present compound. If necessary, the resulting compound can be further purified by a normal operation such as chromatography, distillation, recrystallization, etc.

Process B

Process B for producing the compound of Formula I comprises reacting a halide compound represented by Formula V:

$$R^1—L^1$$

wherein $R^1$ is as defined above, and $L^1$ represents a halogen atom (e.g. chlorine atom, bromine atom, iodine atom, etc.), a mesyloxy group or a tosyloxy group with a compound represented by Formula VI:

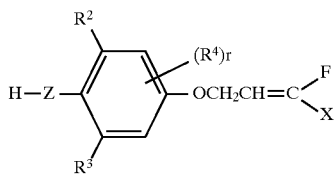

wherein Z, $R^2$, $R^3$, $R^4$, r and X are as defined above.

It is preferred that the above reaction is carried out in an inert solvent in the presence of a suitable base.

Examples of the solvent used include ketones such as acetone, methyl ethyl ketone, cyclohexanone; ethers such as 1,2-dimethoxyethane, tetrahydrofuran, dioxane, dialkyl (e.g. $C_1$–$C_4$) ether (e.g. diethyl ether, dilsopropyl ether, etc.); polar solvents such as N,N-dimethylformamide, dimethyl sulfoxide, triamide hexamethylphosphate. sulfolane, acetonitrile, nitromethane, etc.; hydrocarbon halides such as dichloromethane, chloroform, 1,2-dichloroethane, chiorobenzene, etc.; hydrocarbons such as toluene, benzene, xylene, etc.; or water, etc. A mixed solvent of these solvents can be optionally used.

Examples of the base used include hydroxides of alkaline or alkaline earth metals, such as lithium hydroxide, sodium hydroxide, potassium hydroxide, calcium hydroxide, etc.; carbonates of alkaline or alkaline earth metals, such as lithium carbonate, potassium carbonate, sodium carbonate, calcium carbonate, etc.; hydrides of alkaline or alkaline earth metals, such as lithium hydride, sodium hydride, potassium hydride, calcium hydride, etc.; alkaline metal alkoxides (e.g. $C_1$–$C_4$), such as sodium methoxide, sodium ethoxide, potassium tert-butoxide, etc.; and organic bases such as triethylamine, pyridine, etc.

A catalyst such as an ammonium salt (e.g., triethylbenzylamrnmonium chloride, etc.) may be optionally added to the reaction system in a proportion of 0.01–1 mol, based on 1 mol of the compound represented by Formula VI.

The reaction temperature may be normally within a range from −20° C. to the boiling point of the solvent used for the reaction or 150° C., preferably from −5° C. to the boiling point of the solvent used for the reaction or 100° C.

The molar ratio of the compounds of Formula V and VI and base used for the reaction can be appropriately set, but it is advantageous to conduct the reaction using them in an equimolar ratio or substantially equimolar ratio.

After the completion of the reaction, the reaction solution can be subjected to a normal post treatment such as organic solvent extraction, concentration, etc. to isolate the desired present compound. If necessary, the resulting compound can be further purified by a normal operation such as chromatography, distillation, recrystallization, etc.

Process C

Process C for producing the compound of Formula I comprises reacting an aldehyde compound represented by Formula VII:

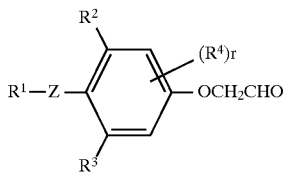

wherein $R^1$, $R^2$, $R^3$, $R^4$, r and Z are as defined above with trialkylphosphine, triarylphosphine or tri(alkylamino) phosphine and a halogen compound represented by Formula VIII:

$$CF_2X_2, CFX_3, CF_2XC(=O)—ONa \text{ or } CFX_2C(=O)—ONa$$

wherein X is as defined above.

The above reaction can also be carried out in an inert solvent in the presence of metallic zinc, if necessary.

Examples of the inert solvent used include hydrocarbons such as benzene, xylene, toluene, etc.; ethers such as diethyl ether, diisopropyl ether, tetrahydrofuran, dioxane, etc.; hydrocarbon halides such as dichloromethane, 1,2-dichloroethane, chlorobenzene, etc. (excluding carbon tetrabromide and carbon tetrachloride) and a mixed solvent thereof The reaction temperature may be normally within a range from −30° C. to the boiling point of the solvent used for the reaction or 200° C.

Examples of the (trialkyl $C_1$–$C_{20}$)phosphine, triarylphosphine or tri(alkylamino)phosphine include triphenylphosphine, trioctylphosphine, tris(dimethylarino) phosphine and the like. The metallic zinc which may be used according to the necessity is in relatively fine particulate form. By preference, the metallic zinc comprises zinc dust.

The molar ratio of the compound of Formula VII and VIII used for the reaction can be appropriately set. The proportion of the halogen compound of Formula VIII, that of trialkylphosphine, trialllylphosphine or tri(alkylamino) phosphine are 1–5 moles and 2–10 moles respectively based on 1 mole of the aldehyde compound of Formula VII.

When zinc is employed, 1–5 moles of zinc may be preferably used based on 1 mole of the aldehyde compound of Formula VII.

It is advantageous to react them in substantially similar proportion as described above.

After the completion of the reaction, the reaction solution can be subjected to a normal post treatment such as organic solvent extraction, concentration, etc. to isolate the objective present compound. If necessary, the resulting compound can be further purified by a normal operation such as chromatography distillation, recrystallization, etc.

Process D

In Formula I, when Z=0, $R^1=Q_3$ or $Q_4$, and $B=B^1$ ($B^1$ represents an oxygen atom, a sulfur atom or $NR^{14}$, and $R^{14}$ is as defined above, following Process D is employed.

Process D for producing the compound of Formula I comprises reacting a compound represented by Formula IX:

$$HB^1 \left( \begin{array}{c} R^5 \\ | \\ | \\ R^6 \end{array} \right) \begin{array}{c} R^7 \\ | \\ CH-O \end{array} \underset{R^3}{\overset{R^2}{\bigcirc}} \begin{array}{c} (R^4)_r \\ \\ OCH_2CH=C \end{array} \begin{array}{c} F \\ \diagdown \\ X \end{array}$$

wherein $R_2$, $R^3$, $R^4$, r, $B^1$, $R^5$, $R^6$, $R^7$, i and X are as defined above with a compound represented by Formula X:

$A-L^1$

OR $$A \left( \begin{array}{c} R^8 \\ | \\ C \\ | \\ R^9 \end{array} \right)_j L^1$$

wherein A, $R^8$, $R^9$, $L^1$ and j are as defined above.

It is preferred that the above reaction is carried out in an inert solvent in the presence of a suitable base.

Examples of the solvent used include ketones such as acetone., methyl ethyl ketone, cyclohexanone, etc.; ethers such as 1,2-dimethoxyethane, tetrahydrofuran, dioxane, dialkyl (e.g., $C_1$–$C_4$) ether (e.g., diethyl ether, diisopropyl ether, etc.); polar solvents such as N,N-dimethylformamide, dimethyl sulfoxide, triamide hexamethylphosphate, sulfolane, acetonitrile, nitromethane, etc.; hydrocarbon halides such as dichloromethane, chloroform, 1,2-dichloroethane, chlorobenzene, etc.; hydrocarbons such as toluene, benzene, xylene, etc.; or water, etc. A mixed solvent of these solvents can be optionally used.

Examples of the base include hydroxides of alkali or alkaline earth metals, such as lithium hydroxide, sodium hydroxide, potassium hydroxide, calcium hydroxide, etc.; carbonates of alkali or alkaline earth metals, such as lithium carbonate, potassium carbonate, sodium carbonate, calcium carbonate, etc.; hydrides of alkali or alkaline earth metals, such as lithium hydride, sodium hydride, potassium hydride, calcium hydride, etc.; alkali, metal alkoxides (e.g. $C_1$–$C_4$), such as sodium methoxide, sodium ethoxide, potassium tert-butoxide, etc.; and organic bases such as triethylamine, pyridine, etc. A catalyst such as an ammonium salt (e.g. triethylbenzylammonium chloride, etc.) may be optionally added to the reaction system in a proportion of 0.01–1 mol, based on 1 mol of the compound represented by Formula IX.

The reaction temperature may be normally within a range from –20° C. to the boiling point of the solvent used for the reaction or 150° C., preferably from –5° C. to the boiling point of the solvent used for the reaction or 100° C.

The molar ratio of the compounds of Formula IX and X and base used for the reaction can be appropriately set, but it is advantageous to conduct the reaction using them in an equimolar ratio or substantially equimolar ratio.

After the completion of the reaction, the reaction solution can be subjected to a normal post treatment such as organic solvent extraction, concentration, etc. to isolate the desired present compound. If necessary, the resulting compound can be further purified by a normal operation such as chromatography, distillation, recrystallization, etc.

Process E

In Formula I, when Z=B=0, $R^1$—$Q_3$, $Q_4$, $Q_7$ or $Q_8$, Process E is employed.

Process E for producing the compound of Formula I comprises reacting an alcohol compound represented by Formula XI:

$$HO \left( \begin{array}{c} R^5 \\ | \\ | \\ R^6 \end{array} \right)_i CH-O \underset{R^3}{\overset{R^2}{\bigcirc}} \begin{array}{c} (R^4)_r \\ \\ OCH_2CH=C \end{array} \begin{array}{c} F \\ \diagdown \\ X \end{array}$$

wherein $R^2$, $R^3$, $R^4$, r, $R^5$, $R^6$, $R^7$, i find X are as defined above with a compound represented by Formula XII;

$A-OH$      $Q_{31}$ $$A \left( \begin{array}{c} R^8 \\ | \\ C \\ | \\ R^9 \end{array} \right)_j OH \quad Q_{41}$$

OR $$A-O \left( \begin{array}{c} R^8 \\ | \\ C \\ | \\ R^9 \end{array} \right)_j \begin{array}{c} O \\ || \\ COH \end{array} \quad Q_{71}$$

or $A-C(R^{10})=C(R^{11})-COOH \quad Q_{81}$

It is preferred that the above reaction is carried out in an inert solvent in the presence of a suitable dehydrating agent.

Examples of the dehydrating agent used include dicyclohexylcarbodiimide, dialkyl (e.g., $C_1$–$C_4$) azodicarboxylate (e.g., diethylazodicarboxylate, diisopropylazodicarboxylate, etc.), trialkyl (e.g., $C_1$–$C_{20}$) phosphine or triarylphosphine (e.g., triphenylphosphine, trioctylphosphine, tributylphosphine, etc.) and the like.

Examples of the solvent used include hydrocarbons such as benzene, xylene, toluene, etc., ethers such as diethyl ether, diisopropyl ether, tetrahydrofluran, dioxane, etc., or hydrocarbon halides such as carbon tetrachloride, dichloromethane, chlorobenzene, dichlorobenzene, etc. An optional mixed solvent thereof may be used.

The reaction temperature may be normally within a range of –20° C. to 200° C. or the boiling point of the solvent used.

The molar ratio of the compounds of Formula XI and XII and dehydrating agent used for the reaction can be appropriately set, but it is advantageous to conduct the reaction using them in an equimolar ratio or substantially equimolar ratio.

After completion of the reaction, the reaction solution can be subjected to a normal post treatment such as organic solvent extraction, concentration, etc. to isolate the desired present compound. If necessary, the resulting compound can be further purified by a normal operation such as chromatography, distillation, recrystallization, etc.

Process F

In Formula I, when Z=O, B=O, S, $NR^{14}$, C(=O)O, $R^1=Q_3$, $Q_4$, $Q_7$ or $Q_8$, Process F is employed.

Process F for producing the compound of Formula I comprises reacting a compound represented by Formula XIII:

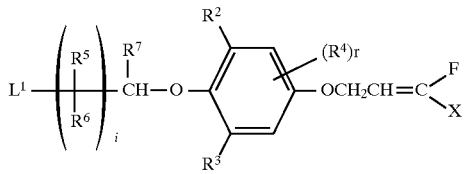

wherein $R^2$, $R^3$, $R^4$, r, $R^5$, $R^6$, $R^7$, X, $L^1$ and i are as defined above with a compound represented by Formula XIV.

$$A-BH \qquad Q_{32}$$

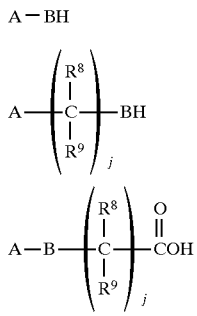  $Q_{42}$

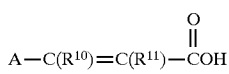  $Q_{72}$

OR $$A-C(R^{10})=C(R^{11})-\overset{O}{\overset{\|}{C}}OH \qquad Q_{82}$$

wherein $R^8$, $R^9$, $R^{10}$, $R^{11}$, A, B and j are as defined above.

It is preferred that the above reaction is carried out in an inert solvent in the presence of a suitable base.

Examples of the solvent to be used include ketones such as acetone, methyl ethyl ketone, cyclohexanone, etc.; ethers such as 1,2-dimethoxyethane, tetrahydroftiran, dioxane, dialkyl (e.g. $C_1$–$C_4$) ether (e.g. diethyl ether, diisopropyl ether, etc.); polar solvents such as N,N-dimethylformamide, dimethyl sulfoxide, triamide hexamethylphosphate, sulfolane, acetonitrile, nitromethane, etc.; hydrocarbon halides such as dichloromethane, chloroform, 1,2-dichloroethane, chlorobenzene, etc.; hydrocarbons such as toluene, benzene, xylene, etc.; or water, etc. A mixed solvent of these solvents can be optionally used.

Examples of the base used include hydroxides of alkali or alkaline earth metals, such as lithium hydroxide, sodium hydroxide, potassium hydroxide, calcium hydroxide, etc.; carbonates of alkali or alkaline earth metals, such as lithium carbonate, potassium carbonate, sodium carbonate, calcium carbonate, etc.; hydrides of alkali, or alkaline earth metals, such as lithium hydride, sodium hydride, potassium hydride, calcium hydride, etc.; alkali. metal alkoxides (e.g. $C_1$–$C_4$), such as sodium methoxide, sodium ethoxide, potassium tert-butoxide, etc.; and organic bases such as triethylamine, pyridine, etc. A catalyst such as an ammonium salt (e.g. triethylbenzylammonium chloride, etc.) may be optionally added to the reaction system in a proportion of 0.01–1 mol, based on 1 mol of the compound represented by Formula XIV.

The reaction temperature may be normally within a range from –20° C. to the boiling point of the solvent used for the reaction or 150° C., preferably from –5° C. to the boiling point of the solvent used for the reaction or 100° C.

The molar ratio of compounds of formula XIII and XIV and base used for the reaction can be appropriately set, but it is advantageous to conduct the reaction using them in an equimolar ratio or substantially equimolar ratio.

After completion of the reaction, the reaction solution can be subjected to a normal post treatment such as organic solvent extraction, concentration, etc. to isolate the desired present compound. If necessary, the resulting compound can be further purified by a normal operation such as chromatography, distillation, recrystallization, etc.

In Formula I, when Z=O, B=C(=O)$NR^{15}$,$R^1$=$Q_3$ or $Q_4$, Process G is employed.

Process G;

Process G for producing the compound of Formula I comprises reacting an amino compound represented by Formula XV:

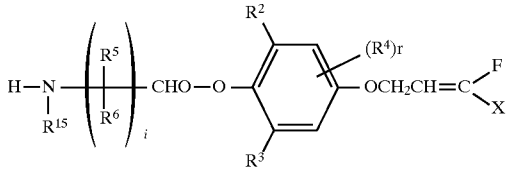

wherein $R^2$, $R^3$, $R^4$, $R^5$, $R^6$, $R^7$, $R^{15}$, r, X and i are as defined above with a carboxylic acid compound represented by Formula XVI.

$$A-\overset{O}{\overset{\|}{C}}OH \qquad Q_{33}$$

OR

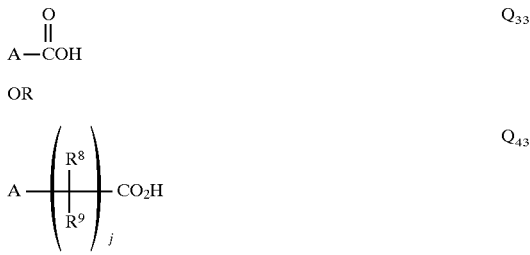  $Q_{43}$ wherein A, $R^8$, $R^9$ and j are as defined above.

It is preferred that the above reaction is carried out in an inert solvent in the presence of a suitable dehydrating agent.

Examples of the dehydrating agent used include dicyclohexylcarbodiimide, dialkyl (e.g, $C_1$–$C_4$) azodicarboxylate (e.g. diethylazodicarboxylate, diisopropylazodicarboxylate, etc.), trialiyl (e.g. $C_1$–$C_{20}$) phosphine or triarylphosphine (e.g. triphenylphosphine, trioctylphosphine, tributyiphosphine, etc.) and the like.

Examples of the solvent used include hydrocarbons such as benzene, xylene, toluene, etc.; ethers such as diethyl ether, diisopropyl ether, tetrahydrofuran, dioxane, etc.; or hydrocarbon halides such as carbon tetrachloride, dichloromethane, chlorobenzene, dichlorobenzene, among others. including mixtures of solvents.

The reaction temperature may be normally within a range from –20° C. to 200° C. or the boiling point of the solvent used.

The molar ratio of compounds of formula XV and XVI and dehydrating agent used for the reaction can be appropriately set, but it is advantageous to conduct the reaction using them in an equimolar ratio or substantially equimolar ratio.

After the completion of the reaction, the reaction solution can be subjected to a normal post treatment such as organic solvent extraction, concentration, etc. to isolate the desired present compound. If necessary, the resulting compound can be further purified by a normal operation such as chromatography, distillation, recrystallization, etc.

In case of the compound having an asymmetric atom, the present compound includes respective optically active isomers having a biological activity (e.g. (+) isomer, (–) isomer, etc.) and compounds containing the isomers in any ratio. In case of the compound having geometric isomerism, the present compound includes respective optically active isomers having a biological activity (e.g. cis-isomer, trans-isomer) and their compounds having any ratio.
Hereinafter, embodiments of the present compound will be shown in Formula XVII to XXI (substituent $R^1$ represents the same one as that described in Table 1 to Table 20), but the present compound is not limited thereto.
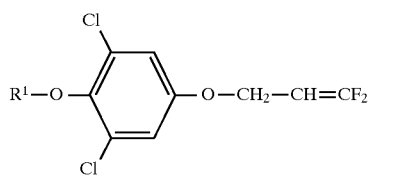
Formula XVII
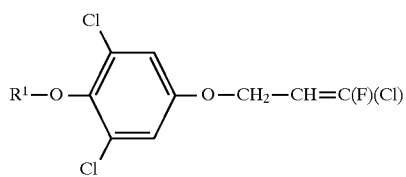
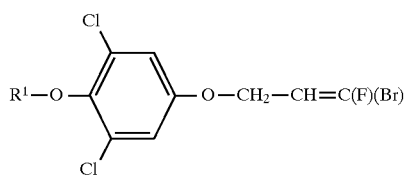
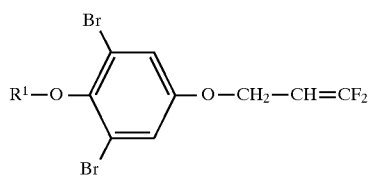
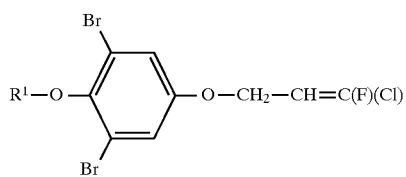
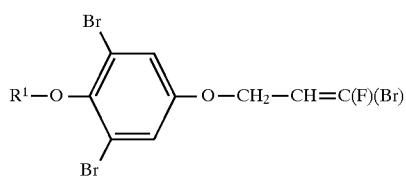
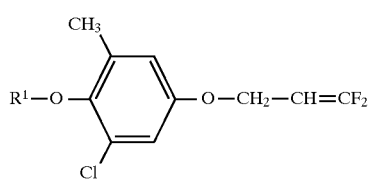
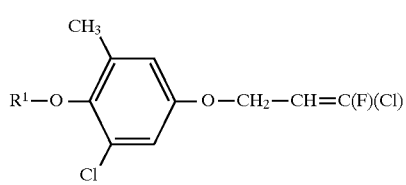
-continued
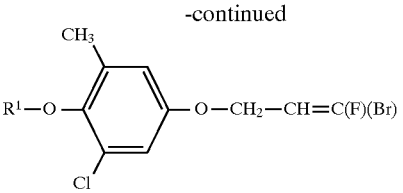
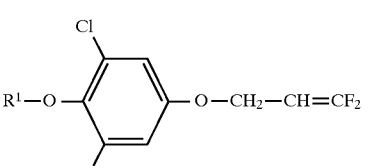
Formula XVIII
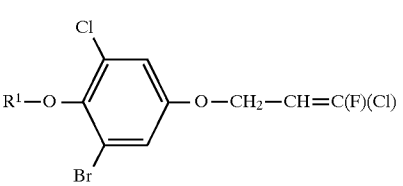
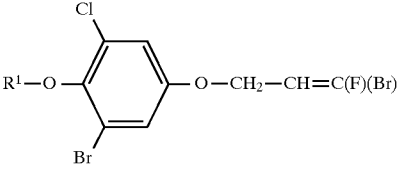
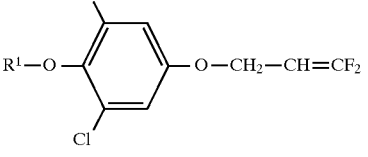
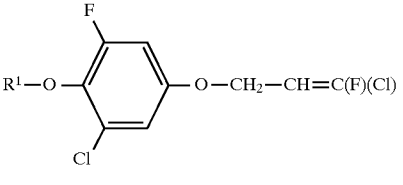
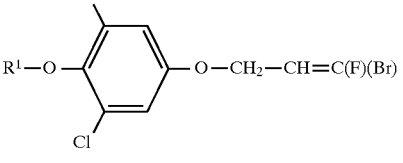
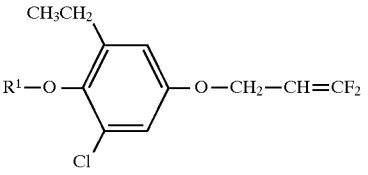
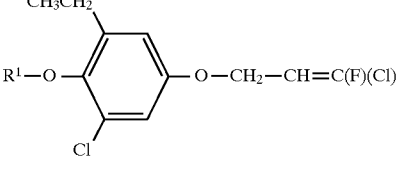

-continued
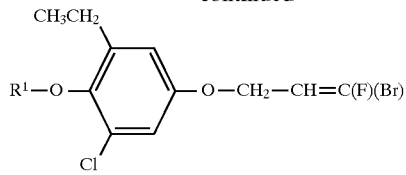
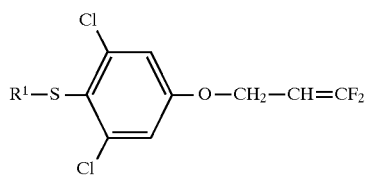
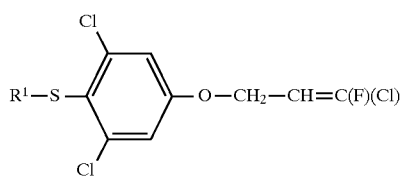
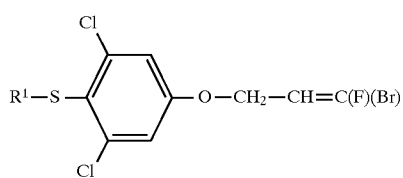
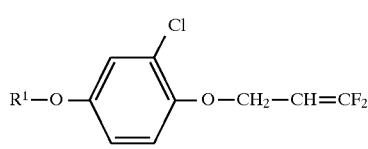
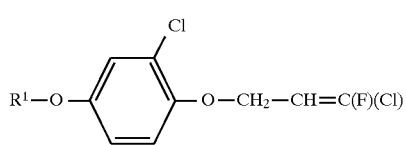
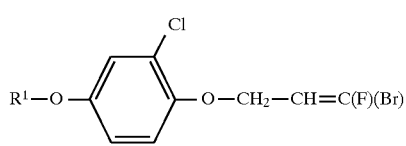
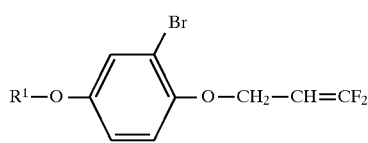
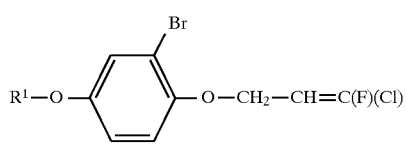
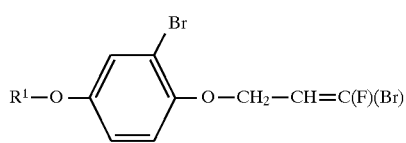
-continued
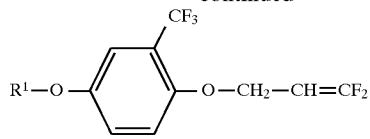
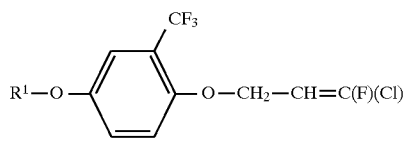
Formula XIX
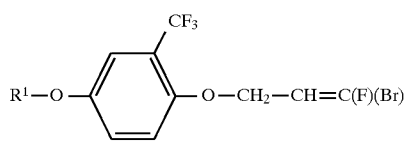
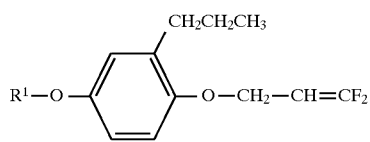
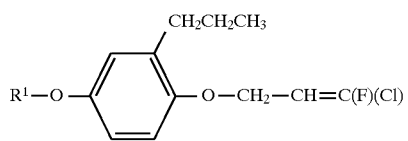
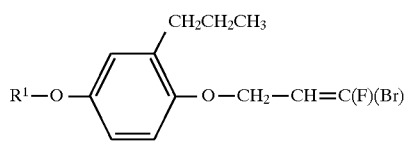
Formula XX
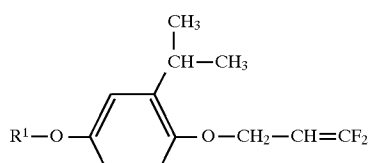
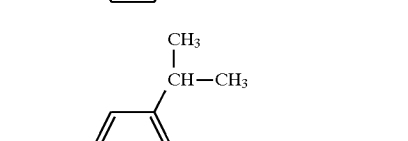
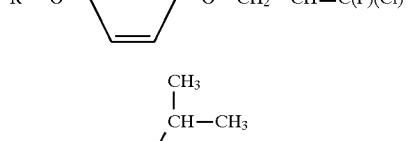
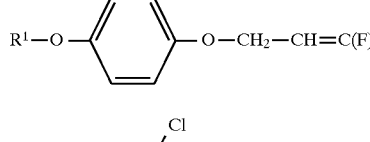

-continued
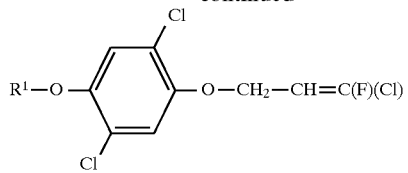
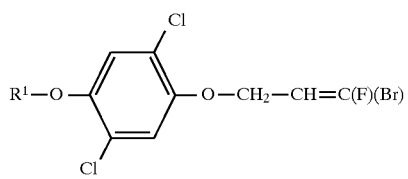
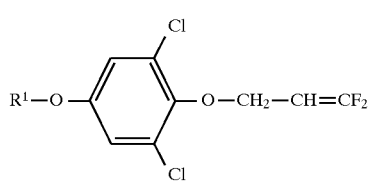
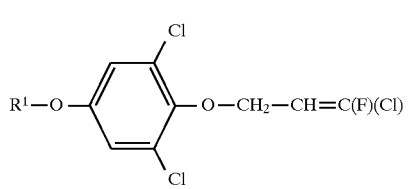
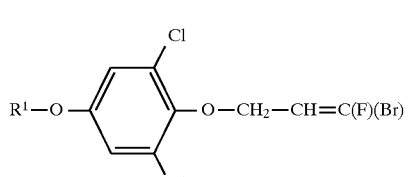
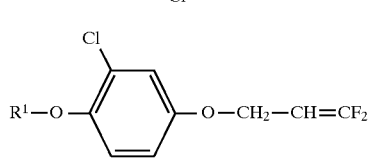
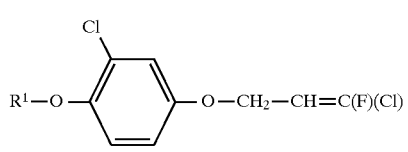
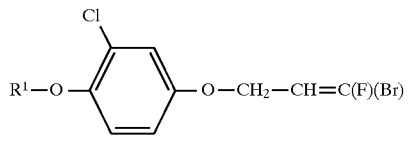
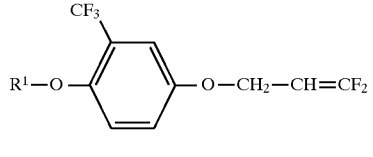
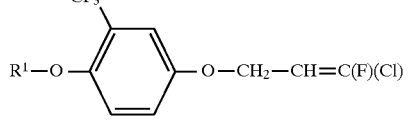
Formula XXI
-continued
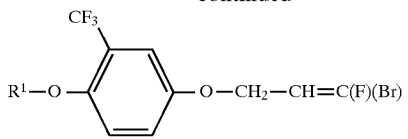
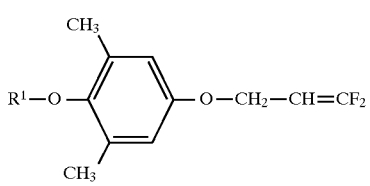
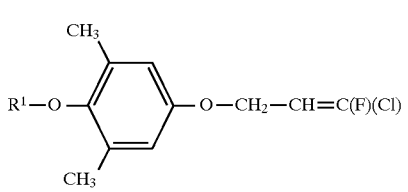
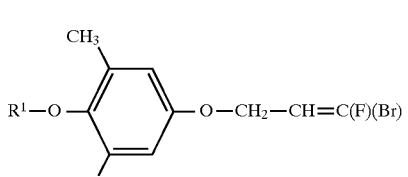
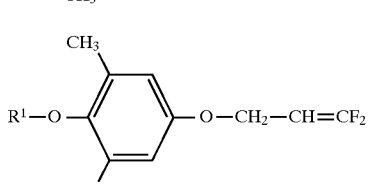
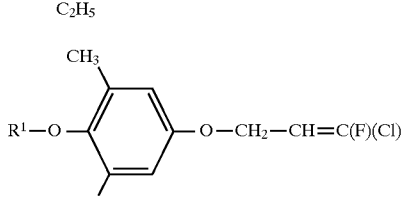
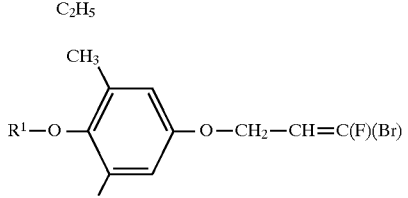
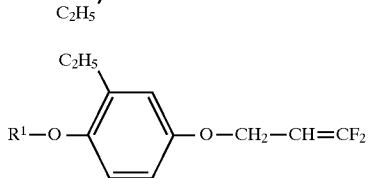
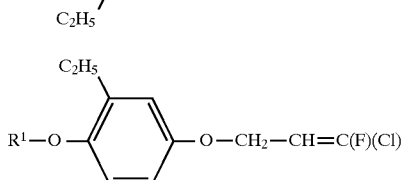

-continued

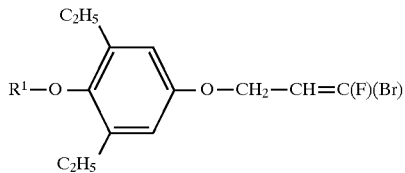

TABLE 1

| R¹ | R¹ |
|---|---|
| CH₃ | CH₃(CH₂)₆CH(CH₃) |
| C₂H₅ | CH₃(CH₂)₇CH₂ |
| CH₃CH₂CH₂ | CH₃(CH₂)₈CH₂ |
| (CH₃)₂CH | CF₃ |
| CH₃(CH₂)₂CH₂ | CHF₂ |
| (CH₃)₂CHCH₂ | CF₂Br |
| CH₃CH₂CH(CH₃) | CF₃CH₂ |
| (CH₃)₃C | CF₃CF₂ |
| CH₃(CH₂)₃CH₂ | FCH₂CH₂ |
| (CH₃)₂CHCH₂CH₂ | ClCH₂CH₂ |
| (CH₃)₃CCH₂ | BrCH₂CH₂ |
| CH₃(CH₂)₂CH(CH₃) | ICH₂CH₂ |
| CH₃CH₂C(CH₃)₂ | CHCl₂CH₂ |
| CH₃CH₂CH(CH₃)CH₂ | CF₂BrCF₂ |
| (CH₃)₂CHCH(CH₃) | CHF₂CF₂ |
| (C₂H₅)₂CH | CHFClCF₂ |
| CH₃(CH₂)₄CH₂ | CF₂BrCHF |
| (CH₃)₂CH(CH₂)₂CH₂ | CCl₃CH₂ |
| CH₃(CH₂)₃CH(CH₃) | CBr₃CH₂ |
| (C₂H₅)₂CHCH₂ | FCH₂CH₂CH₂ |
| CH₃(CH₂)₅CH₂ | ClCH₂CH₂CH₂ |
| CH₃(CH₂)₆CH₂ | BrCH₂CH₂CH₂ |
| CH₃(CH₂)₅CH(CH₃) | ICH₂CH₂CH₂ |

TABLE 2

| | |
|---|---|
| CF₃CH₂CH₂ | CHF₂(CF₂)₃CH₂ |
| CF₃CF₂CH₂ | CH₂=CH |
| CF₃CHFCF₂ | CH₂=CHCH₂ |
| CH₃CHClCH₂ | CH₃CH=CHCH₂ |
| CH₂BrCHBrCH₂ | CH₂=CHCH₂CH₂ |
| CHF₂CF₂CH₂ | CH₂=CHCH(CH₃) |
| CH₂ClCH(CH₃) | CH₂=C(CH₃)CH₂ |
| CH₂BrCH(CH₃) | CH₃CH₂CH=CHCH₂ |
| (CH₂F)₂CH | CH₃CH=CHCH(CH₃) |
| (CH₂Cl)₂CH | CH₃CH=C(CH₃)CH₂ |
| (CH₂Br)₂CH | (CH₃)₂C=CHCH₂ |
| (CF₃)₂CH | CH₂=CHCH(C₂H₅) |
| FCH₂(CH₂)₂CH₂ | CH₂=C(C₂H₅)CH₂ |
| ClCH₂(CH₂)₂CH₂ | CH₂=CHCH₂CH(CH₃) |
| BrCH₂(CH₂)₂CH₂ | CH₂=CHCH(CH₃)CH₂ |
| ICH₂(CH₂)₂CH₂ | CH₂=C(CH₃)CH₂CH₂ |
| CH₃CH(CH₂Br)CH₂ | CH₃(CH₂)₂CH=CHCH₂ |
| CF₃CHFCF₂ | CH₃CH₂CH=CHCH₂CH₃ |
| CH₂BrCH₂CH(CH₂Br) | CH₃CH=CH(CH₂)₂CH₃ |
| (CH₃)₂CClCH₂ | CH₂=CH(CH₂)₂CH₃ |
| FCH₂(CH₂)₃CH₂ | CH₃CH₂CH=C(CH₃)CH₂ |
| ClCH₂(CH₂)₃CH₂ | (CH₃)₂C=CHCH(CH₃) |
| BrCH₂(CH₂)₃CH₂ | CH₂=CH(CH₂)₂CH(CH₃) |
| ICH₂(CH₂)₃CH₂ | CH₃CH=CHCH(C₂H₅) |
| CH₂ClC(CH₃)₂CH₂ | CH₃CH=C(C₂H₅)CH₂ |
| CH₂BrC(CH₃)₂CH₂ | CH₂=CHCH(CH₂CH₂CH₃) |

TABLE 3

| | |
|---|---|
| CH₂=C(CH(CH₃)₂)CH₂ | CCl₂=CHCH₂CH₂ |
| CH₃(CH₂)₃CH=CHCH₂ | CBr₂=CHCH₂CH₂ |
| (CH₂=CHCH₂)₂CH | CCl₂=CH(CH₂)₃CH₂ |
| CH₃(CH₂)₃CH₂CH(CH=CH₂) | CH≡CCH₂ |
| (CH₃)₂C=CH(CH₂)₂— | CH₃C≡CCH₂ |
| CH(CH₃) | CH≡CCH₂CH₂ |
| CH₃(CH₂)₄CH=CHCH₂CH₂ | CH≡CCH(CH₃) |
| CH₃(CH₂)₅CH=CHCH₂CH₂ | CH₃CH₂C≡CCH₂ |
| (CH₃)₂C=CH(CH₂)₂— | CH₃C≡CCH₂CH₂ |
| CH(CH₃)CH₂CH₂ | CH≡C(CH₂)₂CH₂ |
| CHCl=CH₂ | CH≡CCH₂CH(CH₃) |
| CCl₂=CH₂ | CH≡CCH(CH₃)CH₂ |
| CHCl=CHCH₂ | CH≡CCH(C₂H₅) |
| CHBr=CHCH₂ | CH₃(CH₂)₂C≡CCH₂ |
| CH₂=CClCH₂ | CH₃CH₂C≡CCH₂CH₂ |
| CF₂=CHCH₂ | CH₃(CH₂)₃C≡CCH₂ |
| CHCl=CClCH₂ | CH₃(CH₂)₃C≡CCH₂CH₂ |
| CHBr=CBrCH₂ | CH₃(CH₂)₄CH(C≡CH) |
| CH₃CCl=CHCH₂ | CH₃(CH₂)₄C≡CCH₂CH₂ |
| CH₂ClCH=CHCH₂ | CH≡C(CH₂)₃CH₂ |
| CF₃CH=CHCH₂ | ClC≡CCH₂ |
| CH₂=C(CH₂Cl)CH₂ | BrC≡CCH₂ |
| CF₃CCl=CHCH₂ | CH₂ClC≡CCH₂ |
| CF₂BrCF=CHCH₂ | ClC≡CCH(CH₃) |
| CF₃CF=CHCH₂ | BrC≡CCH(CH₃) |

TABLE 4

| | |
|---|---|
| ClC≡CCH₂CH₂ | CH₃CH₂OCH₂CH(CH₃) |
| BrC≡CCH₂CH₂ | CH₃OCH(C₂H₅)CH₂ |
| ClC≡C(CH₂)₂CH₂ | CH₃OCH₂CH(C₂H₅) |
| BrC≡C(CH₂)₂CH₂ | CH₃CH₂O(CH₂)₂CH₂ |
| ClC≡CCH(CH₃)CH₂ | CH₃OCH(CH₃)CH₂CH₂ |
| BrC≡CCH(CH₃)CH₂ | CH₃OCH₂CH(CH₃)CH₂ |
| ClC≡CCH₂CH(CH₃) | CH₃O(CH₂)₂CH(CH₃) |
| BrC≡CCH₂CH(CH₃) | CH₃(CH₂)₃OCH₂CH₂ |
| ClC≡CCH(C₂H₅) | CH₃OC(CH₃)₂CH₂CH₂ |
| BrC≡CCH(C₂H₅) | CH₃(CH₂)₃(OCH₂CH(CH₂)) |
| CH₃OCH₂ | CH₃SCH₂ |
| CH₃CH₂OCH₂ | CH₃CH₂SCH₂ |
| CH₃CH(OCH₃) | CH₃CH(SCH₃) |
| CH₃OCH₂CH₂ | CH₃SCH₂CH₂ |
| CH₃(CH₂)₂OCH₂ | CH₃(CH₂SCH₂ |
| (CH₃)₂CHOCH₂ | (CH₃)₂CHSCH₂ |
| CH₃CH₂OCH(CH₃) | CH₃CH₂SCH(CH₃) |
| CH₃CH₂OCH₂CH₂ | CH₃CH₂SCH₂CH₂ |
| CH₃OCH(CH₃)CH₂ | CH₃SCH(CH₃)CH₂ |
| CH₃OCH₂CH(CH₃) | CH₃SCH₂CH(CH₃) |
| CH₃O(CH₂)₂CH₂ | CH₃S(CH₂)₃CH₂ |
| CH₃CH₂CH(OCH₃) | CH₃CH₂(SCH₃) |
| CH₃(CH₂)₂OCH₂CH₂ | CH₃(CH₂)₂SCH₂CH₂ |
| (CH₃)₂CHOCH₂CH₂ | (CH₃)₂CHSCH₂CH₂ |
| CH₃CH₂OCH(CH₃)CH₂ | CH₃CH₂SCH(CH₃)CH₂ |

TABLE 5

| | |
|---|---|
| CH₃CH₂SCH₂CH(CH₃) | 2-Isobutoxycyclopentyl |
| CH₃SCH(C₂H₅)CH₂ | 2-sec-Butoxycyclopentyl |
| CH₃SCH₂CH(C₂H₅) | 2-tert-Butoxycyclopentyl |
| CH₃CH₂S(CH₂)₂CH₂ | Cyclohexyl |
| CH₃SCH(CH₃)CH₂CH₂ | 2-Methylcyclohexyl |
| CH₃SCH₂CH(CH₃)CH₂ | 3-Methylcyclohexyl |
| CH₃S(CH₂)₂CH(CH₃) | 4-Methylcyclohexyl |
| CH₃S(CH₂)₃CH₂ | 2-Ethylcyclohexyl |
| CH₃SCH(CH₃)CH(CH₃) | 4-Ethylcyclohexyl |
| (CH₃)₃CSCH₂CH₂ | 2,3-Dimethylcyclohexyl |
| (CH₃)₂CHCH₂SCH₂CH₂ | 3,4-Dimethylcyclohexyl |
| CH₃CH₂CH(CH₃)SCH₂CH₂ | 3,5-Dimethylcyclohexyl |
| (CH₃)₃CS(CH₂)₂CH₂ | 3,3,5,5-Tetramethylcyclohexyl |
| (CH₃)₂CHCH₂S(CH₂)₂CH₂ | 3-Methoxycyclohexyl |
| CH₃CH₂CH(CH₃)S(CH₂)₂CH₂ | 3-Ethyloxycyclohexyl |
| Cyclopropyl | 3-n-Propoxycyclohexyl |
| Cyclobutyl | 3-Isopropoxycyclohexyl |
| Cyclopentyl | 3-n-Butoxycyclohexyl |
| 2-Methylcyclopentyl | 3-Isobutoxycyclohexyl |
| 3-Methylcyclopentyl | 3-sec-Butoxycyclohexyl |
| 2-Methoxycyclopentyl | 3-tert-Butoxycyclohexyl |
| 2-Ethoxycyclopentyl | 4-Methoxycyclohexyl |

TABLE 5-continued

| | |
|---|---|
| 2-n-Propoxycyclopentyl | 4-Ethoxycyclohexyl |
| 2-Isopropoxycyclopentyl | 4-n-Propoxycyclohexyl |
| 2-n-Butoxycyclopentyl | |

TABLE 6

| | |
|---|---|
| 4-Isopropoxycyclohexyl | 3-(3,3,3,2,2,1-Hexafluoropropoxy)cyclopentyl |
| 4-n-Butoxycyclohexyl | 3-(Trifluoromethoxy)cyclohexyl |
| 4-Isobutoxycyclohexyl | 4-(Trifluoromethoxy)cyclohexyl |
| 4-sec-Butoxycyclohexyl | 3-(Difluoromethoxy)cyclohexyl |
| 4-tert-Butoxycyclohexyl | 4-(Difluoromethoxy)cyclohexyl |
| 3-(Trifluoromethoxy)cyclopentyl | 3-(Bromodifluoromethoxy)cyclohexyl |
| 3-(Difluoromethoxy)cyclopentyl | 4-(Bromodifluoromethoxy)cyclohexyl |
| 3-(Bromodifluoromethoxy)cyclopentyl | 3-(2,2,2-Trifluoroethoxy)cyclohexyl |
| 3-(2,2,2-Trifluoroethoxy)cyclopentyl | 4-(2,2,2-Trifluoroethoxy)cyclohexyl |
| 3-(2,2,2,1,1-Pentafluoroethoxy)cyclopentyl | 3-(2,2,2,1,1-Pentafluoroethoxy)cyclohexyl |
| 3-(2-Chloroethoxy)cyclopentyl | 4-(2,2,2,1,1-Pentafluoroethoxy)cyclohexyl |
| 3-(2-Bromoethoxy)cyclopentyl | 3-(2-Chloroethoxy)cyclohexyl |
| 3-(2-Chloro-1,1,2-trifluoroethoxy)cyclopentyl | 4-(2-Chloroethoxy)cyclohexyl |
| 3-(2-Bromo-1,1,2-trifluoroethoxy)cyclopentyl | |
| 3-(1,1,2,2-Tetrafluoroethoxy)cyclopentyl | |

TABLE 7

| | |
|---|---|
| 3-(2-Bromoethoxy)cyclohexyl | Cyclopentylmethyl |
| 4-(2-Bromoethoxy)cyclohexyl | 2-Cyclopentylethyl |
| 3-(2-Chloro-1,1,2-trifluoroethoxy)cyclohexyl | 3-Cyclopentylpropyl |
| 4-(2-Chloro-1,1,2-trifluoroethoxy)cyclohexyl | Cyclohexylmethyl |
| 3-(2-Bromo-1,1,2-trifluoroethoxy)cyclohexyl | 2-Cyclohexylethyl |
| 4-(2-Bromo-1,1,2-trifluoroethoxy)cyclohexyl | 3-Cyclohexylpropyl |
| 3-(1,1,2,2-Tetrafluoroethoxy)cyclohexyl | 2-Cyclohexenyl |
| 4-(1,1,2,2-Tetrafluoroethoxy)cyclohexyl | 3-Cyclohexenyl |
| 3-(3,3,3,2,2,1-Hexafluoropropoxy)cyclohexyl | 3-Methyl-2-cyclohexenyl |
| 4-(3,3,3,2,2,1-Hexafluoropropoxy)cyclohexyl | 3,5,5-Trimethyl-2-cyclohexenyl |
| Cyclopropylmethyl | 2-Cyclopentenyl |
| (1-Methylcyclopropyl)methyl | 3-Cyclopentenyl |
| (2-Methylcyclopropyl)methyl | 3-Methyl-2-cyclopentenyl |
| 1-Cyclopropylethyl | (3-Cyclohexenyl)methyl |
| 2-(2-Methylcyclopropyl)ethyl | 2-(3-Cyclohexenyl)ethyl |
| Cyclobutylmethyl | (1-Cyclopentenyl)methyl |

TABLE 8

$R^1 = (R^{16})_q$ — phenyl ring with positions 1,2,3,4,5,6

| $(R^{16})_q$ | $(R^{16})_q$ |
|---|---|
| 2-F | 2,3,4,5,6-Cl$_5$ |
| 3-F | 2-Br |
| 4-F | 3-Br |
| 2-Cl | 4-Br |
| 3-Cl | 3,5-Br$_2$ |
| 4-Cl | 2,4-Br$_2$ |
| 2,3-Cl$_2$ | 2-I |
| 2,6-Cl$_2$ | 3-I |
| 3,5-Cl$_2$ | 4-I |
| 2,4-Cl$_2$ | 2-F, 4-Cl |
| 3,4-Cl$_2$ | 3-F, 4-Cl |
| 2,5-Cl$_2$ | 3-Cl, 4-F |
| 2,3,4-Cl$_3$ | 2-Br, 4-F |
| 2,3,6-Cl$_3$ | 2-F, 4-Br |
| 2,4,6-Cl$_3$ | 2-Br, 5-F |
| 2,3,5-Cl$_3$ | 2-Br, 4-Cl |
| 2,4,5-Cl$_3$ | 2-Cl, 4-F |
| 2-Cl, 4-Br | 3-CH(CH$_3$)(CH$_2$)$_2$CH$_3$ |
| 2-Cl, 4-OCH$_3$ | 3-CH(CH$_3$)CH(CH$_3$)$_2$ |
| 3-CH$_3$, 4-Cl | 3-CH(C$_2$H$_5$)$_2$ |
| 2-CH$_3$, 4-F | 3-C(CH$_3$)$_2$CH$_2$CH$_3$ |
| 3-CH$_3$, 4-F | 3-(CH$_2$)$_5$CH$_3$ |
| 2-Cl, 4-CH$_3$ | 3-(CH$_2$)$_6$CH$_3$ |
| 2-Cl, 5-CH$_3$ | 3-(CH$_2$)$_7$CH$_3$ |
| 2-CH$_3$, 4-Cl | 4-CH$_3$ |
| 3-C$_2$H$_5$, 4-Cl | 4-C$_2$H$_5$ |
| 2-Br, 4-CH$_3$ | 4-CH$_2$CH$_2$CH$_3$ |
| 2-CH$_3$, 4-I | 4-CH(CH$_3$)$_2$ |
| 2-Cl, 5-CF$_3$ | 4-(CH$_2$)$_3$CH$_3$ |
| 2,4-Cl$_2$, 3-CH$_3$ | 4-CH(CH$_3$)CH$_2$CH$_3$ |

TABLE 8-continued $$R^1 = (R^{16})_q \text{—[benzene ring with positions 1,2,3,4,5,6]}$$

| $(R^{16})_q$ | $(R^{16})_q$ |
|---|---|
| 4-Cl, 3,5-(CH$_3$)$_2$ | 4-CH$_2$CH(CH$_3$)$_2$ |
| 4-Br, 3,5-(CH$_3$)$_2$ | 4-C(CH$_3$)$_3$ |
| 4-Br, 2,6-(CH$_3$)$_2$ | 4-(CH$_2$)$_4$CH$_3$ |
| 4-Cl, 4,5-(CH$_3$)$_2$ | 4-CH(CH$_3$)(CH$_2$)$_2$CH$_3$ |
| 2-CH(CH$_3$)$_2$, 4-Cl, 5-CH$_3$ | 4-CH(CH$_3$)CH(CH$_3$)$_2$ |
| 3-CH$_3$ | 4-CH(C$_2$H$_5$)$_2$ |
| 3-C$_2$H$_5$ | 4-C(CH$_3$)$_2$CH$_2$CH$_3$ |
| 3-CH(CH$_3$)$_2$ | 4-(CH$_2$)$_5$CH$_3$ |
| 3-C(CH$_3$)$_3$ | 4-(CH$_2$)$_6$CH$_3$ |
| 3-CH$_2$CH$_2$CH$_2$CH$_3$ | 4-(CH$_2$)$_7$CH$_3$ |
| 3-CH(CH$_3$)CH$_2$CH$_3$ | 4-C(CH$_3$)$_2$CH$_2$C(CH$_3$)$_3$ |
| 3-CH$_2$CH(CH$_3$)$_2$ | 2-Cl, 4-C$_2$H$_5$ |
| 3-(CH$_2$)$_4$CH$_3$ | 2-Cl, 4-CH$_2$CH$_2$CH$_3$ |
| 2-Cl, 4-CH(CH$_3$)$_2$ | 4-CF$_3$ |
| 2-Cl, 4-(CH$_2$)$_3$CH$_3$ | 3,5-(CF$_3$)$_2$ |
| 2-Cl, 4-CH(CH$_3$)CH$_2$CH$_3$ | 2,4-(CF$_3$)$_2$ |
| 2-Cl, 4-CH$_2$CH(CH$_3$)$_2$ | 2-F, 4-CF$_3$ |
| 2-Br, 4-CH$_2$CH(CH$_3$)$_2$ | 2-Cl, 4-CF$_3$ |
| 2-Cl, 4-C(CH$_3$)$_3$ | 2,6-Cl$_2$, 4-CF$_3$ |
| 2-Cl, 4-(CH$_2$)$_4$CH$_3$ | 2-CF$_3$, 4-Cl |
| 2-Cl, 4-CH(CH$_3$)(CH$_2$)$_2$CH$_3$ | 2-CF$_3$, 5-Cl |
| 2-Cl, 4-CH(CH$_3$)CH(CH$_3$)$_2$ | 2-Br, 4-CF$_3$ |
| 2-Cl, 4-CH(C$_2$H$_5$)$_2$ | 2-CF$_3$, 4-Br |
| 2-Cl, 4-C(CH$_3$)$_2$CH$_2$CH$_3$ | 2-I, 4-CF$_3$ |
| 2-Br, 4-C$_2$H$_5$ | 2-F, 6-Cl, 4-CF$_3$ |
| 2-Br, 4-(CH$_2$)$_2$CH$_3$ | 2,6-F$_2$, 4-CF$_3$ |
| 2-Br, 4-CH(CH$_3$)$_2$ | 2-CCl$_3$ |
| 2-Br, 4-(CH$_2$)$_3$CH$_3$ | 4-CCl$_3$ |
| 2-Br, 4-CH(CH$_3$)CH$_2$CH$_3$ | 2-CHF$_2$ |
| 2-Br, 4-CH$_2$CH(CH$_3$)$_2$ | 3-CHF$_2$ |
| 2-Br, 4-C(CH$_3$)$_3$ | 4-CHF$_2$ |
| 2-Br, 4-(CH$_2$)$_4$CH$_3$ | 2-CF$_2$Br |
| 2-Br, 4-CH(CH$_3$)(CH$_2$)$_2$CH$_3$ | 3-CF$_2$Br |
| 2-Br, 4-CH(CH$_3$)CH(CH$_3$)$_2$ | 4-CF$_2$Br |
| 2-Br, 4-CH(C$_2$H$_5$)$_2$ | 2-CH$_2$CF$_3$ |
| 2-Br, 4-C(CH$_3$)$_2$CH$_2$CH$_3$ | 4-CH$_2$CF$_3$ |
| 2-CF$_3$ | 3-CH$_2$CH$_2$CF$_3$ |
| 3-CF$_3$ | 4-CH$_2$CH$_2$CF$_2$ |
| 3-CH$_2$CF$_2$CF$_3$ | 4-OCH(CH$_3$)(CH$_2$)$_2$CH$_3$ |
| 4-CH$_2$CF$_2$CF$_3$ | 4-OCH(CH$_3$)CH(CH$_3$)$_2$ |
| 2-OCH$_3$ | 4-OCH(C$_2$H$_5$)$_2$ |
| 3-OCH$_3$ | 3-OC(CH$_3$)$_2$CH$_2$CH$_3$ |
| 3-OC$_2$H$_5$ | 4-OC(CH$_3$)$_2$CH$_2$CH$_3$ |
| 3-OCH$_2$CH$_2$CH$_3$ | 4-O(CH$_2$)$_5$CH$_3$ |
| 3-OCH(CH$_3$)$_2$ | 4-O(CH$_2$)$_6$CH$_3$ |
| 3-O(CH$_2$)$_3$CH$_3$ | 3,5-{C(CH$_3$)$_3$}$_2$ |
| 3-OCH(CH$_3$)CH$_2$CH$_3$ | 3,5-(CH$_3$)$_2$ |
| 3-OCH$_2$CH(CH$_3$)$_2$ | 3-CH$_3$, 5-CH(CH$_3$)$_2$ |
| 3-OC(CH$_3$)$_3$ | 3,4-(CH$_3$)$_2$ |
| 3-O(CH$_2$)$_4$CH$_3$ | 2,4-(CH$_3$)$_2$ |
| 3-OCH(CH$_3$)(CH$_2$)(CH$_2$)$_2$CH$_3$ | 2,5-(CH$_3$)$_2$ |
| 3-OCH(C$_2$H$_5$)$_2$ | 2-CH(CH$_3$)$_2$, 5-CH$_3$ |
| 3-OCH(CH$_3$)CH(CH$_3$)$_2$ | 3-CH$_3$, 4-CH(CH$_3$)$_2$ |
| 3-O(CH$_2$)$_5$CH$_3$ | 3-CH$_3$, 5-CH(CH$_3$) |
| 3-O(CH$_2$)$_6$CH$_3$ | 2-C(CH$_3$)$_3$, 5-CH$_3$ |
| 4-OCH$_3$ | 2-C(CH$_3$)$_3$, 4-CH$_3$ |
| 4-OC$_2$H$_5$ | 2,4-{C(CH$_3$)$_3$}$_2$ |
| 4-OCH$_2$CH$_2$CH$_3$ | 2,3,5-(CH$_3$)$_3$ |
| 4-OCH(CH$_3$)$_2$ | 3,4,5-(CH$_3$)$_3$ |
| 4-(CH$_2$)$_3$CH$_3$ | 2,4,6-(CH$_3$)$_3$ |
| 4-OCH(CH$_3$)CH$_2$CH$_3$ | 2,3-(OCH$_3$)$_2$ |
| 4-OCH$_2$CH(CH$_3$)$_2$ | 3,5-(OCH$_3$)$_2$ |
| 4-OC(CH$_3$)$_3$ | 2-OCH$_3$, 4-CH$_3$ |
| 4-O(CH$_2$)$_4$CH$_3$ | 3,4-(OCH$_3$)$_2$ |
| 3-C$_2$H$_5$, 4-OCH$_3$ | 2-Br, 4-OCH(CH$_3$)(CH$_2$)$_2$CH$_3$ |
| 3,4,5-(OCH$_3$)$_3$ | 2-Br, 4-OCH(CH$_3$)CH(CH$_3$)$_2$ |
| 3-Cl, 5-OCH$_3$ | 2-Br, 4-OCH(C$_2$H$_5$)$_2$ |
| 2-Cl, 4-OC$_2$H$_5$ | 2-Br, 4-OC(CH$_3$)$_2$CH$_2$CH$_3$ |
| 2-Cl, 4-OCH$_2$CH$_2$CH$_3$ | 3-OCH$_3$, 5-OC$_2$H$_5$ |
| 2-Cl, 4-OCH(CH$_3$)$_2$ | 3,5-(OC$_2$H$_5$)$_2$ |

TABLE 8-continued $$R^1 = (R^{16})_q \text{—[benzene ring with positions 1,2,3,4,5,6]}$$

| $(R^{16})_q$ | $(R^{16})_q$ |
|---|---|
| 2-Cl, 4-O(CH$_2$)$_3$CH$_3$ | 3,5-(OCH(CH$_3$)$_2$)$_2$ |
| 2-Cl, 4-OCH(CH$_3$)CH$_2$CH$_3$ | 3-OCH$_3$, 5-OCH(CH$_3$)$_2$ |
| 2-Cl, 4-OCH$_2$CH(CH$_3$)$_2$ | 3-OC$_2$H$_5$, 5-OCH(CH$_3$)$_2$ |
| 2-Cl, 4-OC(CH$_3$)$_3$ | 2-CH$_3$, 3-OCH$_3$ |
| 2-Cl, 4-O(CH$_2$)$_4$CH$_3$ | 2-CH$_3$, 3-OC$_2$H$_5$ |
| 2-Cl, 4-OCH(CH$_3$)(CH$_2$)$_2$CH$_3$ | 3-CH$_3$, 3-OCH(CH$_3$)$_2$ |
| 2-Cl, 4-OCH(CH$_3$)CH(CH$_3$)$_2$ | 2-CH$_3$, 3-OCH(CH$_3$)$_2$ |
| 2-Cl, 4-OCH$_2$CH(C$_2$H$_5$)$_2$ | 3-OCH$_3$, 4-Cl |
| 2-Cl, 4-OC(CH$_3$)$_2$CH$_2$CH$_3$ | 3-OCH$_3$, 4-Br |
| 2-Br, 4-OCH$_3$ | 3-OC$_2$H$_5$, 4-Cl |
| 2-Br, 4-OC$_2$H$_5$ | 3-OC$_2$H$_5$, 4-Br |
| 2-Br, 4-O(CH$_2$)$_2$CH$_3$ | 3-OCH(CH$_3$)$_2$, 4-Cl |
| 2-Br, 4-OCH(CH$_3$)$_2$ | 3-OCH(CH$_3$)$_2$, 4-Br |
| 2-Br, 4-O(CH$_2$)$_3$CH$_3$ | 3-CH$_3$, 5-OCH$_3$ |
| 2-Br, 4-OCH(CH$_3$)CH$_2$CH$_3$ | 3-CH$_3$, 5-OC$_2$H$_5$ |
| 2-Br, 4-OCH$_2$CH(CH$_3$)$_2$ | 3-CH$_3$, 5-OCH(CH$_3$)$_2$ |
| 2-Br, 4-OC(CH$_3$)$_3$ | 2-CH$_3$, 4-OCH$_3$ |
| 2-Br, 4-O(CH$_2$)$_4$CH$_3$ | 2-CH$_3$, 4-OC$_2$H$_5$ |
| 2-CH$_3$, 4-OCH(CH$_3$)$_2$ | 2-Cl, 4-OCF$_3$ |
| 2,3-(CH$_3$)$_2$, 4-OCH$_3$ | 2-Cl, 4-OCHF$_2$ |
| 2,3-(CH$_3$)$_2$, 4-OC$_2$H$_5$ | 2-Cl, 4-OCF$_2$Br |
| 2,3-(CH$_3$)$_2$, 4-OCH(CH$_3$)$_2$ | 2-Cl, 4-OCH$_2$CF$_3$ |
| 2-OCF$_3$ | 2-Cl, 4-OCH$_2$CH$_2$CF$_3$ |
| 3-OCF$_3$ | 2-Cl, 4-OCH$_2$CF$_2$CF$_3$ |
| 4-OCF$_3$ | 2-Cl, 4-OCF$_2$CF$_2$H |
| 2-OCHF$_2$ | 2-Cl, 4-OCF$_2$CFHCl |
| 3-OCHF$_2$ | 2-Cl, 4-OCF$_2$CFHBr |
| 4-OCHF$_2$ | 3-OCF$_2$CF$_3$ |
| 2-OCF$_2$Br | 4-OCF$_2$CF$_3$ |
| 3-OCF$_2$Br | 2-SCH$_3$ |
| 4-OCF$_2$Br | 3-SCH$_3$ |
| 3-OCH$_2$CF$_3$ | 4-SCH$_3$ |
| 4-OCH$_2$CF$_3$ | 2-CH$_3$, 4-SCH$_3$ |
| 3-OCF$_2$CFHCl | 2-CH$_3$, 4-SCH$_3$ |
| 4-OCF$_2$CFHCl | 2-SC$_2$H$_5$ |
| 3-OCF$_2$CFHBr | 3-SC$_2$H$_5$ |
| 4-OCF$_2$CFHBr | 3-SCH$_2$CH$_3$ |
| 3-OCF$_2$CF$_2$H | 3-SCH(CH$_3$)$_2$ |
| 4-OCF$_2$CF$_2$H | 4-SC$_2$H$_5$ |
| 3-OCH$_2$CH$_2$CF$_3$ | 4-S(CH$_2$)$_2$CH$_3$ |
| 4-OCH$_2$CH$_2$CF$_3$ | 4-SCH(CH$_3$)$_2$ |
| 3-OCH$_2$CF$_2$CF$_3$ | 2-SCF$_3$ |
| 4-OCH$_2$CF$_2$CF$_3$ | 3-SCF$_3$ |
| 4-SCF$_3$ | 4-OCH$_2$CH=CHCH$_3$ |
| 3-SCHF$_2$ | 3-OCH$_2$CH=C(CH$_3$)$_2$ |
| 4-SCHF$_3$ | 4-OCH$_2$CH=C(CH$_3$)$_2$ |
| 3-SCF$_2$Br | 3-OCH$_2$C(CH$_3$)=CHCH$_3$ |
| 4-SCF$_2$Br | 4-OCH$_2$C(CH$_3$)=CHCH$_3$ |
| 3-SCH$_2$CF$_3$ | 3-OCH$_2$CH=CHC$_2$H$_5$ |
| 4-SCH$_2$CF$_3$ | 4-OCH$_2$CH=CHC$_2$H$_5$ |
| 3-SCF$_2$CFHCl | 3-OCH$_2$CH=CH(CH$_2$)$_2$CH$_3$ |
| 4-SCF$_2$CFHCl | 4-OCH$_2$CH=CH(CH$_2$)$_2$CH$_3$ |
| 3-SCF$_2$CFHBr | 3-OCH$_2$CH=CCl$_2$ |
| 4-SCF$_2$CFHBr | 4-OCH$_2$CH=CCl$_2$ |
| 4-SCF$_2$CF$_2$H | 3-OCH$_2$CH=CBr$_2$ |
| 3-SCF$_2$CF$_2$H | 4-OCH$_2$CH=CBr$_2$ |
| 3-SCH$_2$CF$_2$CF$_3$ | 3-OCH$_2$C(Cl)=CH(Cl) |
| 4-SCH$_2$CF$_2$CF$_3$ | 4-OCH$_2$C(Cl)=CH(Cl) |
| 3-SCH$_2$CH$_2$CF$_3$ | 3-OCH$_2$C(Br)=CH(Br) |
| 4-SCH$_2$CH$_2$CF$_3$ | 4-OCH$_2$C(Br)=CH(Br) |
| 3-SCF$_2$CF$_3$ | 3-OCH$_2$C(Cl)=CH$_2$ |
| 4-SCF$_2$CF$_3$ | 4-OCH$_2$C(Cl)=CH$_2$ |
| 3-CH$_3$, 4-SCH$_3$ | 3-OCH$_2$CH=CH(Cl) |
| 3-OCH$_2$CH=CH$_2$ | 4-OCH$_2$CH=CH(Cl) |
| 4-OCH$_2$CH=CH$_2$ | 3-OCH$_2$C(Br)=CH$_2$ |
| 3-OCH(CH$_3$)CH=CH$_2$ | 4-OCH$_2$C(Br)=CH$_2$ |
| 4-OCH(CH$_3$)CH=CH$_2$ | 3-OCH$_2$CH=CClCH$_3$ |
| 3-OCH$_2$CH=CHCH$_3$ | 4-OCH$_2$CH=CClCH$_3$ |
| 3-Cyclopentyl | 3-Phenoxy |
| 4-Cyclopentyl | 4-Phenoxy |

TABLE 8-continued $$R^1 = (R^{16})_q \text{ on phenyl ring (positions 2,3,4,5,6; attached at 1)}$$

| $(R^{16})_q$ | $(R^{16})_q$ |
|---|---|
| 3-Cyclohexyl | 2-Cl, 4-cyclopentyl |
| 4-Cyclohexyl | 2-Cl, 4-cyclohexyl |
| 3-Phenyl | 2-Cl, 4-phenyl |
| 4-Phenyl | 2-Cl, 4-cyclohexyl |
| 3-O-cyclopentyl | 2-Cl, 4-O-cyclopentyl |
| 4-O-cyclopentyl | 2-Cl, 4-O-cyclohexyl |
| 3-O-cyclohexyl | 2-Cl, 4-phenoxy |
| 4-O-cyclohexyl | |

TABLE 9

$$R^1 = (R^{16})_q \text{ on phenyl ring with } CH_2 \text{ at position 1}$$

| $(R^{16})_q$ | $(R^{16})_q$ |
|---|---|
| H | 3-OCH$_2$C≡CBr |
| 2-F | 3-Cyclopentyl |
| 2-Cl | 3-Cyclohexyl |
| 3-F | 3-(3-Cyclopentenyl) |
| 3-Cl | 3-(2-Cyclopentenyl) |
| 3-CH$_3$ | 3-(3-Cyclohexenyl) |
| 3-CF$_3$ | 3-(2-Cyclohexenyl) |
| 3-OCH$_3$ | 3-Cyclopropyloxy |
| 3-OCF$_3$ | 3-Cyclobutyloxy |
| 3-SCH$_3$ | 3-Cyclopentyloxy |
| 3-SC$_2$H$_5$ | 3-Cyclohexyloxy |
| 3-SCF$_2$CHF$_2$ | 3-(3-Cyclopentenyl)oxy |
| 3-OCH$_2$CH=CH$_2$ | 3-(2-Cyclopentenyl)oxy |
| 3-OCH$_2$CH=CCl$_2$ | 3-(3-Cyclohexenyl)oxy |
| 3-OCH$_2$CH=CBr$_2$ | 3-(2-Cyclohexenyl)oxy |
| 3-OCH$_2$C≡CH | 3-OC$_6$H$_5$ |
| 3-OCH$_2$C≡CCl | 3-(o-CH$_3$C$_6$H$_4$O) |
| 3-(m-CH$_3$C$_6$H$_4$O) | 3-(p-FC$_6$H$_4$CH$_2$O) |
| 3-(p-CH$_3$C$_6$H$_4$O) | 3-(o-BrC$_6$H$_4$CH$_2$O) |
| 3-(o-ClC$_6$H$_4$O) | 3-(m-BrC$_6$H$_4$CH$_2$O) |
| 3-(m-ClC$_6$H$_4$O) | 3-(p-BrC$_6$H$_4$CH$_2$O) |
| 3-(p-ClC$_6$H$_4$O) | 3-(o-CH$_3$C$_6$H$_4$CH$_2$O) |
| 3-(o-FC$_6$H$_4$O) | 3-(m-CH$_3$C$_6$H$_4$CH$_2$O) |
| 3-(m-FC$_6$H$_4$O) | 3-(p-CH$_3$C$_6$H$_4$CH$_2$O) |
| 3-(p-FC$_6$H$_4$O) | 3-(o-CF$_3$C$_6$H$_4$CH$_2$O) |
| 3-(o-CF$_3$C$_6$H$_4$O) | 3-(m-CF$_3$C$_6$H$_4$CH$_2$O) |
| 3-(m-CF$_3$C$_6$H$_4$O) | 3-(p-CF$_3$C$_6$H$_4$CH$_2$O) |
| 3-(p-CF$_3$C$_6$H$_4$O) | 3-CH$_2$C$_6$H$_5$ |
| 3-(m-(CH$_3$)$_3$CC$_6$H$_4$O) | 4-F |
| 3-(p-(CH$_3$)$_3$CC$_6$H$_4$O) | 4-Cl |
| 3-(m-CH$_3$OC$_6$H$_4$O) | 4-CH$_3$ |
| 3-(p-CH$_3$OC$_6$H$_4$O) | 4-OCH$_3$ |
| 3-(3,4-Cl$_2$C$_6$H$_3$O) | 4-CF$_3$ |
| 3-(3,5-Cl$_2$C$_6$H$_3$O) | 4-OCF$_3$ |
| 3-(m-CF$_3$OC$_6$H$_4$O) | 4-SCH$_3$ |
| 3-(p-CF$_3$OC$_6$H$_4$O) | 4-OCH$_2$CH=CH$_2$ |
| 3-C$_6$H$_5$ | 4-OCH$_2$CH=CCl$_2$ |
| 3-CH$_2$C$_6$H$_3$ | 4-OCH$_2$CH=CBr$_2$ |
| 3-(o-ClC$_6$H$_4$CH$_2$O) | 4-OCH$_2$C≡CH |
| 3-(m-ClC$_6$H$_4$CH$_2$O) | 4-OCH$_2$C≡CCl |
| 3-(p-ClC$_6$H$_4$CH$_2$O) | 4-OCH$_2$C≡CBr |
| 3-(o-FC$_6$H$_4$CH$_2$O) | 4-Cyclopentyl |
| 3-(m-FC$_6$H$_4$CH$_2$O) | |

TABLE 9-continued $$R^1 = (R^{16})_q \text{ on phenyl ring with } CH_2 \text{ at position 1}$$

| $(R^{16})_q$ | $(R^{16})_q$ |
|---|---|
| 4-Cyclohexyl | 4-(p-CH$_3$C$_6$H$_4$O) |
| 4-(3-Cyclopentenyl) | 4-(o-CF$_3$C$_6$H$_4$O) |
| 4-(2-Cyclopentenyl) | 4-(m-CF$_3$C$_6$H$_4$O) |
| 4-(3-Cyclohexenyl) | 4-(p-CF$_3$C$_6$H$_4$O) |
| 4-(2-Cyclohexenyl) | 4-(m-(CH$_3$)$_3$CC$_6$H$_4$O) |
| 4-Cyclopropyloxy | 4-(p-(CH$_3$)$_3$CC$_6$H$_4$O) |
| 4-Cyclobutyloxy | 4-(m-CH$_3$OC$_6$H$_4$O) |
| 4-Cyclopentyloxy | 4-(p-CH$_3$OC$_6$H$_4$O) |
| 4-Cyclohexyloxy | 4-(m-CF$_3$OC$_6$H$_4$O) |
| 4-(3-Cyclopentenyl)oxy | 4-(p-CF$_3$OC$_6$H$_4$O) |
| 4-(2-Cyclopentenyl)oxy | 4-CH$_2$C$_6$H$_5$ |
| 4-(3-Cyclohexenyl)oxy | 4-OCH$_2$C$_6$H$_5$ |
| 4-(1-Cyclohexenyl)oxy | 4-(o-ClC$_6$H$_4$CH$_2$O) |
| 4-(2-Cyclohexenyl) | 4-(m-ClC$_6$H$_4$CH$_2$O) |
| 4-C$_6$H$_5$ | 4-(p-ClC$_6$H$_4$CH$_2$O) |
| 4-OC$_6$H$_5$ | 4-(o-FC$_6$H$_4$CH$_2$O) |
| 4-(o-ClC$_6$H$_4$O) | 4-(m-FC$_6$H$_4$CH$_2$O) |
| 4-(m-ClC$_6$H$_4$O) | 4-(P-FC$_6$H$_4$CH$_2$O) |
| 4-(p-ClC$_6$H$_4$O) | 4-(o-BrC$_6$H$_4$CH$_2$O) |
| 4-(o-FC$_6$H$_4$O) | 4-(m-BrC$_6$H$_4$CH$_2$O) |
| 4-(m-FC$_6$H$_4$O) | 4-(p-BrC$_6$H$_4$CH$_2$O) |
| 4-(p-FC$_6$H$_4$O) | 4-(o-CH$_3$C$_6$H$_4$CH$_2$O) |
| 4-(o-CH$_3$C$_6$H$_4$O) | 4-(m-CH$_3$C$_6$H$_4$CH$_2$O) |
| 4-(m-CH$_3$C$_6$H$_4$O) | 4-(P-CH$_3$C$_6$H$_4$CH$_2$O) |
| 4-(o-CF$_3$C$_6$H$_4$CH$_2$O) | 4-Br, 3-OCH$_2$C$_6$H$_5$ |
| 4-(m-CF$_3$C$_6$H$_4$CH$_2$O) | 4-CH$_3$, 3-OC$_6$H$_5$ |
| 4-(p-CF$_3$C$_6$H$_4$CH$_2$O) | 4-CH$_3$, 3-OCH$_2$C$_6$H$_5$ |
| 4-(m-CF$_3$OC$_6$H$_4$CH$_2$O) | 3-F, 4-OC$_6$H$_5$ |
| 4-(p-CF$_3$OC$_6$H$_4$CH$_2$O) | 3-F, 4-OCH$_2$C$_6$H$_5$ |
| 2-F, 5-(p-FC$_6$H$_4$O) | 3-Cl, 4-OC$_6$H$_5$ |
| 4-F, 3-OC$_6$H$_5$ | 3-Cl, 4-OCH$_2$C$_6$H$_5$ |
| 4-F, 3-OCH$_2$C$_6$H$_5$ | 3-Br, 4-OCH$_2$C$_6$H$_5$ |
| 4-Cl, 3-OC$_6$H$_5$ | 3-CH$_3$, 4-OC$_6$H$_5$ |
| 4-Cl, 3-OCH$_2$C$_6$H$_5$ | 3-CH$_3$, 4-OCH$_2$C$_6$H$_5$ |

TABLE 10

$$R^1 = (R^{16})_q \text{ on phenyl ring with } CH(CH_3) \text{ at position 1}$$

| $(R^{16})_q$ | $(R^{16})_q$ |
|---|---|
| H | 3-OCH$_2$C≡CBr |
| 2-F | 3-Cyclopentyl |
| 2-Cl | 3-Cyclohexyl |
| 3-F | 3(3-Cyclopentenyl) |
| 3-Cl | 3-(2-Cyclopentenyl) |
| 3-CH$_3$ | 3-(3-Cyclohexenyl) |
| 3-CF$_3$ | 3-(2-Cyclohexenyl) |
| 3-OCH$_3$ | 3-Cyclopropyloxy |
| 3-OCF$_3$ | 3-Cyclobutyloxy |
| 3-SCH$_3$ | 3-Cyclopentyloxy |
| 3-SC$_2$H$_5$ | 3-Cyclohexyloxy, |
| 3-SCF$_2$CHF$_2$ | 3-(3-Cyclopentenyl)oxy |
| 3-OCH$_2$CH=CH$_2$ | 3-(2-Cyclopentenyl)oxy |
| 3-OCH$_2$CH=CCl$_2$ | 3-(3-Cyclohexenyl)oxy |
| 3-OCH$_2$CH=CBr$_2$ | 3-(2-Cyclohexenyl)oxy |
| 3-OCH$_2$C≡CH | 3-OC$_6$H$_5$ |
| 3-OCH$_2$C≡CCl | 3-(o-CH$_3$C$_6$H$_4$O) |
| 3-(m-CH$_3$C$_6$H$_4$O) | 3-(p-FC$_6$H$_4$CH$_2$O) |

TABLE 10-continued $R^1 = (R^{16})_q$ on phenyl ring with CH(CH$_3$) substituent at position 1

| (R$^{16}$)$_q$ | (R$^{16}$)$_q$ |
|---|---|
| 3-(p-CH$_3$C$_6$H$_4$O) | 3-(o-BrC$_6$H$_4$CH$_2$O) |
| 3-(o-ClC$_6$H$_4$O) | 3-(m-BrC$_6$H$_4$CH$_2$O) |
| 3-(m-ClC$_6$H$_4$O) | 3-(p-BrC$_6$H$_4$CH$_2$O) |
| 3-(p-ClC$_6$H$_4$O) | 3-(o-CH$_3$C$_6$H$_4$CH$_2$O) |
| 3-(o-FC$_6$H$_4$O) | 3-(m-CH$_3$C$_6$H$_4$CH$_2$O) |
| 3-(m-FC$_6$H$_4$O) | 3-(p-CH$_3$C$_6$H$_4$CH$_2$O) |
| 3-(p-FC$_5$H$_4$O) | 3-(o-CF$_3$C$_6$H$_4$CH$_2$O) |
| 3-(o-6F$_3$C$_6$H$_4$O) | 3-(m-CF$_3$C$_6$H$_4$CH$_2$O) |
| 3-(m-CF$_3$C$_6$H$_4$O) | 3-(p-CF$_3$6H$_4$CH$_2$O) |
| 3-(p-CF$_3$C$_6$H$_4$O) | 3-CH$_2$C$_6$H$_5$ |
| 3-(m-(CH$_3$)$_3$CC$_6$H$_4$O) | 4-F |
| 3-(p-(CH$_3$)$_3$CC$_6$H$_4$O) | 4-Cl |
| 3-(m-CH$_3$OC$_6$H$_4$O) | 4-CH$_3$ |
| 3-(p-CH$_3$OC$_6$H$_4$O) | 4-OCH$_3$ |
| 3-(3,4-Cl$_2$C$_6$H$_3$O) | 4-CF$_3$ |
| 3-(3,5-Cl$_2$C$_6$H$_3$O) | 4-OCF$_3$ |
| 3-(m-CF$_3$OC$_6$H$_4$O) | 4-SCH$_3$ |
| 3-(p-CF$_3$OC$_6$H$_4$O) | 4-OCH$_2$CH=CH$_2$ |
| 3-C$_6$H$_5$ | 4-OCH$_2$CH=CCl$_2$ |
| 3-CH$_2$C$_6$H$_5$ | 4-OCH$_2$CH=CBr$_2$ |
| 3-(o-ClC$_6$H$_4$CH$_2$O) | 4-CH=CH$_2$ |
| 3-(m-ClC$_6$H$_4$CH$_2$O) | 4-OCH$_2$C≡CH |
| 3-(p-ClC$_6$H$_4$CH$_2$O) | 4-OCH$_2$C≡CCl |
| 3-(o-FC$_6$H$_4$CH$_2$O) | 4-OCH$_2$C≡Br |
| 3-(m-FC$_6$H$_4$CH$_2$O) | 4-Cyclopentyl |
| 4-Cyclohexyl | 4-(p-CH$_3$C$_6$H$_4$O) |
| 4-(3-Cyclopentenyl) | 4-(o-CF$_3$C$_6$H$_4$O) |
| 4-(2-Cyclopentenyl) | 4-(m-CF$_3$C$_6$H$_4$O) |
| 4-(3-Cyclohexenyl) | 4-(p-CF$_3$C$_6$H$_4$O) |
| 4-(2-Cyclohexenyl) | 4-(m-(CH$_3$)$_3$CC$_6$H$_4$O) |
| 4-Cyclopropyloxy | 4-(p-(CH$_3$)$_3$CC$_6$H$_4$O) |
| 4-Cyclobutyloxy | 4-(m-CH$_3$OC$_6$H$_4$O) |
| 4-Cyclopentyloxy | 4-(p-CH$_3$OC$_6$H$_4$O) |
| 4-Cyclohexyloxy | 4-(m-CF$_3$OC$_6$H$_4$O) |
| 4-(3-Cyclopentenyl)oxy | 4-(p-CF$_3$OC$_6$H$_4$O) |
| 4-(2-Cyclopentenyl)oxy | 4-CH$_2$C$_6$H$_5$, |
| 4-(3-Cyclohexenyl)oxy | 4-OCH$_2$C$_6$H$_5$ |
| 4-(1-Cyclohexenyl)oxy | 4-(o-ClC$_6$H$_4$CH$_2$O) |
| 4-(2-Cyclohexenyl) | 4-(m-ClC$_6$H$_4$CH$_2$O) |
| 4-C$_6$H$_5$ | 4-(p-ClC$_6$H$_4$CH$_2$O) |
| 4-OC$_6$H$_5$ | 4-(o-FC$_6$H$_4$CH$_2$O) |
| 4-(o-ClC$_6$H$_4$O) | 4-(m-FC$_6$H$_4$CH$_2$O) |
| 4-(m-ClC$_6$H$_4$O) | 4-(p-FC$_6$H$_5$CH$_2$O) |
| 4-(p-ClC$_6$H$_4$O) | 4-(o-BrC$_6$H$_4$CH$_2$O) |
| 4-(o-FC$_6$H$_4$O) | 4-(m-BrC$_6$H$_4$CH$_2$O) |
| 4-(m-FC$_6$H$_4$O) | 4-(p-BrC$_6$H$_4$CH$_2$O) |
| 4-(p-FC$_6$H$_4$O) | 4-(o-CH$_3$C$_6$H$_4$CH$_2$O) |
| 4-(o-CH$_3$C$_6$H$_4$O) | 4-(m-CH$_3$C$_6$H$_4$CH$_2$O) |
| 4-(m-CH$_3$C$_6$H$_4$O) | 4-(p-CH$_3$C$_6$H$_4$CH$_2$O) |
| 4-(o-CF$_3$C$_6$H$_4$CH$_2$O) | 4-CH$_3$, 3-OC$_6$H$_5$ |
| 4-(m-CF$_3$C$_6$H$_4$CH$_2$O) | 4-CH$_3$, 3-OCH$_2$C$_6$H$_5$ |
| 4-(p-CF$_3$C$_6$H$_4$CH$_2$O) | 3-F, 4-OC$_6$H$_5$ |
| 4-(m-CF$_3$OC$_6$H$_4$CH$_2$O) | 3-F,4-OCH$_2$C$_6$H$_5$ |
| 4-(p-CF$_3$OC$_5$H$_4$CH$_2$O) | 3-Cl, 4-OC$_6$H$_5$ |
| 2-F, 5-(p-FC$_6$H$_4$O) | 3-Cl, 4-OCH$_2$C$_6$H$_5$ |
| 4-F, 3-OC$_6$H$_5$ | 3-Br, 4-OCH$_2$C$_6$H$_5$ |
| 4-F, 3-OCH$_2$C$_6$H$_5$ | 3-CH$_3$, 4-OC$_6$H$_5$ |
| 4-Cl, 3-OC$_6$H$_5$ | 3-CH$_3$, 4-OCH$_2$C$_8$H$_5$ |
| 4-Cl, 3-OCH$_2$C$_6$H$_5$ | |
| 4-Br, 3-OCH$_2$C$_6$H$_5$ | |

TABLE 11

$R^1 = (R^{16})_q$ on phenyl ring with CH(CH$_2$CH$_3$) substituent at position 1

| (R$^{16}$)$_q$ | (R$^{16}$)$_q$ |
|---|---|
| H | 3H(p-CF$_3$C$_6$H$_4$O) |
| 3-F | 3-Cyclopentyl |
| 3-Cl | 3-Cyclohexyl |
| 3-Br | 3-Cyclopentyloxy |
| 3-CH$_3$ | 3-Cyclohexyloxy |
| 3-OCH$_3$ | 3-OCH$_2$CH=CCl$_2$ |
| 3-CF$_3$ | 3-OCH$_2$CH=CCl$_2$ |
| 3-CF$_3$ | 4-F |
| 3-CN | 4-Cl |
| 3-NO$_2$ | 4-Br |
| 3-OC$_6$H$_5$ | 4-CH$_3$ |
| 3-CH$_2$C$_6$H$_5$ | 4-OCH$_3$ |
| 3-OCH$_2$C$_6$H$_5$ | 4-CF$_3$ |
| 3-(p-FC$_6$H$_4$O) | 4-OCF$_3$ |
| 3-(p-ClC$_6$H$_4$O) | 4-CN |
| 3-(p-CH$_3$C$_6$H$_4$O) | 4-NO$_2$ |
| 3-(m-CF$_3$C$_6$H$_4$O) | 4-OC$_6$H$_5$ |
| 4-CH$_2$C$_6$H$_5$ | 4-Cl, 3-OC$_6$H$_5$ |
| 4-OCH$_2$C$_6$H$_5$ | 4-Cl, 3-OCH$_2$C$_6$H$_5$ |
| 4-(p-FC$_6$H$_4$O) | 4-OH$_3$, 3-OC$_6$H$_5$ |
| 4-(p-ClC$_6$H$_4$O) | 4-CH$_3$, 3-OC$_6$H$_4$CH$_2$ |
| 4-(m-CF$_3$C$_6$H$_4$O) | 4-Br, 3-OCH$_2$C$_6$H$_5$ |
| 4-(p-CF$_3$C$_6$H$_4$O) | 3-F, 4-OC$_6$H$_5$ |
| 4-Cyclopentyl | 3-F, 4-OCH$_2$C$_6$H$_5$ |
| 4-Cyclohexyl | 3-Cl, 4-OC$_6$H$_5$ |
| 4-Cyclopentyloxy | 3-Cl, 4-OCH$_2$C$_6$H$_5$ |
| 4-Cyclohexyloxy | 3-CH$_3$, 4-OC$_6$H$_5$ |
| 4-OCH$_2$CH=CCl$_2$ | 3-CH$_3$, 4-OCH$_2$C$_6$H$_5$ |
| 4-OCH$_2$CH=CBr$_2$ | 3-Br, 4-OCH$_2$C$_6$H$_5$ |
| 4-F, 3-OC$_6$H$_5$ | 3-Cl, 4-OCH$_2$CH=CCl$_2$ |
| 4-F, 3-OCH$_2$C$_6$H$_5$ | 3-Cl, 4-(OCH$_2$CH=CBr$_2$) |

TABLE 12

$R^1 = (R^{16})_q$ on phenyl ring with CH(CH(CH$_3$)$_2$) substituent at position 1

| (R$^{16}$)$_q$ | (R$^{16}$)$_q$ |
|---|---|
| H | 3-(p-CF$_3$C$_6$H$_4$O) |
| 3-F | 3-Cyclopentyl |
| 3-Cl | 3-Cyclohexyl |
| 3-Br | 3-Cyclopentyloxy |
| 3-CH$_3$ | 3-Cyclohexyloxy |
| 3-OCH$_3$ | 3-OCH$_2$CH=CCl$_2$ |
| 3-CF$_3$ | 3-OCH$_2$CH=CBr$_2$ |
| 3-OCF$_3$ | 4-F |
| 3-CN | 4-Cl |
| 3-NO$_2$ | 4-Br |
| 3-OC$_6$H$_5$ | 4-CH$_3$ |
| 3-CH$_2$C$_6$H$_5$ | 4-OCH$_3$ |
| 3-OCH$_2$C$_5$H$_5$ | 4-CF$_3$ |
| 3-(p-FC$_6$H$_4$O) | 4-OCF$_3$ |
| 3-(p-ClC$_6$H$_4$O) | 4-CN |
| 3-(p-CH$_3$C$_6$H$_4$O) | 4-NO$_2$ |
| 3-(m-CF$_3$C$_5$H$_4$O) | 4-OC$_6$H$_5$ |
| 4-CH$_2$C$_6$H$_5$ | 4-Cl, 3-OC$_6$H$_5$ |
| 4-OCH$_2$C$_6$H$_5$ | 4-Cl, 3-OCH$_2$C$_6$H$_5$ |
| 4-(p-FC$_6$H$_4$O) | 4-OH$_3$, 3-OC$_6$H$_5$ |
| 4-(p-ClC$_6$H$_4$O) | 4-CH$_3$, 3-OC$_6$H$_4$CH$_2$ |

TABLE 12-continued $R^1 = (R^{16})_q$ on phenyl ring (positions 2,3,4,5,6) with CH(CH$_2$(CH$_3$)$_2$) substituent at position 1

| $(R^{16})_q$ | $(R^{16})_q$ |
|---|---|
| 4-(p-CH$_3$C$_6$H$_4$O) | 4-Br, 3-OCH$_2$C$_6$H$_5$ |
| 4-(m-CF$_3$C$_6$H$_4$O) | 3-F, 4-OC$_6$H$_5$ |
| 4-(p-CF$_3$C$_6$H$_4$O) | 3-F, 4-OCH$_2$C$_6$H$_5$ |
| 4-Cyclopentyl | 3-Cl, 4-OC$_6$H$_5$ |
| 4-Cyclohexyl | 3-Cl, 4-OCH$_2$C$_6$H$_5$ |
| 4-Cyclopentyloxy | 3-CH$_3$, 4-OC$_6$H$_5$ |
| 4-Cyclohexyloxy | 3-CH$_3$, 4-OCH$_2$C$_6$H$_5$ |
| 4-OCH$_2$CH=CCl$_2$ | 3-Br, 4-OCH$_2$C$_6$H$_5$ |
| 4-OCH$_2$CH=CBr$_2$ | 3-Cl, 4-OCH$_2$CH=CCl$_2$ |
| 4-F, 3-OC$_6$H$_5$ | 3-Cl, 4-(OCH$_2$CH=CBr$_2$) |
| 4-F, 3-OCH$_2$C$_6$H$_5$ | |

TABLE 13

$R^1 = (R^{16})_q$ on phenyl ring with CR$^6$R$^5$CHR$^7$ substituent

| $(R^{16})_q$ | $R^5$ | $R^6$ | $R^7$ |
|---|---|---|---|
| H | H | H | H |
| 2-F | H | H | H |
| 2-Cl | H | H | H |
| 2-CH$_3$ | H | H | H |
| 2-CF$_3$ | H | H | H |
| 2-CH$_3$O | H | H | H |
| 3-F | H | H | H |
| 3-Cl | H | H | H |
| 3-Br | H | H | H |
| 3-CH$_3$ | H | H | H |
| 3-CF$_3$ | H | H | H |
| 3-OCH$_3$ | H | H | H |
| 3-OC$_2$H$_5$ | H | H | H |
| 3-O(CH$_2$)$_2$CH$_3$ | H | H | H |
| 3-OCH(CH$_3$)$_2$ | H | H | H |
| 3-OCF$_3$ | H | H | H |
| 3-OCHF$_2$ | H | H | H |
| 3-OCF$_2$Br | H | H | H |
| 3-OCH$_2$CF$_3$ | H | H | H |
| 3-CCF$_2$CHF$_2$ | H | H | H |
| 3-OCF$_2$CHFCF$_3$ | H | H | H |
| 4-F | H | H | H |
| 4-Cl | H | H | H |
| 4-Br | H | H | H |
| 4-CH$_3$ | H | H | H |
| 4-CF$_3$ | H | H | H |
| 4-OCH$_3$ | H | H | H |
| 4-OC$_2$H$_5$ | H | H | H |
| 4-O(CH$_2$)$_2$CH$_3$ | H | H | H |
| 4-OCH(CH$_3$)$_2$ | H | H | H |
| 4-OCF$_3$ | H | H | H |
| 4-OCHF$_2$ | H | H | H |
| 4-OCF$_2$Br | H | H | H |
| 4-OCH$_2$CF$_3$ | H | H | H |
| 4-OCF$_2$CHF$_2$ | H | H | H |
| 4-OCF$_2$CHFCF$_3$ | H | H | H |
| 2,4-F$_2$ | H | H | H |
| 2,5-F$_2$ | H | H | H |
| 2,6-F$_2$ | H | H | H |
| 3,4-F$_2$ | H | H | H |
| 3,5-F$_2$ | H | H | H |
| 3,5-(OCH$_3$)$_2$ | H | H | H |
| 3,4-OCH$_2$O | H | H | H |

TABLE 13-continued

| $(R^{16})_q$ | $R^5$ | $R^6$ | $R^7$ |
|---|---|---|---|
| 3-OCH$_3$, 4-OCH$_2$H$_5$ | H | H | H |
| 3-F, 4-OCH(CH$_3$)$_2$ | H | H | H |
| 3-Cl, 4-OCH(CH$_3$)$_2$ | H | H | H |
| 4-CN | H | H | H |
| 4-NO$_2$ | H | H | H |
| 2,3-F$_2$ | H | H | H |
| H | H | H | CH$_3$ |
| H | H | H | C$_2$H$_5$ |
| H | H | H | —CH$_2$CH$_2$CH$_3$ |
| H | H | H | —CH(CH$_3$)$_2$ |
| H | CH$_3$ | H | H |
| H | CH(CH$_3$)$_2$ | H | H |
| 4-F | CH(CH$_3$)$_2$ | H | H |
| 4-Cl | CH(CH$_3$)$_2$ | H | H |
| H | CF$_3$ | H | H |
| 4-F | CF$_3$ | H | H |
| 4-Cl | CF$_3$ | H | H |

TABLE 14

$R^1 = (R^{16})_q$ on phenyl ring with CR$^5$R$^6$CHR$^7$ substituent

| $(R^{16})_q$ | $R^5$ | $R^6$ | $R^7$ |
|---|---|---|---|
| H | H | H | H |
| 4-F | H | H | H |
| 4-Cl | H | H | H |
| 4-Br | H | H | H |
| 4-CH$_3$ | H | H | H |
| 4-CF$_3$ | H | H | H |
| 4-OCH$_3$ | H | H | H |
| 4-OCF$_3$ | H | H | H |
| 4-CN | H | H | H |
| 4-NO$_2$ | H | H | H |
| H | CH$_3$ | H | H |
| H | CH(CH$_3$)$_2$ | H | H |
| H | CF$_3$ | H | H |
| H | H | H | CH$_3$ |

TABLE 15

| $(R^{16})_q$ | $R^5$ | $R^6$ | $R^7$ |
|---|---|---|---|
| H | CH$_3$ | H | H |
| H | CH$_3$ | CH$_3$ | H |

TABLE 16

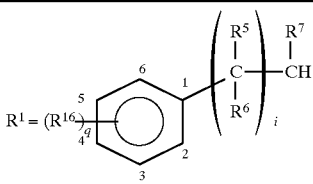

| R⁵ | R⁶ | R⁷ | i | (R¹⁶)q |
|---|---|---|---|---|
| H | H | H | 2 | H |
| H | H | H | 3 | H |
| H | H | H | 2 | 4-Cl |
| H | H | H | 3 | 4-Cl |
| H | H | H | 2 | 4-F |
| H | H | H | 3 | 4-F |
| H | H | H | 2 | 4-Br |
| H | H | H | 3 | 4-Br |
| H | H | H | 2 | 4-CH₃ |
| H | H | H | 3 | 4-CH₃ |
| H | H | H | 2 | 4-CF₃ |
| H | H | H | 3 | 4-CF₃ |
| H | H | H | 2 | 4-OCH₃ |
| H | H | H | 3 | 4-OCH₃ |
| H | H | H | 2 | 4-OCF₃ |
| H | H | H | 3 | 4-OCF₃ |
| H | H | H | 2 | 4-CO₂CH₃ |
| H | H | H | 3 | 4-CO₂CH₃ |
| H | H | H | 2 | 4-SCH₃ |
| H | H | H | 3 | 4-SCH₃ |
| H | H | H | 2 | 4-SCF₃ |
| H | H | H | 3 | 4-SCF₃ |
| H | H | H | 2 | 4-NHCOCH₃ |
| H | H | H | 3 | 4-NHCOCH₃ |
| H | H | H | 2 | 4-CONHCH₃ |
| H | H | H | 3 | 4-CONHCH₃ |
| H | H | H | 2 | 3-Cl |
| H | H | H | 3 | 3-Cl |
| H | H | H | 2 | 3-F |
| H | H | H | 3 | 3-F |
| H | H | H | 2 | 3-Br |
| H | H | H | 3 | 3-Br |
| H | H | H | 2 | 3-CH₃ |
| H | H | H | 3 | 3-CH₃ |
| H | H | H | 2 | 3-CF₃ |
| H | H | H | 3 | 3-CF₃ |
| H | H | H | 2 | 3-OCH₃ |
| H | H | H | 3 | 3-OCH₃ |
| H | H | H | 2 | 3-OCF₃ |
| H | H | H | 3 | 3-OCF₃ |
| H | H | H | 2 | 3-SCH₃ |
| H | H | H | 3 | 3-SCH₃ |
| H | H | H | 2 | 3-SCF₃ |
| H | H | H | 3 | 3-SCF₃ |
| H | H | H | 2 | 3-CONHCH₃ |
| H | H | H | 3 | 3-CONHCH₃ |
| H | H | H | 2 | 2-Cl |
| H | H | H | 3 | 2-Cl |

TABLE 17

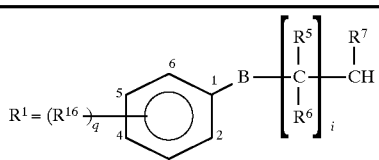

| B | R⁵ | R⁶ | R⁷ | i | (R¹⁶)q |
|---|---|---|---|---|---|
| O | H | H | H | 0 | H |
| O | H | H | H | 1 | H |
| O | H | H | H | 2 | H |
| O | H | H | H | 3 | H |
| O | H | H | H | 4 | H |
| O | H | H | H | 0 | 4-F |
| O | H | H | H | 1 | 4-F |
| O | H | H | H | 2 | 4-F |
| O | H | H | H | 3 | 4-F |
| O | H | H | H | 4 | 4-F |
| O | H | H | H | 0 | 4-Cl |
| O | H | H | H | 1 | 4-Cl |
| O | H | H | H | 2 | 4-Cl |
| O | H | H | H | 3 | 4-Cl |
| O | H | H | H | 4 | 4-Cl |
| O | H | H | H | 0 | 4-Br |
| O | H | H | H | 1 | 4-Br |
| O | H | H | H | 2 | 4-Br |
| O | H | H | H | 3 | 4-Br |
| O | H | H | H | 4 | 4-Br |
| O | H | H | H | 0 | 4-CN |
| O | H | H | H | 1 | 4-CN |
| O | H | H | H | 2 | 4-CN |
| O | H | H | H | 3 | 4-CN |
| O | H | H | H | 4 | 4-CN |
| O | H | H | H | 0 | 4-NO₂ |
| O | H | H | H | 1 | 4-NO₂ |
| O | H | H | H | 2 | 4-NO₂ |
| O | H | H | H | 3 | 4-NO₂ |
| O | H | H | H | 4 | 4-NO₂ |
| O | H | H | H | 0 | 4-CO₂CH₃ |
| O | H | H | H | 1 | 4-CO₂CH₃ |
| O | H | H | H | 2 | 4-CO₂CH₃ |
| O | H | H | H | 3 | 4-CO₂CH₃ |
| O | H | H | H | 4 | 4-CO₂CH₃ |
| O | H | H | H | 0 | 4-CH₃ |
| O | H | H | H | 1 | 4-CH₃ |
| O | H | H | H | 2 | 4-CH₃ |
| O | H | H | H | 3 | 4-CH₃ |
| O | H | H | H | 4 | 4-CH₃ |
| O | H | H | H | 0 | 4-CF₃ |
| O | H | H | H | 1 | 4-CF₃ |
| O | H | H | H | 2 | 4-CF₃ |
| O | H | H | H | 3 | 4-CF₃ |
| O | H | H | H | 4 | 4-CF₃ |
| O | H | H | H | 0 | 4-OCH₃ |
| O | H | H | H | 1 | 4-OCH₃ |
| O | H | H | H | 2 | 4-OCH₃ |
| O | H | H | H | 3 | 4-OCH₃ |
| O | H | H | H | 4 | 4-OCH₃ |
| O | H | H | H | 0 | 4-OC₂H₅ |
| O | H | H | H | 1 | 4-OC₂H₅ |
| O | H | H | H | 2 | 4-OC₂H₅ |
| O | H | H | H | 3 | 4-OC₂H₅ |
| O | H | H | H | 4 | 4-OC₂H₅ |
| O | H | H | H | 0 | 4-O(CH₂)₂CH₃ |
| O | H | H | H | 1 | 4-O(CH₂)₂CH₃ |
| O | H | H | H | 2 | 4-O(CH₂)₂CH₃ |
| O | H | H | H | 3 | 4-O(CH₂)₂CH₃ |
| O | H | H | H | 4 | 4-O(CH₂)₂CH₃ |
| O | H | H | H | 0 | 4-OCH(CH₃)₂ |
| O | H | H | H | 1 | 4-OCH(CH₃)₂ |
| O | H | H | H | 2 | 4-OCH(CH₃)₂ |
| O | H | H | H | 3 | 4-OCH(CH₃)₂ |
| O | H | H | H | 4 | 4-OCH(CH₃)₂ |
| O | H | H | H | 0 | 4-OCF₃ |
| O | H | H | H | 1 | 4-OCF₃ |
| O | H | H | H | 2 | 4-OCF₃ |
| O | H | H | H | 3 | 4-OCF₃ |
| O | H | H | H | 4 | 4-OCF₃ |
| O | H | H | H | 0 | 4-OCF₂CHF₂ |
| O | H | H | H | 1 | 4-OCF₂CHF₂ |

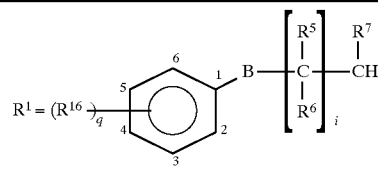

TABLE 17-continued

| B | R⁵ | R⁶ | R⁷ | i | (R¹⁶)$_q$ |
|---|---|---|---|---|---|
| O | H | H | H | 2 | 4-OCF$_2$CHF$_2$ |
| O | H | H | H | 3 | 4-OCF$_2$CHF$_2$ |
| O | H | H | H | 4 | 4-OCF$_2$CHF$_2$ |
| O | H | H | H | 0 | 4-SCH$_3$ |
| O | H | H | H | 1 | 4-SCH$_3$ |
| O | H | H | H | 2 | 4-SCH$_3$ |
| O | H | H | H | 3 | 4-SCH$_3$ |
| O | H | H | H | 4 | 4-SCH$_3$ |
| O | H | H | H | 0 | 4-SCF$_3$ |
| O | H | H | H | 1 | 4-SCF$_3$ |
| O | H | H | H | 2 | 4-SCF$_3$ |
| O | H | H | H | 3 | 4-SCF$_3$ |
| O | H | H | H | 4 | 4-SCF$_3$ |
| O | H | H | H | 0 | 4-CH$_3$S(O) |
| O | H | H | H | 1 | 4-CH$_3$S(O) |
| O | H | H | H | 2 | 4-CH$_3$S(O) |
| O | H | H | H | 3 | 4-CH$_3$S(O) |
| O | H | H | H | 4 | 4-CH$_3$S(O) |
| O | H | H | H | 0 | 4-CH$_3$S(O)$_2$ |
| O | H | H | H | 1 | 4-CH$_3$S(O)$_2$ |
| O | H | H | H | 2 | 4-CH$_3$S(O)$_2$ |
| O | H | H | H | 3 | 4-CH$_3$S(O)$_2$ |
| O | H | H | H | 4 | 4-CH$_3$S(O)$_2$ |
| O | H | H | H | 0 | 4-CF$_3$S(O) |
| O | H | H | H | 1 | 4-CF$_3$S(O) |
| O | H | H | H | 2 | 4-CF$_3$S(O) |
| O | H | H | H | 3 | 4-CF$_3$S(O) |
| O | H | H | H | 4 | 4-CF$_3$S(O) |
| O | H | H | H | 0 | 4-CF$_3$S(O)$_2$ |
| O | H | H | H | 1 | 4-CF$_3$S(O)$_2$ |
| O | H | H | H | 2 | 4-CF$_3$S(O)$_2$ |
| O | H | H | H | 3 | 4-CF$_3$S(O)$_2$ |
| O | H | H | H | 4 | 4-CF$_3$S(O)$_2$ |
| O | H | H | H | 0 | 4-OCH$_2$CH=CCl$_2$ |
| O | H | H | H | 1 | 4-OCH$_2$CH=CCl$_2$ |
| O | H | H | H | 2 | 4-OCH$_2$CH=CCl$_2$ |
| O | H | H | H | 3 | 4-OCH$_2$CH=CCl$_2$ |
| O | H | H | H | 4 | 4-OCH$_2$CH=CCl$_2$ |
| O | H | H | H | 0 | 4-OCH$_2$CH=CBr$_2$ |
| O | H | H | H | 1 | 4-OCH$_2$CH=CBr$_2$ |
| O | H | H | H | 2 | 4-OCH$_2$CH=CBr$_2$ |
| O | H | H | H | 3 | 4-OCH$_2$CH=CBr$_2$ |
| O | H | H | H | 4 | 4-OCH$_2$CH=CBr$_2$ |
| O | H | H | H | 0 | 4-CH$_2$OCH$_3$ |
| O | H | H | H | 1 | 4-CH$_2$OCH$_3$ |
| O | H | H | H | 2 | 4-CH$_2$OCH$_3$ |
| O | H | H | H | 3 | 4-CH$_2$OCH$_3$ |
| O | H | H | H | 4 | 4-CH$_2$OCH$_3$ |
| O | H | H | H | 0 | 4-CH$_2$SCH$_3$ |
| O | H | H | H | 1 | 4-CH$_2$SCH$_3$ |
| O | H | H | H | 2 | 4-CH$_2$SCH$_3$ |
| O | H | H | H | 3 | 4-CH$_2$SCH$_3$ |
| O | H | H | H | 4 | 4-CH$_2$SCH$_3$ |
| O | H | H | H | 0 | 4-N(CH$_3$)$_2$ |
| O | H | H | H | 1 | 4-N(CH$_3$)$_2$ |
| O | H | H | H | 2 | 4-N(CH$_3$)$_2$ |
| O | H | H | H | 3 | 4-N(CH$_3$)$_2$ |
| O | H | H | H | 4 | 4-N(CH$_3$)$_2$ |
| O | H | H | H | 0 | 4-NHCOCH$_3$ |
| O | H | H | H | 1 | 4-NHCOCH$_3$ |
| O | H | H | H | 2 | 4-NHCOCH$_3$ |
| O | H | H | H | 3 | 4-NHCOCH$_3$ |
| O | H | H | H | 4 | 4-NHCOCH$_3$ |
| O | H | H | H | 0 | 4-CHO |
| O | H | H | H | 1 | 4-CHO |
| O | H | H | H | 2 | 4-CHO |
| O | H | H | H | 3 | 4-CHO |
| O | H | H | H | 4 | 4-CHO |
| O | H | H | H | 0 | 4-CONHCH$_3$ |
| O | H | H | H | 1 | 4-CONHCH$_3$ |
| O | H | H | H | 2 | 4-CONHCH$_3$ |
| O | H | H | H | 3 | 4-CONHCH$_3$ |
| O | H | H | H | 4 | 4-CONHCH$_3$ |
| O | H | H | H | 0 | 4-CON(CH$_3$)$_2$ |
| O | H | H | H | 1 | 4-CON(CH$_3$)$_2$ |
| O | H | H | H | 2 | 4-CON(CH$_3$)$_2$ |
| O | H | H | H | 3 | 4-CON(CH$_3$)$_2$ |
| O | H | H | H | 4 | 4-CON(CH$_3$)$_2$ |
| O | H | H | H | 0 | 4-Cyclopentyloxy |
| O | H | H | H | 1 | 4-Cyclopentyloxy |
| O | H | H | H | 2 | 4-Cyclopentyloxy |
| O | H | H | H | 3 | 4-Cyclopentyloxy |
| O | H | H | H | 4 | 4-Cyclopentyloxy |
| O | H | H | H | 0 | 4-Cyclohexyloxy |
| O | H | H | H | 1 | 4-Cyclohexyloxy |
| O | H | H | H | 2 | 4-Cyclohexyloxy |
| O | H | H | H | 3 | 4-Cyclohexyloxy |
| O | H | H | H | 4 | 4-Cyclohexyloxy |
| O | H | H | H | 0 | 4-C$_6$H$_5$ |
| O | H | H | H | 1 | 4-C$_6$H$_5$ |
| O | H | H | H | 2 | 4-C$_6$H$_5$ |
| O | H | H | H | 3 | 4-C$_6$H$_5$ |
| O | H | H | H | 4 | 4-C$_6$H$_5$ |
| O | H | H | H | 0 | 4-C$_6$H$_5$O |
| O | H | H | H | 1 | 4-C$_6$H$_5$O |
| O | H | H | H | 2 | 4-C$_6$H$_5$O |
| O | H | H | H | 3 | 4-C$_6$H$_5$O |
| O | H | H | H | 4 | 4-C$_6$H$_5$O |
| O | H | H | H | 0 | 4-C$_6$H$_5$CH$_2$ |
| O | H | H | H | 1 | 4-C$_6$H$_5$CH$_2$ |
| O | H | H | H | 2 | 4-C$_6$H$_5$CH$_2$ |
| O | H | H | H | 3 | 4-C$_6$H$_5$CH$_2$ |
| O | H | H | H | 4 | 4-C$_6$H$_5$CH$_2$ |
| O | H | H | H | 0 | 4-C$_6$H$_5$CH$_2$O |
| O | H | H | H | 1 | 4-C$_6$H$_5$CH$_2$O |
| O | H | H | H | 2 | 4-C$_6$H$_5$CH$_2$O |
| O | H | H | H | 3 | 4-C$_6$H$_5$CH$_2$O |
| O | H | H | H | 4 | 4-C$_6$H$_5$CH$_2$O |
| O | H | H | H | 0 | 4-(4-FC$_6$H$_4$O) |
| O | H | H | H | 1 | 4-(4-FC$_6$H$_4$O) |
| O | H | H | H | 2 | 4-(4-FC$_6$H$_4$O) |
| O | H | H | H | 3 | 4-(4-FC$_6$H$_4$O) |
| O | H | H | H | 4 | 4-(4-FC$_6$H$_4$O) |
| O | H | H | H | 0 | 4-(4-ClC$_6$H$_4$O) |
| O | H | H | H | 1 | 4-(4-ClC$_6$H$_4$O) |
| O | H | H | H | 2 | 4-(4-ClC$_6$H$_4$O) |
| O | H | H | H | 3 | 4-(4-ClC$_6$H$_4$O) |
| O | H | H | H | 4 | 4-(4-ClC$_6$H$_4$O) |
| O | H | H | H | 0 | 4-(4-CH$_3$C$_6$H$_4$O) |
| O | H | H | H | 1 | 4-(4-CH$_3$C$_6$H$_4$O) |
| O | H | H | H | 2 | 4-(4-CH$_3$C$_6$H$_4$O) |
| O | H | H | H | 3 | 4-(4-CH$_3$C$_6$H$_4$O) |
| O | H | H | H | 4 | 4-(4-CH$_3$C$_6$H$_4$O) |
| O | H | H | H | 0 | 4-(3-CF$_3$C$_6$H$_4$O) |
| O | H | H | H | 1 | 4-(3-CF$_3$C$_6$H$_4$O) |
| O | H | H | H | 2 | 4-(3-CF$_3$C$_6$H$_4$O) |
| O | H | H | H | 3 | 4-(3-CF$_3$C$_6$H$_4$O) |
| O | H | H | H | 4 | 4-(3-CF$_3$C$_6$H$_4$O) |
| O | H | H | H | 0 | 4-(4-CF$_3$C$_6$H$_4$O) |
| O | H | H | H | 1 | 4-(4-CF$_3$C$_6$H$_4$O) |
| O | H | H | H | 2 | 4-(4-CF$_3$C$_6$H$_4$O) |
| O | H | H | H | 3 | 4-(4-CF$_3$C$_6$H$_4$O) |
| O | H | H | H | 4 | 4-(4-CF$_3$C$_6$H$_4$O) |
| O | H | H | H | 0 | 3-F |
| O | H | H | H | 1 | 3-F |
| O | H | H | H | 2 | 3-F |

TABLE 17-continued

R¹ = (R¹⁶)q— [phenyl ring positions 1-6] —B—[C(R⁵)(R⁶)]ᵢ—CH(R⁷)

| B | R⁵ | R⁶ | R⁷ | i | (R¹⁶)q |
|---|----|----|----|---|--------|
| O | H | H | H | 3 | 3-F |
| O | H | H | H | 4 | 3-F |
| O | H | H | H | 0 | 3-Cl |
| O | H | H | H | 1 | 3-Cl |
| O | H | H | H | 2 | 3-Cl |
| O | H | H | H | 3 | 3-Cl |
| O | H | H | H | 4 | 3-Cl |
| O | H | H | H | 0 | 3-Br |
| O | H | H | H | 1 | 3-Br |
| O | H | H | H | 2 | 3-Br |
| O | H | H | H | 3 | 3-Br |
| O | H | H | H | 4 | 3-Br |
| O | H | H | H | 0 | 3-CN |
| O | H | H | H | 1 | 3-CN |
| O | H | H | H | 2 | 3-CN |
| O | H | H | H | 3 | 3-CN |
| O | H | H | H | 4 | 3-CN |
| O | H | H | H | 0 | 3-NO₂ |
| O | H | H | H | 1 | 3-NO₂ |
| O | H | H | H | 2 | 3-NO₂ |
| O | H | H | H | 3 | 3-NO₂ |
| O | H | H | H | 4 | 3-NO₂ |
| O | H | H | H | 0 | 3-CH₃ |
| O | H | H | H | 1 | 3-CH₃ |
| O | H | H | H | 2 | 3-CH₃ |
| O | H | H | H | 3 | 3-CH₃ |
| O | H | H | H | 4 | 3-CH₃ |
| O | H | H | H | 0 | 3-CF₃ |
| O | H | H | H | 1 | 3-CF₃ |
| O | H | H | H | 2 | 3-CF₃ |
| O | H | H | H | 3 | 3-CF₃ |
| O | H | H | H | 4 | 3-CF₃ |
| O | H | H | H | 0 | 3-OCH₃ |
| O | H | H | H | 1 | 3-OCH₃ |
| O | H | H | H | 2 | 3-OCH₃ |
| O | H | H | H | 3 | 3-OCH₃ |
| O | H | H | H | 4 | 3-OCH₃ |
| O | H | H | H | 0 | 3-OC₂H₅ |
| O | H | H | H | 1 | 3-OC₂H₅ |
| O | H | H | H | 2 | 3-OC₂H₅ |
| O | H | H | H | 3 | 3-OC₂H₅ |
| O | H | H | H | 4 | 3-OC₂H₅ |
| O | H | H | H | 0 | 3-O(CH₂)₂CH₃ |
| O | H | H | H | 1 | 3-O(CH₂)₂CH₃ |
| O | H | H | H | 2 | 3-O(CH₂)₂CH₃ |
| O | H | H | H | 3 | 3-O(CH₂)₂CH₃ |
| O | H | H | H | 4 | 3-O(CH₂)₂CH₃ |
| O | H | H | H | 0 | 3-OCH(CH₃)₂ |
| O | H | H | H | 1 | 3-OCH(CH₃)₂ |
| O | H | H | H | 2 | 3-OCH(CH₃)₂ |
| O | H | H | H | 3 | 3-OCH(CH₃)₂ |
| O | H | H | H | 4 | 3-OCH(CH₃)₂ |
| O | H | H | H | 0 | 3-OCF₃ |
| O | H | H | H | 1 | 3-OCF₃ |
| O | H | H | H | 2 | 3-OCF₃ |
| O | H | H | H | 3 | 3-OCF₃ |
| O | H | H | H | 4 | 3-OCF₃ |
| O | H | H | H | 0 | 3-SCH₃ |
| O | H | H | H | 1 | 3-SCH₃ |
| O | H | H | H | 2 | 3-SCH₃ |
| O | H | H | H | 3 | 3-SCH₃ |
| O | H | H | H | 4 | 3-SCH₃ |
| O | H | H | H | 0 | 3-SCF₃ |
| O | H | H | H | 1 | 3-SCF₃ |
| O | H | H | H | 2 | 3-SCF₃ |
| O | H | H | H | 3 | 3-SCF₃ |
| O | H | H | H | 4 | 3-SCF₃ |
| O | H | H | H | 0 | 3-CONHCH₃ |
| O | H | H | H | 1 | 3-CONHCH₃ |
| O | H | H | H | 2 | 3-CONHCH₃ |
| O | H | H | H | 3 | 3-CONHCH₃ |
| O | H | H | H | 4 | 3-CONHCH₃ |
| O | H | H | H | 0 | 3-CON(CH₃)₂ |
| O | H | H | H | 1 | 3-CON(CH₃)₂ |
| O | H | H | H | 2 | 3-CON(CH₃)₂ |
| O | H | H | H | 3 | 3-CON(CH₃)₂ |
| O | H | H | H | 4 | 3-CON(CH₃)₂ |
| O | H | H | H | 0 | 3-Cyclopentyloxy |
| O | H | H | H | 1 | 3-Cyclopentyloxy |
| O | H | H | H | 2 | 3-Cyclopentyloxy |
| O | H | H | H | 3 | 3-Cyclopentyloxy |
| O | H | H | H | 4 | 3-Cyclopentyloxy |
| O | H | H | H | 0 | 3-Cyclohexyloxy |
| O | H | H | H | 1 | 3-Cyclohexyloxy |
| O | H | H | H | 2 | 3-Cyclohexyloxy |
| O | H | H | H | 3 | 3-Cyclohexyloxy |
| O | H | H | H | 4 | 3-Cyclohexyloxy |
| O | H | H | H | 0 | 3-C₆H₅ |
| O | H | H | H | 1 | 3-C₆H₅ |
| O | H | H | H | 2 | 3-C₆H₅ |
| O | H | H | H | 3 | 3-C₆H₅ |
| O | H | H | H | 4 | 3-C₆H₅ |
| O | H | H | H | 0 | 3-C₆H₅O |
| O | H | H | H | 1 | 3-C₆H₅O |
| O | H | H | H | 2 | 3-C₆H₅O |
| O | H | H | H | 3 | 3-C₆H₅O |
| O | H | H | H | 4 | 3-C₆H₅O |
| O | H | H | H | 0 | 3-C₆H₅CH₂ |
| O | H | H | H | 1 | 3-C₆H₅CH₂ |
| O | H | H | H | 2 | 3-C₆H₅CH₂ |
| O | H | H | H | 3 | 3-C₆H₅CH₂ |
| O | H | H | H | 4 | 3-C₆H₅CH₂ |
| O | H | H | H | 0 | 3-C₆H₅CH₂O |
| O | H | H | H | 1 | 3-C₆H₅CH₂O |
| O | H | H | H | 2 | 3-C₆H₅CH₂O |
| O | H | H | H | 3 | 3-C₆H₅CH₂O |
| O | H | H | H | 4 | 3-C₆H₅CH₂O |
| O | H | H | H | 0 | 3-(4-FC₆H₄O) |
| O | H | H | H | 1 | 3-(4-FC₆H₄O) |
| O | H | H | H | 2 | 3-(4-FC₆H₄O) |
| O | H | H | H | 3 | 3-(4-FC₆H₄O) |
| O | H | H | H | 4 | 3-(4-FC₆H₄O) |
| O | H | H | H | 0 | 3-(4-ClC₆H₄O) |
| O | H | H | H | 1 | 3-(4-ClC₆H₄O) |
| O | H | H | H | 2 | 3-(4-ClC₆H₄O) |
| O | H | H | H | 3 | 3-(4-ClC₆H₄O) |
| O | H | H | H | 4 | 3-(4-ClC₆H₄O) |
| O | H | H | H | 0 | 3-(4-CH₃C₆H₄O) |
| O | H | H | H | 1 | 3-(4-CH₃C₆H₄O) |
| O | H | H | H | 2 | 3-(4-CH₃C₆H₄O) |
| O | H | H | H | 3 | 3-(4-CH₃C₆H₄O) |
| O | H | H | H | 4 | 3-(4-CH₃C₆H₄O) |
| O | H | H | H | 0 | 3-(3-CF₃C₆H₄O) |
| O | H | H | H | 1 | 3-(3-CF₃C₆H₄O) |
| O | H | H | H | 2 | 3-(3-CF₃C₆H₄O) |
| O | H | H | H | 3 | 3-(3-CF₃C₆H₄O) |
| O | H | H | H | 4 | 3-(3-CF₃C₆H₄O) |
| O | H | H | H | 0 | 3-(4-CF₃C₆H₄O) |
| O | H | H | H | 1 | 3-(4-CF₃C₆H₄O) |
| O | H | H | H | 2 | 3-(4-CF₃C₆H₄O) |
| O | H | H | H | 3 | 3-(4-CF₃C₆H₄O) |
| O | H | H | H | 4 | 3-(4-CF₃C₆H₄O) |
| O | H | H | H | 0 | 2-F |
| O | H | H | H | 1 | 2-F |
| O | H | H | H | 2 | 2-F |
| O | H | H | H | 3 | 2-F |

TABLE 17-continued $R^1 = (R^{16})_q$ — phenyl(positions 1-6) — B — [C(R^5)(R^6)]_i — CH(R^7)

| B | R^5 | R^6 | R^7 | i | (R^16)_q |
|---|---|---|---|---|---|
| O | H | H | H | 4 | 2-F |
| O | H | H | H | 0 | 2-Cl |
| O | H | H | H | 1 | 2-Cl |
| O | H | H | H | 2 | 2-Cl |
| O | H | H | H | 3 | 2-Cl |
| O | H | H | H | 4 | 2-Cl |
| O | H | H | H | 0 | 2-Br |
| O | H | H | H | 1 | 2-Br |
| O | H | H | H | 2 | 2-Br |
| O | H | H | H | 3 | 2-Br |
| O | H | H | H | 4 | 2-Br |
| O | H | H | H | 0 | 2-CH_3 |
| O | H | H | H | 1 | 2-CH_3 |
| O | H | H | H | 2 | 2-CH_3 |
| O | H | H | H | 3 | 2-CH_3 |
| O | H | H | H | 4 | 2-CH_3 |
| O | H | H | H | 0 | 2-CF_3 |
| O | H | H | H | 1 | 2-CF_3 |
| O | H | H | H | 2 | 2-CF_3 |
| O | H | H | H | 3 | 2-CF_3 |
| O | H | H | H | 4 | 2-CF_3 |
| O | H | H | H | 0 | 2-OCH_3 |
| O | H | H | H | 1 | 2-OCH_3 |
| O | H | H | H | 2 | 2-OCH_3 |
| O | H | H | H | 3 | 2-OCH_3 |
| O | H | H | H | 4 | 2-OCH_3 |
| O | H | H | H | 0 | 2-OCF_3 |
| O | H | H | H | 1 | 2-OCF_3 |
| O | H | H | H | 2 | 2-OCF_3 |
| O | H | H | H | 3 | 2-OCF_3 |
| O | H | H | H | 4 | 2-OCF_3 |
| O | H | H | H | 0 | 2-CONHCH_3 |
| O | H | H | H | 1 | 2-CONHCH_3 |
| O | H | H | H | 2 | 2-CONHCH_3 |
| O | H | H | H | 3 | 2-CONHCH_3 |
| O | H | H | H | 4 | 2-CONHCH_3 |
| O | H | H | H | 0 | 2-CON(CH_3)_2 |
| O | H | H | H | 1 | 2-CON(CH_3)_2 |
| O | H | H | H | 2 | 2-CON(CH_3)_2 |
| O | H | H | H | 3 | 2-CON(CH_3)_2 |
| O | H | H | H | 4 | 2-CON(CH_3)_2 |
| O | H | H | H | 0 | 2-C_6H_5 |
| O | H | H | H | 1 | 2-C_6H_5 |
| O | H | H | H | 2 | 2-C_6H_5 |
| O | H | H | H | 3 | 2-C_6H_5 |
| O | H | H | H | 4 | 2-C_6H_5 |
| O | H | H | H | 0 | 2-SCH_3 |
| O | H | H | H | 1 | 2-SCH_3 |
| O | H | H | H | 2 | 2-SCH_3 |
| O | H | H | H | 3 | 2-SCH_3 |
| O | H | H | H | 4 | 2-SCH_3 |
| O | H | H | H | 0 | 2-SCF_3 |
| O | H | H | H | 1 | 2-SCF_3 |
| O | H | H | H | 2 | 2-SCF_3 |
| O | H | H | H | 3 | 2-SCF_3 |
| O | H | H | H | 4 | 2-SCF_3 |
| S | H | H | H | 0 | 4-F |
| S | H | H | H | 1 | 4-F |
| S | H | H | H | 2 | 4-F |
| S | H | H | H | 3 | 4-F |
| S | H | H | H | 4 | 4-F |
| S | H | H | H | 0 | 4-Cl |
| S | H | H | H | 1 | 4-Cl |
| S | H | H | H | 2 | 4-Cl |
| S | H | H | H | 3 | 4-Cl |
| S | H | H | H | 4 | 4-Cl |
| S | H | H | H | 0 | 4-Br |
| S | H | H | H | 1 | 4-Br |
| S | H | H | H | 2 | 4-Br |
| S | H | H | H | 3 | 4-Br |
| S | H | H | H | 4 | 4-Br |
| S | H | H | H | 0 | 4-CH_3 |
| S | H | H | H | 1 | 4-CH_3 |
| S | H | H | H | 2 | 4-CH_3 |
| S | H | H | H | 3 | 4-CH_3 |
| S | H | H | H | 4 | 4-CH_3 |
| S | H | H | H | 0 | 4-CF_3 |
| S | H | H | H | 1 | 4-CF_3 |
| S | H | H | H | 2 | 4-CF_3 |
| S | H | H | H | 3 | 4-CF_3 |
| S | H | H | H | 4 | 4-CF_3 |
| S | H | H | H | 0 | 4-OCH_3 |
| S | H | H | H | 1 | 4-OCH_3 |
| S | H | H | H | 2 | 4-OCH_3 |
| S | H | H | H | 3 | 4-OCH_3 |
| S | H | H | H | 4 | 4-OCH_3 |
| S | H | H | H | 0 | 4-OCF_3 |
| S | H | H | H | 1 | 4-OCF_3 |
| S | H | H | H | 2 | 4-OCF_3 |
| S | H | H | H | 3 | 4-OCF_3 |
| S | H | H | H | 4 | 4-OCF_3 |
| S | H | H | H | 0 | 4-SCH_3 |
| S | H | H | H | 1 | 4-SCH_3 |
| S | H | H | H | 2 | 4-SCH_3 |
| S | H | H | H | 3 | 4-SCH_3 |
| S | H | H | H | 4 | 4-SCH_3 |
| S | H | H | H | 0 | 4-SCF_3 |
| S | H | H | H | 1 | 4-SCF_3 |
| S | H | H | H | 2 | 4-SCF_3 |
| S | H | H | H | 3 | 4-SCF_3 |
| S | H | H | H | 4 | 4-SCF_3 |
| S | H | H | H | 0 | 4-Cyclopentyloxy |
| S | H | H | H | 1 | 4-Cyclopentyloxy |
| S | H | H | H | 2 | 4-Cyclopentyloxy |
| S | H | H | H | 3 | 4-Cyclopentyloxy |
| S | H | H | H | 4 | 4-Cyclopentyloxy |
| S | H | H | H | 0 | 4-Cyclohexyloxy |
| S | H | H | H | 1 | 4-Cyclohexyloxy |
| S | H | H | H | 2 | 4-Cyclohexyloxy |
| S | H | H | H | 3 | 4-Cyclohexyloxy |
| S | H | H | H | 4 | 4-Cyclohexyloxy |
| S | H | H | H | 0 | 4-C_6H_5 |
| S | H | H | H | 1 | 4-C_6H_5 |
| S | H | H | H | 2 | 4-C_6H_5 |
| S | H | H | H | 3 | 4-C_6H_5 |
| S | H | H | H | 4 | 4-C_6H_5 |
| S | H | H | H | 0 | 4-C_6H_5O |
| S | H | H | H | 1 | 4-C_6H_5O |
| S | H | H | H | 2 | 4-C_6H_5O |
| S | H | H | H | 3 | 4-C_6H_5O |
| S | H | H | H | 4 | 4-C_6H_5O |
| S | H | H | H | 0 | 4-C_6H_5CH_2 |
| S | H | H | H | 1 | 4-C_6H_5CH_2 |
| S | H | H | H | 2 | 4-C_6H_5CH_2 |
| S | H | H | H | 3 | 4-C_6H_5CH_2 |
| S | H | H | H | 4 | 4-C_6H_5CH_2 |
| S | H | H | H | 0 | 4-C_6H_5CH_2O |
| S | H | H | H | 1 | 4-C_6H_5CH_2O |
| S | H | H | H | 2 | 4-C_6H_5CH_2O |
| S | H | H | H | 3 | 4-C_6H_5CH_2O |
| S | H | H | H | 4 | 4-C_6H_5CH_2O |
| S | H | H | H | 0 | 3-F |
| S | H | H | H | 1 | 3-F |
| S | H | H | H | 2 | 3-F |
| S | H | H | H | 3 | 3-F |
| S | H | H | H | 4 | 3-F |

TABLE 17-continued

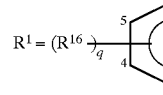

| B | R⁵ | R⁶ | R⁷ | i | (R¹⁶)_q |
|---|----|----|----|---|---------|
| S | H | H | H | 0 | 3-Cl |
| S | H | H | H | 1 | 3-Cl |
| S | H | H | H | 2 | 3-Cl |
| S | H | H | H | 3 | 3-Cl |
| S | H | H | H | 4 | 3-Cl |
| S | H | H | H | 0 | 3-Br |
| S | H | H | H | 1 | 3-Br |
| S | H | H | H | 2 | 3-Br |
| S | H | H | H | 3 | 3-Br |
| S | H | H | H | 4 | 3-Br |
| S | H | H | H | 0 | 3-CH₃ |
| S | H | H | H | 1 | 3-CH₃ |
| S | H | H | H | 2 | 3-CH₃ |
| S | H | H | H | 3 | 3-CH₃ |
| S | H | H | H | 4 | 3-CH₃ |
| S | H | H | H | 0 | 3-CF₃ |
| S | H | H | H | 1 | 3-CF₃ |
| S | H | H | H | 2 | 3-CF₃ |
| S | H | H | H | 3 | 3-CF₃ |
| S | H | H | H | 4 | 3-CF₃ |
| S | H | H | H | 0 | 3-OCH₃ |
| S | H | H | H | 1 | 3-OCH₃ |
| S | H | H | H | 2 | 3-OCH₃ |
| S | H | H | H | 3 | 3-OCH₃ |
| S | H | H | H | 4 | 3-OCH₃ |
| S | H | H | H | 0 | 3-OCF₃ |
| S | H | H | H | 1 | 3-OCF₃ |
| S | H | H | H | 2 | 3-OCF₃ |
| S | H | H | H | 3 | 3-OCF₃ |
| S | H | H | H | 4 | 3-OCF₃ |
| S | H | H | H | 0 | 3-SCH₃ |
| S | H | H | H | 1 | 3-SCH₃ |
| S | H | H | H | 2 | 3-SCH₃ |
| S | H | H | H | 3 | 3-SCH₃ |
| S | H | H | H | 4 | 3-SCH₃ |
| S | H | H | H | 0 | 3-SCF₃ |
| S | H | H | H | 1 | 3-SCF₃ |
| S | H | H | H | 2 | 3-SCF₃ |
| S | H | H | H | 3 | 3-SCF₃ |
| S | H | H | H | 4 | 3-SCF₃ |
| S | H | H | H | 0 | 3-Cyclopentyloxy |
| S | H | H | H | 1 | 3-Cyclopentyloxy |
| S | H | H | H | 2 | 3-Cyclopentyloxy |
| S | H | H | H | 3 | 3-Cyclopentyloxy |
| S | H | H | H | 4 | 3-Cyclopentyloxy |
| S | H | H | H | 0 | 3-Cyclohexyloxy |
| S | H | H | H | 1 | 3-Cyclohexyloxy |
| S | H | H | H | 2 | 3-Cyclohexyloxy |
| S | H | H | H | 3 | 3-Cyclohexyloxy |
| S | H | H | H | 4 | 3-Cyclohexyloxy |
| S | H | H | H | 0 | 3-C₆H₅ |
| S | H | H | H | 1 | 3-C₆H₅ |
| S | H | H | H | 2 | 3-C₆H₅ |
| S | H | H | H | 3 | 3-C₆H₅ |
| S | H | H | H | 4 | 3-C₆H₅ |
| S | H | H | H | 0 | 3-C₆H₅O |
| S | H | H | H | 1 | 3-C₆H₅O |
| S | H | H | H | 2 | 3-C₆H₅O |
| S | H | H | H | 3 | 3-C₆H₅O |
| S | H | H | H | 4 | 3-C₆H₅O |
| S | H | H | H | 0 | 3-C₆H₅CH₂ |
| S | H | H | H | 1 | 3-C₆H₅CH₂ |
| S | H | H | H | 2 | 3-C₆H₅CH₂ |
| S | H | H | H | 3 | 3-C₆H₅CH₂ |
| S | H | H | H | 4 | 3-C₆H₅CH₂ |
| S | H | H | H | 0 | 3-C₆H₅CH₂O |
| S | H | H | H | 1 | 3-C₆H₅CH₂O |
| S | H | H | H | 2 | 3-C₆H₅CH₂O |

TABLE 17-continued

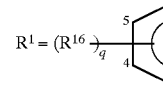

| B | R⁵ | R⁶ | R⁷ | i | (R¹⁶)_q |
|---|----|----|----|---|---------|
| S | H | H | H | 3 | 3-C₆H₅CH₂O |
| S | H | H | H | 4 | 3-C₆H₅CH₂O |
| NH | H | H | H | 0 | H |
| NH | H | H | H | 1 | H |
| NH | H | H | H | 2 | H |
| NH | H | H | H | 3 | H |
| NH | H | H | H | 4 | H |
| NH | H | H | H | 0 | 4-F |
| NH | H | H | H | 1 | 4-F |
| NH | H | H | H | 2 | 4-F |
| NH | H | H | H | 3 | 4-F |
| NH | H | H | H | 4 | 4-F |
| NH | H | H | H | 0 | 4-Br |
| NH | H | H | H | 1 | 4-Br |
| NH | H | H | H | 2 | 4-Br |
| NH | H | H | H | 3 | 4-Br |
| NH | H | H | H | 4 | 4-Br |
| NH | H | H | H | 0 | 4-CH₃ |
| NH | H | H | H | 1 | 4-CH₃ |
| NH | H | H | H | 2 | 4-CH₃ |
| NH | H | H | H | 3 | 4-CH₃ |
| NH | H | H | H | 4 | 4-CH₃ |
| NH | H | H | H | 0 | 4-CF₃ |
| NH | H | H | H | 1 | 4-CF₃ |
| NH | H | H | H | 2 | 4-CF₃ |
| NH | H | H | H | 3 | 4-CF₃ |
| NH | H | H | H | 4 | 4-CF₃ |
| NH | H | H | H | 0 | 4-OCH₃ |
| NH | H | H | H | 1 | 4-OCH₃ |
| NH | H | H | H | 2 | 4-OCH₃ |
| NH | H | H | H | 3 | 4-OCH₃ |
| NH | H | H | H | 4 | 4-OCH₃ |
| NH | H | H | H | 0 | 4-OCF₃ |
| NH | H | H | H | 1 | 4-OCF₃ |
| NH | H | H | H | 2 | 4-OCF₃ |
| NH | H | H | H | 3 | 4-OCF₃ |
| NH | H | H | H | 4 | 4-OCF₃ |
| NH | H | H | H | 0 | 4-SCH₃ |
| NH | H | H | H | 1 | 4-SCH₃ |
| NH | H | H | H | 2 | 4-SCH₃ |
| NH | H | H | H | 3 | 4-SCH₃ |
| NH | H | H | H | 4 | 4-SCH₃ |
| NH | H | H | H | 0 | 4-SCF₃ |
| NH | H | H | H | 1 | 4-SCF₃ |
| NH | H | H | H | 2 | 4-SCF₃ |
| NH | H | H | H | 3 | 4-SCF₃ |
| NH | H | H | H | 4 | 4-SCF₃ |
| NH | H | H | H | 0 | 4-CONHCH₃ |
| NH | H | H | H | 1 | 4-CONHCH₃ |
| NH | H | H | H | 2 | 4-CONHCH₃ |
| NH | H | H | H | 3 | 4-CONHCH₃ |
| NH | H | H | H | 4 | 4-CONHCH₃ |
| NH | H | H | H | 0 | 4-CON(CH₃)₂ |
| NH | H | H | H | 1 | 4-CON(CH₃)₂ |
| NH | H | H | H | 2 | 4-CON(CH₃)₂ |
| NH | H | H | H | 3 | 4-CON(CH₃)₂ |
| NH | H | H | H | 4 | 4-CON(CH₃)₂ |
| NH | H | H | H | 0 | 3-F |
| NH | H | H | H | 1 | 3-F |
| NH | H | H | H | 2 | 3-F |
| NH | H | H | H | 3 | 3-F |
| NH | H | H | H | 4 | 3-F |
| NH | H | H | H | 0 | 3-Cl |
| NH | H | H | H | 1 | 3-Cl |
| NH | H | H | H | 2 | 3-Cl |
| NH | H | H | H | 3 | 3-Cl |
| NH | H | H | H | 4 | 3-Cl |
| NH | H | H | H | 0 | 3-Br |

TABLE 17-continued $R^1 = (R^{16})_q$ — phenyl — B — [C(R^5)(R^6)]_i — CH(R^7)

| B | R⁵ | R⁶ | R⁷ | i | (R¹⁶)_q |
|---|----|----|----|---|---------|
| NH | H | H | H | 1 | 3-Br |
| NH | H | H | H | 2 | 3-Br |
| NH | H | H | H | 3 | 3-Br |
| NH | H | H | H | 4 | 3-Br |
| NH | H | H | H | 0 | 3-CH₃ |
| NH | H | H | H | 1 | 3-CH₃ |
| NH | H | H | H | 2 | 3-CH₃ |
| NH | H | H | H | 3 | 3-CH₃ |
| NH | H | H | H | 4 | 3-CH₃ |
| NH | H | H | H | 0 | 3-CF₃ |
| NH | H | H | H | 1 | 3-CF₃ |
| NH | H | H | H | 2 | 3-CF₃ |
| NH | H | H | H | 3 | 3-CF₃ |
| NH | H | H | H | 4 | 3-CF₃ |
| NH | H | H | H | 0 | 3-CH₃O |
| NH | H | H | H | 1 | 3-CH₃O |
| NH | H | H | H | 2 | 3-CH₃O |
| NH | H | H | H | 3 | 3-CH₃O |
| NH | H | H | H | 4 | 3-CH₃O |
| NH | H | H | H | 0 | 3-CF₃O |
| NH | H | H | H | 1 | 3-CF₃O |
| NH | H | H | H | 2 | 3-CF₃O |
| NH | H | H | H | 3 | 3-CF₃O |
| NH | H | H | H | 4 | 3-CF₃O |
| NH | H | H | H | 0 | 3-CH₃S |
| NH | H | H | H | 1 | 3-CH₃S |
| NH | H | H | H | 2 | 3-CH₃S |
| NH | H | H | H | 3 | 3-CH₃S |
| NH | H | H | H | 4 | 3-CH₃S |
| NH | H | H | H | 0 | 3-CF₃S |
| NH | H | H | H | 1 | 3-CF₃S |
| NH | H | H | H | 2 | 3-CF₃S |
| NH | H | H | H | 3 | 3-CF₃S |
| NH | H | H | H | 4 | 3-CF₃S |
| NH | H | H | H | 0 | 3-CONHCH₃ |
| NH | H | H | H | 1 | 3-CONHCH₃ |
| NH | H | H | H | 2 | 3-CONHCH₃ |
| NH | H | H | H | 3 | 3-CONHCH₃ |
| NH | H | H | H | 4 | 3-CONHCH₃ |
| NH | H | H | H | 0 | 3-CON(CH₃)₂ |
| NH | H | H | H | 1 | 3-CON(CH₃)₂ |
| NH | H | H | H | 2 | 3-CON(CH₃)₂ |
| NH | H | H | H | 3 | 3-CON(CH₃)₂ |
| NH | H | H | H | 4 | 3-CON(CH₃)₂ |
| NCH₃ | H | H | H | 0 | 3-CF₃ |
| NCH₃ | H | H | H | 1 | 3-CF₃ |
| NCH₃ | H | H | H | 2 | 3-CF₃ |
| NCH₃ | H | H | H | 3 | 3-CF₃ |
| NCH₃ | H | H | H | 4 | 3-CF₃ |
| NCH₃ | H | H | H | 0 | H |
| NCH₃ | H | H | H | 1 | H |
| NCH₃ | H | H | H | 2 | H |
| NCH₃ | H | H | H | 3 | H |
| NCH₃ | H | H | H | 4 | H |
| NCH₃ | H | H | H | 0 | 4-F |
| NCH₃ | H | H | H | 1 | 4-F |
| NCH₃ | H | H | H | 2 | 4-F |
| NCH₃ | H | H | H | 3 | 4-F |
| NCH₃ | H | H | H | 4 | 4-F |
| NCH₃ | H | H | H | 0 | 4-Cl |
| NCH₃ | H | H | H | 1 | 4-Cl |
| NCH₃ | H | H | H | 2 | 4-Cl |
| NCH₃ | H | H | H | 3 | 4-Cl |
| NCH₃ | H | H | H | 4 | 4-Cl |
| NCH₃ | H | H | H | 0 | 4-Br |
| NCH₃ | H | H | H | 1 | 4-Br |
| NCH₃ | H | H | H | 2 | 4-Br |
| NCH₃ | H | H | H | 3 | 4-Br |
| NCH₃ | H | H | H | 4 | 4-Br |
| NCH₃ | H | H | H | 0 | 4-CH₃ |
| NCH₃ | H | H | H | 1 | 4-CH₃ |
| NCH₃ | H | H | H | 2 | 4-CH₃ |
| NCH₃ | H | H | H | 3 | 4-CH₃ |
| NCH₃ | H | H | H | 4 | 4-CH₃ |
| NCH₃ | H | H | H | 0 | 4-CF₃ |
| NCH₃ | H | H | H | 1 | 4-CF₃ |
| NCH₃ | H | H | H | 2 | 4-CF₃ |
| NCH₃ | H | H | H | 3 | 4-CF₃ |
| NCH₃ | H | H | H | 4 | 4-CF₃ |
| NCH₃ | H | H | H | 0 | 3-F |
| NCH₃ | H | H | H | 1 | 3-F |
| NCH₃ | H | H | H | 2 | 3-F |
| NCH₃ | H | H | H | 3 | 3-F |
| NCH₃ | H | H | H | 4 | 3-F |
| NCH₃ | H | H | H | 0 | 3-Cl |
| NCH₃ | H | H | H | 1 | 3-Cl |
| NCH₃ | H | H | H | 2 | 3-Cl |
| NCH₃ | H | H | H | 3 | 3-Cl |
| NCH₃ | H | H | H | 4 | 3-Cl |
| NCH₃ | H | H | H | 0 | 3-Br |
| NCH₃ | H | H | H | 1 | 3-Br |
| NCH₃ | H | H | H | 2 | 3-Br |
| NCH₃ | H | H | H | 3 | 3-Br |
| NCH₃ | H | H | H | 4 | 3-Br |
| NCH₃ | H | H | H | 0 | 3-CH₃ |
| NCH₃ | H | H | H | 1 | 3-CH₃ |
| NCH₃ | H | H | H | 2 | 3-CH₃ |
| NCH₃ | H | H | H | 3 | 3-CH₃ |
| NCH₃ | H | H | H | 4 | 3-CH₃ |
| C(=O)O | H | H | H | 0 | H |
| C(=O)O | H | H | H | 1 | H |
| C(=O)O | H | H | H | 2 | H |
| C(=O)O | H | H | H | 3 | H |
| C(=O)O | H | H | H | 4 | H |
| C(=O)O | H | H | H | 0 | 4-F |
| C(=O)O | H | H | H | 1 | 4-F |
| C(=O)O | H | H | H | 2 | 4-F |
| C(=O)O | H | H | H | 3 | 4-F |
| C(=O)O | H | H | H | 4 | 4-F |
| C(=O)O | H | H | H | 0 | 4-Cl |
| C(=O)O | H | H | H | 1 | 4-Cl |
| C(=O)O | H | H | H | 2 | 4-Cl |
| C(=O)O | H | H | H | 3 | 4-Cl |
| C(=O)O | H | H | H | 4 | 4-Cl |
| C(=O)O | H | H | H | 0 | 4-Br |
| C(=O)O | H | H | H | 1 | 4-Br |
| C(=O)O | H | H | H | 2 | 4-Br |
| C(=O)O | H | H | H | 3 | 4-Br |
| C(=O)O | H | H | H | 4 | 4-Br |
| C(=O)O | H | H | H | 0 | 4-CH₃ |
| C(=O)O | H | H | H | 1 | 4-CH₃ |
| C(=O)O | H | H | H | 2 | 4-CH₃ |
| C(=O)O | H | H | H | 3 | 4-CH₃ |
| C(=O)O | H | H | H | 4 | 4-CH₃ |
| C(=O)O | H | H | H | 0 | 4-CF₃ |
| C(=O)O | H | H | H | 1 | 4-CF₃ |
| C(=O)O | H | H | H | 2 | 4-CF₃ |
| C(=O)O | H | H | H | 3 | 4-CF₃ |
| C(=O)O | H | H | H | 4 | 4-CF₃ |
| C(=O)O | H | H | H | 0 | 4-OCH₃ |
| C(=O)O | H | H | H | 1 | 4-OCH₃ |
| C(=O)O | H | H | H | 2 | 4-OCH₃ |
| C(=O)O | H | H | H | 3 | 4-OCH₃ |
| C(=O)O | H | H | H | 4 | 4-OCH₃ |
| C(=O)O | H | H | H | 0 | 4-OCF₃ |
| C(=O)O | H | H | H | 1 | 4-OCF₃ |

TABLE 17-continued

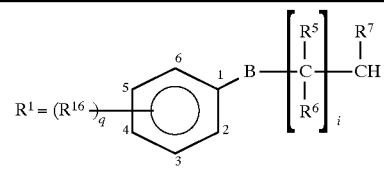

| B | R⁵ | R⁶ | R⁷ | i | (R¹⁶)q |
|---|---|---|---|---|---|
| C(=O)O | H | H | H | 2 | 4-OCF₃ |
| C(=O)O | H | H | H | 3 | 4-OCF₃ |
| C(=O)O | H | H | H | 4 | 4-OCF₃ |
| C(=O)O | H | H | H | 0 | 4-CONHCH₃ |
| C(=O)O | H | H | H | 1 | 4-CONHCH₃ |
| C(=O)O | H | H | H | 2 | 4-CONHCH₃ |
| C(=O)O | H | H | H | 3 | 4-CONHCH₃ |
| C(=O)O | H | H | H | 4 | 4-CONHCH₃ |
| C(=O)O | H | H | H | 0 | 4-CON(CH₃)₂ |
| C(=O)O | H | H | H | 1 | 4-CON(CH₃)₂ |
| C(=O)O | H | H | H | 2 | 4-CON(CH₃)₂ |
| C(=O)O | H | H | H | 3 | 4-CON(CH₃)₂ |
| C(=O)O | H | H | H | 4 | 4-CON(CH₃)₂ |
| C(=O)O | H | H | H | 0 | 3-F |
| C(=O)O | H | H | H | 1 | 3-F |
| C(=O)O | H | H | H | 2 | 3-F |
| C(=O)O | H | H | H | 3 | 3-F |
| C(=O)O | H | H | H | 4 | 3-F |
| C(=O)O | H | H | H | 0 | 3-Cl |
| C(=O)O | H | H | H | 1 | 3-Cl |
| C(=O)O | H | H | H | 2 | 3-Cl |
| C(=O)O | H | H | H | 3 | 3-Cl |
| C(=O)O | H | H | H | 4 | 3-Cl |
| C(=O)O | H | H | H | 0 | 3-Br |
| C(=O)O | H | H | H | 1 | 3-Br |
| C(=O)O | H | H | H | 2 | 3-Br |
| C(=O)O | H | H | H | 3 | 3-Br |
| C(=O)O | H | H | H | 4 | 3-Br |
| C(=O)O | H | H | H | 0 | 3-CH₃ |
| C(=O)O | H | H | H | 1 | 3-CH₃ |
| C(=O)O | H | H | H | 2 | 3-CH₃ |
| C(=O)O | H | H | H | 3 | 3-CH₃ |
| C(=O)O | H | H | H | 4 | 3-CH₃ |
| C(=O)O | H | H | H | 0 | 3-CF₃ |
| C(=O)O | H | H | H | 1 | 3-CF₃ |
| C(=O)O | H | H | H | 2 | 3-CF₃ |
| C(=O)O | H | H | H | 3 | 3-CF₃ |
| C(=O)O | H | H | H | 4 | 3-CF₃ |
| C(=O)O | H | H | H | 0 | 3-OCH₃ |
| C(=O)O | H | H | H | 1 | 3-OCH₃ |
| C(=O)O | H | H | H | 2 | 3-OCH₃ |
| C(=O)O | H | H | H | 3 | 3-OCH₃ |
| C(=O)O | H | H | H | 4 | 3-OCH₃ |
| C(=O)O | H | H | H | 0 | 3-OCF₃ |
| C(=O)O | H | H | H | 1 | 3-OCF₃ |
| C(=O)O | H | H | H | 2 | 3-OCF₃ |
| C(=O)O | H | H | H | 3 | 3-OCF₃ |
| C(=O)O | H | H | H | 4 | 3-OCF₃ |
| C(=O)O | H | H | H | 0 | 3-CONHCH₃ |
| C(=O)O | H | H | H | 1 | 3-CONHCH₃ |
| C(=O)O | H | H | H | 2 | 3-CONHCH₃ |
| C(=O)O | H | H | H | 3 | 3-CONHCH₃ |
| C(=O)O | H | H | H | 4 | 3-CONHCH₃ |
| C(=O)O | H | H | H | 0 | 3-CON(CH₃)₂ |
| C(=O)O | H | H | H | 1 | 3-CON(CH₃)₂ |
| C(=O)O | H | H | H | 2 | 3-CON(CH₃)₂ |
| C(=O)O | H | H | H | 3 | 3-CON(CH₃)₂ |
| C(=O)O | H | H | H | 4 | 3-CON(CH₃)₂ |
| C(=O)NH | H | H | H | 0 | H |
| C(=O)NH | H | H | H | 1 | H |
| C(=O)NH | H | H | H | 2 | H |
| C(=O)NH | H | H | H | 3 | H |
| C(=O)NH | H | H | H | 4 | H |
| C(=O)NH | H | H | H | 0 | 4-F |
| C(=O)NH | H | H | H | 1 | 4-F |
| C(=O)NH | H | H | H | 2 | 4-F |
| C(=O)NH | H | H | H | 3 | 4-F |
| C(=O)NH | H | H | H | 4 | 4-F |

TABLE 17-continued

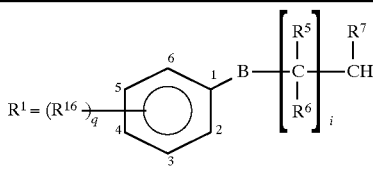

| B | R⁵ | R⁶ | R⁷ | i | (R¹⁶)q |
|---|---|---|---|---|---|
| C(=O)NH | H | H | H | 0 | 4-Cl |
| C(=O)NH | H | H | H | 1 | 4-Cl |
| C(=O)NH | H | H | H | 2 | 4-Cl |
| C(=O)NH | H | H | H | 3 | 4-Cl |
| C(=O)NH | H | H | H | 4 | 4-Cl |
| C(=O)NH | H | H | H | 0 | 4-Br |
| C(=O)NH | H | H | H | 1 | 4-Br |
| C(=O)NH | H | H | H | 2 | 4-Br |
| C(=O)NH | H | H | H | 3 | 4-Br |
| C(=O)NH | H | H | H | 4 | 4-Br |
| C(=O)NH | H | H | H | 0 | 4-CH₃ |
| C(=O)NH | H | H | H | 1 | 4-CH₃ |
| C(=O)NH | H | H | H | 2 | 4-CH₃ |
| C(=O)NH | H | H | H | 3 | 4-CH₃ |
| C(=O)NH | H | H | H | 4 | 4-CH₃ |
| C(=O)NH | H | H | H | 0 | 4-CF₃ |
| C(=O)NH | H | H | H | 1 | 4-CF₃ |
| C(=O)NH | H | H | H | 2 | 4-CF₃ |
| C(=O)NH | H | H | H | 3 | 4-CF₃ |
| C(=O)NH | H | H | H | 4 | 4-CF₃ |
| C(=O)NH | H | H | H | 0 | 4-OCH₃ |
| C(=O)NH | H | H | H | 1 | 4-OCH₃ |
| C(=O)NH | H | H | H | 2 | 4-OCH₃ |
| C(=O)NH | H | H | H | 3 | 4-OCH₃ |
| C(=O)NH | H | H | H | 4 | 4-OCH₃ |
| C(=O)NH | H | H | H | 0 | 4-OCF₃ |
| C(=O)NH | H | H | H | 1 | 4-OCF₃ |
| C(=O)NH | H | H | H | 2 | 4-OCF₃ |
| C(=O)NH | H | H | H | 3 | 4-OCF₃ |
| C(=O)NH | H | H | H | 4 | 4-OCF₃ |
| C(=O)NH | H | H | H | 0 | 4-CONHCH₃ |
| C(=O)NH | H | H | H | 1 | 4-CONHCH₃ |
| C(=O)NH | H | H | H | 2 | 4-CONHCH₃ |
| C(=O)NH | H | H | H | 3 | 4-CONHCH₃ |
| C(=O)NH | H | H | H | 4 | 4-CONHCH₃ |
| C(=O)NH | H | H | H | 0 | 4-CON(CH₃)₂ |
| C(=O)NH | H | H | H | 1 | 4-CON(CH₃)₂ |
| C(=O)NH | H | H | H | 2 | 4-CON(CH₃)₂ |
| C(=O)NH | H | H | H | 3 | 4-CON(CH₃)₂ |
| C(=O)NH | H | H | H | 4 | 4-CON(CH₃)₂ |
| C(=O)NH | H | H | H | 0 | 3-F |
| C(=O)NH | H | H | H | 1 | 3-F |
| C(=O)NH | H | H | H | 2 | 3-F |
| C(=O)NH | H | H | H | 3 | 3-F |
| C(=O)NH | H | H | H | 4 | 3-F |
| C(=O)NH | H | H | H | 0 | 3-Cl |
| C(=O)NH | H | H | H | 1 | 3-Cl |
| C(=O)NH | H | H | H | 2 | 3-Cl |
| C(=O)NH | H | H | H | 3 | 3-Cl |
| C(=O)NH | H | H | H | 4 | 3-Cl |
| C(=O)NH | H | H | H | 0 | 3-Br |
| C(=O)NH | H | H | H | 1 | 3-Br |
| C(=O)NH | H | H | H | 2 | 3-Br |
| C(=O)NH | H | H | H | 3 | 3-Br |
| C(=O)NH | H | H | H | 4 | 3-Br |
| C(=O)NH | H | H | H | 0 | 3-CH₃ |
| C(=O)NH | H | H | H | 1 | 3-CH₃ |
| C(=O)NH | H | H | H | 2 | 3-CH₃ |
| C(=O)NH | H | H | H | 3 | 3-CH₃ |
| C(=O)NH | H | H | H | 4 | 3-CH₃ |
| C(=O)NH | H | H | H | 0 | 3-CF₃ |
| C(=O)NH | H | H | H | 1 | 3-CF₃ |
| C(=O)NH | H | H | H | 2 | 3-CF₃ |
| C(=O)NH | H | H | H | 3 | 3-CF₃ |
| C(=O)NH | H | H | H | 4 | 3-CF₃ |
| C(=O)NH | H | H | H | 0 | 3-OCH₃ |
| C(=O)NH | H | H | H | 1 | 3-OCH₃ |
| C(=O)NH | H | H | H | 2 | 3-OCH₃ |

TABLE 17-continued

| B | R⁵ | R⁶ | R⁷ | i | (R¹⁶)q |
|---|---|---|---|---|---|
| C(=O)NH | H | H | H | 3 | 3-OCH₃ |
| C(=O)NH | H | H | H | 4 | 3-OCH₃ |
| C(=O)NH | H | H | H | 0 | 3-OCF₃ |
| C(=O)NH | H | H | H | 1 | 3-OCF₃ |
| C(=O)NH | H | H | H | 2 | 3-OCF₃ |
| C(=O)NH | H | H | H | 3 | 3-OCF₃ |
| C(=O)NH | H | H | H | 4 | 3-OCF₃ |
| C(=O)NH | H | H | H | 0 | 3-CONHCH₃ |
| C(=O)NH | H | H | H | 1 | 3-CONHCH₃ |
| C(=O)NH | H | H | H | 2 | 3-CONHCH₃ |
| C(=O)NH | H | H | H | 3 | 3-CONHCH₃ |
| C(=O)NH | H | H | H | 4 | 3-CONHCH₃ |
| C(=O)NH | H | H | H | 0 | 3-CON(CH₃)₂ |
| C(=O)NH | H | H | H | 1 | 3-CON(CH₃)₂ |
| C(=O)NH | H | H | H | 2 | 3-CON(CH₃)₂ |
| C(=O)NH | H | H | H | 3 | 3-CON(CH₃)₂ |
| C(=O)NH | H | H | H | 4 | 3-CON(CH₃)₂ |
| OC(=O) | H | H | H | 0 | H |
| OC(=O) | H | H | H | 1 | H |
| OC(=O) | H | H | H | 2 | H |
| OC(=O) | H | H | H | 3 | H |
| OC(=O) | H | H | H | 4 | H |
| OC(=O) | H | H | H | 0 | 4-F |
| OC(=O) | H | H | H | 1 | 4-F |
| OC(=O) | H | H | H | 2 | 4-F |
| OC(=O) | H | H | H | 3 | 4-F |
| OC(=O) | H | H | H | 4 | 4-F |
| OC(=O) | H | H | H | 0 | 4-Cl |
| OC(=O) | H | H | H | 1 | 4-Cl |
| OC(=O) | H | H | H | 2 | 4-Cl |
| OC(=O) | H | H | H | 3 | 4-Cl |
| OC(=O) | H | H | H | 4 | 4-Cl |
| OC(=O) | H | H | H | 0 | 4-Br |
| OC(=O) | H | H | H | 1 | 4-Br |
| OC(=O) | H | H | H | 2 | 4-Br |
| OC(=O) | H | H | H | 3 | 4-Br |
| OC(=O) | H | H | H | 4 | 4-Br |
| OC(=O) | H | H | H | 0 | 4-CH₃ |
| OC(=O) | H | H | H | 1 | 4-CH₃ |
| OC(=O) | H | H | H | 2 | 4-CH₃ |
| OC(=O) | H | H | H | 3 | 4-CH₃ |
| OC(=O) | H | H | H | 4 | 4-CH₃ |
| OC(=O) | H | H | H | 0 | 4-CF₃ |
| OC(=O) | H | H | H | 1 | 4-CF₃ |
| OC(=O) | H | H | H | 2 | 4-CF₃ |
| OC(=O) | H | H | H | 3 | 4-CF₃ |
| OC(=O) | H | H | H | 4 | 4-CF₃ |
| OC(=O) | H | H | H | 0 | 3-F |
| OC(=O) | H | H | H | 1 | 3-F |
| OC(=O) | H | H | H | 2 | 3-F |
| OC(=O) | H | H | H | 3 | 3-F |
| OC(=O) | H | H | H | 4 | 3-F |
| OC(=O) | H | H | H | 0 | 3-Cl |
| OC(=O) | H | H | H | 1 | 3-Cl |
| OC(=O) | H | H | H | 2 | 3-Cl |
| OC(=O) | H | H | H | 3 | 3-Cl |
| OC(=O) | H | H | H | 4 | 3-Cl |
| OC(=O) | H | H | H | 0 | 3-Br |
| OC(=O) | H | H | H | 1 | 3-Br |
| OC(=O) | H | H | H | 2 | 3-Br |
| OC(=O) | H | H | H | 3 | 3-Br |
| OC(=O) | H | H | H | 4 | 3-Br |
| OC(=O) | H | H | H | 0 | 3-CH₃ |
| OC(=O) | H | H | H | 1 | 3-CH₃ |
| OC(=O) | H | H | H | 2 | 3-CH₃ |
| OC(=O) | H | H | H | 3 | 3-CH₃ |
| OC(=O) | H | H | H | 4 | 3-CH₃ |
| OC(=O) | H | H | H | 0 | 3-CF₃ |
| OC(=O) | H | H | H | 1 | 3-CF₃ |
| OC(=O) | H | H | H | 2 | 3-CF₃ |
| OC(=O) | H | H | H | 3 | 3-CF₃ |
| OC(=O) | H | H | H | 4 | 3-CF₃ |
| OC(=O) | H | H | H | 0 | 2-Cl |
| OC(=O) | H | H | H | 1 | 2-Cl |
| OC(=O) | H | H | H | 2 | 2-Cl |
| OC(=O) | H | H | H | 3 | 2-Cl |
| OC(=O) | H | H | H | 4 | 2-Cl |
| NHC(=O) | H | H | H | 0 | H |
| NHC(=O) | H | H | H | 1 | H |
| NHC(=O) | H | H | H | 2 | H |
| NHC(=O) | H | H | H | 3 | H |
| NHC(=O) | H | H | H | 4 | H |
| NHC(=O) | H | H | H | 0 | 4-F |
| NHC(=O) | H | H | H | 1 | 4-F |
| NHC(=O) | H | H | H | 2 | 4-F |
| NHC(=O) | H | H | H | 3 | 4-F |
| NHC(=O) | H | H | H | 4 | 4-F |
| NHC(=O) | H | H | H | 0 | 4-Cl |
| NHC(=O) | H | H | H | 1 | 4-Cl |
| NHC(=O) | H | H | H | 2 | 4-Cl |
| NHC(=O) | H | H | H | 3 | 4-Cl |
| NHC(=O) | H | H | H | 4 | 4-Cl |
| NHC(=O) | H | H | H | 0 | 4-Br |
| NHC(=O) | H | H | H | 1 | 4-Br |
| NHC(=O) | H | H | H | 2 | 4-Br |
| NHC(=O) | H | H | H | 3 | 4-Br |
| NHC(=O) | H | H | H | 4 | 4-Br |
| NHC(=O) | H | H | H | 0 | 4-CH₃ |
| NHC(=O) | H | H | H | 1 | 4-CH₃ |
| NHC(=O) | H | H | H | 2 | 4-CH₃ |
| NHC(=O) | H | H | H | 3 | 4-CH₃ |
| NHC(=O) | H | H | H | 4 | 4-CH₃ |
| NHC(=O) | H | H | H | 0 | 4-OCH₃ |
| NHC(=O) | H | H | H | 1 | 4-OCH₃ |
| NHC(=O) | H | H | H | 2 | 4-OCH₃ |
| NHC(=O) | H | H | H | 3 | 4-OCH₃ |
| NHC(=O) | H | H | H | 4 | 4-OCH₃ |
| NHC(=O) | H | H | H | 0 | 4-CF₃ |
| NHC(=O) | H | H | H | 1 | 4-CF₃ |
| NHC(=O) | H | H | H | 2 | 4-CF₃ |
| NHC(=O) | H | H | H | 3 | 4-CF₃ |
| NHC(=O) | H | H | H | 4 | 4-CF₃ |
| NHC(=O) | H | H | H | 0 | 4-OCF₃ |
| NHC(=O) | H | H | H | 1 | 4-OCF₃ |
| NHC(=O) | H | H | H | 2 | 4-OCF₃ |
| NHC(=O) | H | H | H | 3 | 4-OCF₃ |
| NHC(=O) | H | H | H | 4 | 4-OCF₃ |
| NHC(=O) | H | H | H | 0 | 3-F |
| NHC(=O) | H | H | H | 1 | 3-F |
| NHC(=O) | H | H | H | 2 | 3-F |
| NHC(=O) | H | H | H | 3 | 3-F |
| NHC(=O) | H | H | H | 4 | 3-F |
| NHC(=O) | H | H | H | 0 | 3-Cl |
| NHC(=O) | H | H | H | 1 | 3-Cl |
| NHC(=O) | H | H | H | 2 | 3-Cl |
| NHC(=O) | H | H | H | 3 | 3-Cl |
| NHC(=O) | H | H | H | 4 | 3-Cl |
| NHC(=O) | H | H | H | 0 | 3-Br |
| NHC(=O) | H | H | H | 1 | 3-Br |
| NHC(=O) | H | H | H | 2 | 3-Br |
| NHC(=O) | H | H | H | 3 | 3-Br |
| NHC(=O) | H | H | H | 4 | 3-Br |
| NHC(=O) | H | H | H | 0 | 3-CH₃ |
| NHC(=O) | H | H | H | 1 | 3-CH₃ |
| NHC(=O) | H | H | H | 2 | 3-CH₃ |
| NHC(=O) | H | H | H | 3 | 3-CH₃ |

TABLE 17-continued

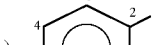

| B | R⁵ | R⁶ | R⁷ | i | (R¹⁶)q |
|---|---|---|---|---|---|
| NHC(=O) | H | H | H | 4 | 3-CH₃ |
| NHC(=O) | H | H | H | 0 | 3-OCH₃ |
| NHC(=O) | H | H | H | 1 | 3-OCH₃ |
| NHC(=O) | H | H | H | 2 | 3-OCH₃ |
| NHC(=O) | H | H | H | 3 | 3-OCH₃ |
| NHC(=O) | H | H | H | 4 | 3-OCH₃ |
| NHC(=O) | H | H | H | 0 | 3-CF₃ |
| NHC(=O) | H | H | H | 1 | 3-CF₃ |
| NHC(=O) | H | H | H | 2 | 3-CF₃ |
| NHC(=O) | H | H | H | 3 | 3-CF₃ |
| NHC(=O) | H | H | H | 4 | 3-CF₃ |
| NHC(=O) | H | H | H | 0 | 3-OCF₃ |
| NHC(=O) | H | H | H | 1 | 3-OCF₃ |
| NHC(=O) | H | H | H | 2 | 3-OCF₃ |
| NHC(=O) | H | H | H | 3 | 3-OCF₃ |
| NHC(=O) | H | H | H | 4 | 3-OCF₃ |
| C(=O)N(CH₃) | H | H | H | 0 | H |
| C(=O)N(CH₃) | H | H | H | 1 | H |
| C(=O)N(CH₃) | H | H | H | 2 | H |
| C(=O)N(CH₃) | H | H | H | 3 | H |
| C(=O)N(CH₃) | H | H | H | 4 | H |
| C(=O)N(CH₃) | H | H | H | 0 | 4-Cl |
| C(=O)N(CH₃) | H | H | H | 1 | 4-Cl |
| C(=O)N(CH₃) | H | H | H | 2 | 4-Cl |
| C(=O)N(CH₃) | H | H | H | 3 | 4-Cl |
| C(=O)N(CH₃) | H | H | H | 4 | 4-Cl |
| C(=O)N(CH₃) | H | H | H | 0 | 4-CF₃ |
| C(=O)N(CH₃) | H | H | H | 1 | 4-CF₃ |
| C(=O)N(CH₃) | H | H | H | 2 | 4-CF₃ |
| C(=O)N(CH₃) | H | H | H | 3 | 4-CF₃ |
| C(=O)N(CH₃) | H | H | H | 4 | 4-CF₃ |

TABLE 18

| (R¹⁶)q | (R¹⁶)q |
|---|---|
| 6-CH₃ | 3,6-(CH₃)₂ |
| 6-CH₂CH₃ | 3,5-(CH₃)₂ |
| 6-CH₂CH₂CH₃ | 4,5-(CH₃)₂ |
| 6-Phenyl | 4,6-(CH₃)₂ |
| 5-CH₃ | 5,6-(CH₃)₂ |
| 5-CH₂CH₃ | 6-Cl |
| 5-CH(CH₃)₂ | 5-Cl |
| 5-C(CH₃)₃ | 4-Cl |
| 5-Phenyl | 3-Cl |
| 4-CH₃ | 6-Br |
| 4-CH₂CH₃ | 5-Br |
| 4-CH(CH₃)₂ | 4-Br |
| 4-C(CH₃)₃ | 3-Br |
| 4-Phenyl | 5-CF₃ |
| 5-CH₃, 6-Phenyl | 4-CF₃ |
| 3-CF₃ | 3,4,5,6-F₄ |
| 3,5-Cl₂ | 3,5-Cl₂, 4,6-F₂ |
| 3,5-(CF₃)₂ | 3,4,5,6-Cl₄ |
| 3,6-(CF₃)₂ | 6-Cl, 3,5-(CH₃)₂ |
| 4,5-(CF₃)₂ | 6-OCH₃ |
| 4,6-(CF₃)₂ | 6-OC₂H₅ |
| 3-Cl, 5-CF₃ | 6-OCH(CH₃)₂ |
| 3-Br, 5-CF₃ | 5-OCH₃ |
| 5-Cl, 3-CF₃ | 5-OC₂H₅ |

TABLE 18-continued

| (R¹⁶)q | (R¹⁶)q |
|---|---|
| 6-Cl, 3-CF₃ | 5-OCH(CH₃)₂ |
| 6-Cl, 4-CF₃ | 4-OCH₃ |
| 6-Cl, 5-CF₃ | 4-OC₂H₅ |
| 3,5,6-F₃ | 4-OCH(CH₃)₂ |
| 3,5,6-F₃, 4-CH₃ | |

TABLE 19

| B | R⁵ | R⁶ | R⁷ | i | (R¹⁶)q |
|---|---|---|---|---|---|
| O | H | H | H | 0 | H |
| O | H | H | H | 1 | H |
| O | H | H | H | 2 | H |
| O | H | H | H | 3 | H |
| O | H | H | H | 4 | H |
| O | H | H | H | 5 | H |
| O | H | H | H | 6 | H |
| NH | H | H | H | 0 | H |
| NH | H | H | H | 1 | H |
| NH | H | H | H | 2 | H |
| NH | H | H | H | 3 | H |
| NH | H | H | H | 4 | H |
| S | H | H | H | 0 | H |
| S | H | H | H | 1 | H |
| S | H | H | H | 2 | H |
| S | H | H | H | 3 | H |
| NH | H | H | H | 5 | H |
| NH | H | H | H | 6 | H |
| S | H | H | H | 4 | H |
| S | H | H | H | 5 | H |
| S | H | H | H | 6 | H |
| O | H | H | H | 0 | 5-Cl |
| O | H | H | H | 1 | 5-Cl |
| O | H | H | H | 2 | 5-Cl |
| O | H | H | H | 3 | 5-Cl |
| O | H | H | H | 4 | 5-Cl |
| O | H | H | H | 5 | 5-Cl |
| O | H | H | H | 6 | 5-Cl |
| NH | H | H | H | 0 | 5-Cl |
| NH | H | H | H | 1 | 5-Cl |
| NH | H | H | H | 2 | 5-Cl |
| NH | H | H | H | 3 | 5-Cl |
| NH | H | H | H | 4 | 5-Cl |
| NH | H | H | H | 5 | 5-Cl |
| NH | H | H | H | 6 | 5-Cl |
| S | H | H | H | 0 | 5-Cl |
| S | H | H | H | 1 | 5-Cl |
| S | H | H | H | 2 | 5-Cl |
| S | H | H | H | 3 | 5-Cl |
| S | H | H | H | 4 | 5-Cl |
| S | H | H | H | 5 | 5-Cl |
| S | H | H | H | 6 | 5-Cl |
| N-CH₃ | H | H | H | 0 | 5-Cl |
| N-CH₃ | H | H | H | 1 | 5-Cl |
| N-CH₃ | H | H | H | 2 | 5-Cl |
| N-CH₃ | H | H | H | 3 | 5-Cl |
| N-CH₃ | H | H | H | 4 | 5-Cl |
| N-CH₃ | H | H | H | 5 | 5-Cl |
| N-CH₃ | H | H | H | 6 | 5-Cl |
| NH | H | H | H | 0 | 5-CH₃ |
| NH | H | H | H | 1 | 5-CH₃ |

TABLE 19-continued

| B | R⁵ | R⁶ | R⁷ | i | (R¹⁶)q |
|---|---|---|---|---|---|
| NH | H | H | H | 2 | 5-CH₃ |
| NH | H | H | H | 3 | 5-CH₃ |
| NH | H | H | H | 4 | 5-CH₃ |
| NH | H | H | H | 5 | 5-CH₃ |
| NH | H | H | H | 6 | 5-CH₃ |
| O | H | H | H | 0 | 5-CH₃ |
| O | H | H | H | 1 | 5-CH₃ |
| O | H | H | H | 2 | 5-CH₃ |
| O | H | H | H | 3 | 5-CH₃ |
| O | H | H | H | 4 | 5-CH₃ |
| O | H | H | H | 5 | 5-CH₃ |
| O | H | H | H | 6 | 5-CH₃ |
| S | H | H | H | 0 | 5-CH₃ |
| S | H | H | H | 1 | 5-CH₃ |
| S | H | H | H | 2 | 5-CH₃ |
| S | H | H | H | 3 | 5-CH₃ |
| S | H | H | H | 4 | 5-CH₃ |
| S | H | H | H | 5 | 5-CH₃ |
| S | H | H | H | 6 | 5-CH₃ |
| NH | H | H | H | 0 | 5-Br |
| NH | H | H | H | 1 | 5-Br |
| NH | H | H | H | 2 | 5-Br |
| NH | H | H | H | 3 | 5-Br |
| NH | H | H | H | 4 | 5-Br |
| NH | H | H | H | 5 | 5-Br |
| NH | H | H | H | 6 | 5-Br |
| O | H | H | H | 0 | 5-Br |
| O | H | H | H | 1 | 5-Br |
| O | H | H | H | 2 | 5-Br |
| O | H | H | H | 3 | 5-Br |
| O | H | H | H | 4 | 5-Br |
| O | H | H | H | 5 | 5-Br |
| O | H | H | H | 6 | 5-Br |
| S | H | H | H | 0 | 5-Br |
| S | H | H | H | 1 | 5-Br |
| S | H | H | H | 2 | 5-Br |
| S | H | H | H | 3 | 5-Br |
| S | H | H | H | 4 | 5-Br |
| S | H | H | H | 5 | 5-Br |
| S | H | H | H | 6 | 5-Br |
| NH | H | H | H | 0 | 3-Cl, 5-CF₃ |
| NH | H | H | H | 1 | 3-Cl, 5-CF₃ |
| NH | H | H | H | 2 | 3-Cl, 5-CF₃ |
| NH | H | H | H | 3 | 3-Cl, 5-CF₃ |
| NH | H | H | H | 4 | 3-Cl, 5-CF₃ |
| NH | H | H | H | 5 | 3-Cl, 5-CF₃ |
| NH | H | H | H | 6 | 3-Cl, 5-CF₃ |
| O | H | H | H | 0 | 3-Cl, 5-CF₃ |
| O | H | H | H | 1 | 3-Cl, 5-CF₃ |
| O | H | H | H | 2 | 3-Cl, 5-CF₃ |
| O | H | H | H | 3 | 3-Cl, 5-CF₃ |
| O | H | H | H | 4 | 3-Cl, 5-CF₃ |
| O | H | H | H | 5 | 3-Cl, 5-CF₃ |
| O | H | H | H | 6 | 3-Cl, 5-CF₃ |
| S | H | H | H | 0 | 3-Cl, 5-CF₃ |
| S | H | H | H | 1 | 3-Cl, 5-CF₃ |
| S | H | H | H | 2 | 3-Cl, 5-CF₃ |
| S | H | H | H | 3 | 3-Cl, 5-CF₃ |
| S | H | H | H | 4 | 3-Cl, 5-CF₃ |
| S | H | H | H | 5 | 3-Cl, 5-CF₃ |
| S | H | H | H | 6 | 3-Cl, 5-CF₃ |
| O | H | H | H | 0 | 5-NO₂ |
| O | H | H | H | 1 | 5-NO₂ |
| O | H | H | H | 2 | 5-NO₂ |
| O | H | H | H | 3 | 5-NO₂ |
| O | H | H | H | 4 | 5-NO₂ |
| O | H | H | H | 5 | 5-NO₂ |
| O | H | H | H | 6 | 5-NO₂ |
| O | H | H | H | 0 | 3-NO₂, 5-Br |
| O | H | H | H | 1 | 3-NO₂, 5-Br |
| O | H | H | H | 2 | 3-NO₂, 5-Br |
| O | H | H | H | 3 | 3-NO₂, 5-Br |
| O | H | H | H | 4 | 3-NO₂, 5-Br |
| O | H | H | H | 5 | 3-NO₂, 5-Br |
| O | H | H | H | 6 | 3-NO₂, 5-Br |
| O | H | H | H | 0 | 3-NO₂, 4-CH₃ |
| O | H | H | H | 1 | 3-NO₂, 4-CH₃ |
| O | H | H | H | 2 | 3-NO₂, 4-CH₃ |
| O | H | H | H | 3 | 3-NO₂, 4-CH₃ |
| O | H | H | H | 4 | 3-NO₂, 4-CH₃ |
| O | H | H | H | 5 | 3-NO₂, 4-CH₃ |
| O | H | H | H | 6 | 3-NO₂, 4-CH₃ |
| O | H | H | H | 0 | 4-CH₃, 5-NO₂ |
| O | H | H | H | 1 | 4-CH₃, 5-NO₂ |
| O | H | H | H | 2 | 4-CH₃, 5-NO₂ |
| O | H | H | H | 3 | 4-CH₃, 5-NO₂ |
| O | H | H | H | 4 | 4-CH₃, 5-NO₂ |
| O | H | H | H | 5 | 4-CH₃, 5-NO₂ |
| O | H | H | H | 6 | 4-CH₃, 5-NO₂ |
| O | H | H | H | 0 | 5-CF₃ |
| O | H | H | H | 1 | 5-CF₃ |
| O | H | H | H | 2 | 5-CF₃ |
| O | H | H | H | 3 | 5-CF₃ |
| O | H | H | H | 4 | 5-CF₃ |
| O | H | H | H | 5 | 5-CF₃ |
| O | H | H | H | 6 | 5-CF₃ |
| S | H | H | H | 0 | 5-CF₃ |
| S | H | H | H | 1 | 5-CF₃ |
| S | H | H | H | 2 | 5-CF₃ |
| S | H | H | H | 3 | 5-CF₃ |
| S | H | H | H | 4 | 5-CF₃ |
| S | H | H | H | 5 | 5-CF₃ |
| S | H | H | H | 6 | 5-CF₃ |
| NH | H | H | H | 0 | 5-CF₃ |
| NH | H | H | H | 1 | 5-CF₃ |
| NH | H | H | H | 2 | 5-CF₃ |
| NH | H | H | H | 3 | 5-CF₃ |
| NH | H | H | H | 4 | 5-CF₃ |
| NH | H | H | H | 5 | 5-CF₃ |
| NH | H | H | H | 6 | 5-CF₃ |
| N(CH₃) | H | H | H | 0 | 5-CF₃ |
| N(CH₃) | H | H | H | 1 | 5-CF₃ |
| N(CH₃) | H | H | H | 2 | 5-CF₃ |
| N(CH₃) | H | H | H | 3 | 5-CF₃ |
| N(CH₃) | H | H | H | 4 | 5-CF₃ |
| N(CH₃) | H | H | H | 5 | 5-CF₃ |
| N(CH₃) | H | H | H | 6 | 5-CF₃ |
| C(=O)O | H | H | H | 0 | H |
| C(=O)O | H | H | H | 1 | H |
| C(=O)O | H | H | H | 2 | H |
| C(=O)O | H | H | H | 3 | H |
| C(=O)O | H | H | H | 4 | H |
| C(=O)O | H | H | H | 5 | H |
| C(=O)O | H | H | H | 6 | H |
| C(=O)NH | H | H | H | 0 | H |
| C(=O)NH | H | H | H | 1 | H |
| C(=O)NH | H | H | H | 2 | H |
| C(=O)NH | H | H | H | 3 | H |
| C(=O)NH | H | H | H | 4 | H |
| C(=O)NH | H | H | H | 5 | H |
| C(=O)NH | H | H | H | 6 | H |
| NHC(=O) | H | H | H | 0 | H |
| NHC(=O) | H | H | H | 1 | H |
| NHC(=O) | H | H | H | 2 | H |
| NHC(=O) | H | H | H | 3 | H |
| NHC(=O) | H | H | H | 4 | H |
| NHC(=O) | H | H | H | 5 | H |
| NHC(=O) | H | H | H | 6 | H |

TABLE 19-continued

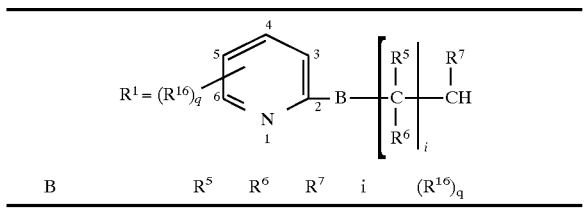

| B | R⁵ | R⁶ | R⁷ | i | (R¹⁶)q |
|---|---|---|---|---|---|
| NHC(=O) | H | H | H | 0 | 5-CF₃ |
| NHC(=O) | H | H | H | 1 | 5-CF₃ |
| NHC(=O) | H | H | H | 2 | 5-CF₃ |
| NHC(=O) | H | H | H | 3 | 5-CF₃ |
| NHC(=O) | H | H | H | 4 | 5-CF₃ |
| NHC(=O) | H | H | H | 5 | 5-CF₃ |
| NHC(=O) | H | H | H | 6 | 5-CF₃ |
| C(=O)O | H | H | H | 0 | 5-CF₃ |
| C(=O)O | H | H | H | 1 | 5-CF₃ |
| C(=O)O | H | H | H | 2 | 5-CF₃ |
| C(=O)O | H | H | H | 3 | 5-CF₃ |
| C(=O)O | H | H | H | 4 | 5-CF₃ |
| C(=O)O | H | H | H | 5 | 5-CF₃ |
| C(=O)O | H | H | H | 6 | 5-CF₃ |
| C(=O)NH | H | H | H | 0 | 5-CF₃ |
| C(=O)NH | H | H | H | 1 | 5-CF₃ |
| C(=O)NH | H | H | H | 2 | 5-CF₃ |
| C(=O)NH | H | H | H | 3 | 5-CF₃ |
| C(=O)NH | H | H | H | 4 | 5-CF₃ |
| C(=O)NH | H | H | H | 5 | 5-CF₃ |
| C(=O)NH | H | H | H | 6 | 5-CF₃ |
| N(CH₃) | H | H | H | 0 | H |
| N(CH₃) | H | H | H | 1 | H |
| N(CH₃) | H | H | H | 2 | H |
| N(CH₃) | H | H | H | 3 | H |
| N(CH₃) | H | H | H | 4 | H |
| N(CH₃) | H | H | H | 5 | H |
| N(CH₃) | H | H | H | 6 | H |
| OC(=O) | H | H | H | 0 | H |
| OC(=O) | H | H | H | 1 | H |
| OC(=O) | H | H | H | 2 | H |
| OC(=O) | H | H | H | 3 | H |
| OC(=O) | H | H | H | 4 | H |
| OC(=O) | H | H | H | 5 | H |
| OC(=O) | H | H | H | 6 | H |
| C(=O)O | H | H | H | 0 | 5-Cl |
| C(=O)O | H | H | H | 1 | 5-Cl |
| C(=O)O | H | H | H | 2 | 5-Cl |
| C(=O)O | H | H | H | 3 | 5-Cl |
| C(=O)O | H | H | H | 4 | 5-Cl |
| C(=O)O | H | H | H | 5 | 5-Cl |
| C(=O)O | H | H | H | 6 | 5-Cl |
| C(=O)NH | H | H | H | 0 | 5-Cl |
| C(=O)NH | H | H | H | 1 | 5-Cl |
| C(=O)NH | H | H | H | 2 | 5-Cl |
| C(=O)NH | H | H | H | 3 | 5-Cl |
| C(=O)NH | H | H | H | 4 | 5-Cl |
| C(=O)NH | H | H | H | 5 | 5-Cl |
| C(=O)NH | H | H | H | 6 | 5-Cl |
| NHC(=O) | H | H | H | 0 | 5-Cl |
| NHC(=O) | H | H | H | 1 | 5-Cl |
| NHC(=O) | H | H | H | 2 | 5-Cl |
| NHC(=O) | H | H | H | 3 | 5-Cl |
| NHC(=O) | H | H | H | 4 | 5-Cl |
| NHC(=O) | H | H | H | 5 | 5-Cl |
| NHC(=O) | H | H | H | 6 | 5-Cl |
| N(CH₃) | H | H | H | 0 | 5-CH₃ |
| N(CH₃) | H | H | H | 1 | 5-CH₃ |
| N(CH₃) | H | H | H | 2 | 5-CH₃ |
| N(CH₃) | H | H | H | 3 | 5-CH₃ |
| N(CH₃) | H | H | H | 4 | 5-CH₃ |
| N(CH₃) | H | H | H | 5 | 5-CH₃ |
| N(CH₃) | H | H | H | 6 | 5-CH₃ |
| C(=O)O | H | H | H | 0 | 5-CH₃ |
| C(=O)O | H | H | H | 1 | 5-CH₃ |
| C(=O)O | H | H | H | 2 | 5-CH₃ |
| C(=O)O | H | H | H | 3 | 5-CH₃ |
| C(=O)O | H | H | H | 4 | 5-CH₃ |
| C(=O)O | H | H | H | 5 | 5-CH₃ |

TABLE 19-continued

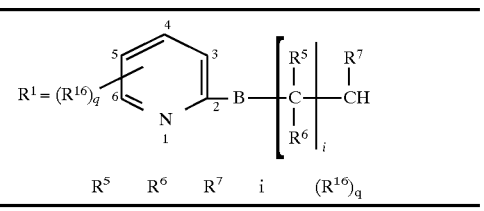

| B | R⁵ | R⁶ | R⁷ | i | (R¹⁶)q |
|---|---|---|---|---|---|
| C(=O)O | H | H | H | 6 | 5-CH₃ |
| C(=O)NH | H | H | H | 0 | 5-CH₃ |
| C(=O)NH | H | H | H | 1 | 5-CH₃ |
| C(=O)NH | H | H | H | 2 | 5-CH₃ |
| C(=O)NH | H | H | H | 3 | 5-CH₃ |
| C(=O)NH | H | H | H | 4 | 5-CH₃ |
| C(=O)NH | H | H | H | 5 | 5-CH₃ |
| C(=O)NH | H | H | H | 6 | 5-CH₃ |
| NHC(=O) | H | H | H | 0 | 5-CH₃ |
| NHC(=O) | H | H | H | 1 | 5-CH₃ |
| NHC(=O) | H | H | H | 2 | 5-CH₃ |
| NHC(=O) | H | H | H | 3 | 5-CH₃ |
| NHC(=O) | H | H | H | 4 | 5-CH₃ |
| NHC(=O) | H | H | H | 5 | 5-CH₃ |
| NHC(=O) | H | H | H | 6 | 5-CH₃ |
| C(=O)O | H | H | H | 0 | 3-Cl, 5-CF₃ |
| C(=O)O | H | H | H | 1 | 3-Cl, 5-CF₃ |
| C(=O)O | H | H | H | 2 | 3-Cl, 5-CF₃ |
| C(=O)O | H | H | H | 3 | 3-Cl, 5-CF₃ |
| C(=O)O | H | H | H | 4 | 3-Cl, 5-CF₃ |
| C(=O)O | H | H | H | 5 | 3-Cl, 5-CF₃ |
| C(=O)O | H | H | H | 6 | 3-Cl, 5-CF₃ |
| C(=O)NH | H | H | H | 0 | 3-Cl, 5-CF₃ |
| C(=O)NH | H | H | H | 1 | 3-Cl, 5-CF₃ |
| C(=O)NH | H | H | H | 2 | 3-Cl, 5-CF₃ |
| C(=O)NH | H | H | H | 3 | 3-Cl, 5-CF₃ |
| C(=O)NH | H | H | H | 4 | 3-Cl, 5-CF₃ |
| C(=O)NH | H | H | H | 5 | 3-Cl, 5-CF₃ |
| C(=O)NH | H | H | H | 6 | 3-Cl, 5-CF₃ |
| C(=O)N(CH₃) | H | H | H | 0 | 3-Cl, 5-CF₃ |
| C(=O)N(CH₃) | H | H | H | 1 | 3-Cl, 5-CF₃ |
| C(=O)N(CH₃) | H | H | H | 2 | 3-Cl, 5-CF₃ |
| C(=O)N(CH₃) | H | H | H | 3 | 3-Cl, 5-CF₃ |
| C(=O)N(CH₃) | H | H | H | 4 | 3-Cl, 5-CF₃ |
| C(=O)N(CH₃) | H | H | H | 5 | 3-Cl, 5-CF₃ |
| C(=O)N(CH₃) | H | H | H | 6 | 3-Cl, 5-CF₃ |
| NHC(=O) | H | H | H | 0 | 3-Cl, 5-CF₃ |
| NHC(=O) | H | H | H | 1 | 3-Cl, 5-CF₃ |
| NHC(=O) | H | H | H | 2 | 3-Cl, 5-CF₃ |
| NHC(=O) | H | H | H | 3 | 3-Cl, 5-CF₃ |
| NHC(=O) | H | H | H | 4 | 3-Cl, 5-CF₃ |
| NHC(=O) | H | H | H | 5 | 3-Cl, 5-CF₃ |
| NHC(=O) | H | H | H | 6 | 3-Cl, 5-CF₃ |
| O | H | H | H | 0 | 3-Br, 5-CF₃ |
| O | H | H | H | 1 | 3-Br, 5-CF₃ |
| O | H | H | H | 2 | 3-Br, 5-CF₃ |
| O | H | H | H | 3 | 3-Br, 5-CF₃ |
| O | H | H | H | 4 | 3-Br, 5-CF₃ |
| O | H | H | H | 5 | 3-Br, 5-CF₃ |
| O | H | H | H | 6 | 3-Br, 5-CF₃ |
| S | H | H | H | 0 | 3-Br, 5-CF₃ |
| S | H | H | H | 1 | 3-Br, 5-CF₃ |
| S | H | H | H | 2 | 3-Br, 5-CF₃ |
| S | H | H | H | 3 | 3-Br, 5-CF₃ |
| S | H | H | H | 4 | 3-Br, 5-CF₃ |
| S | H | H | H | 5 | 3-Br, 5-CF₃ |
| S | H | H | H | 6 | 3-Br, 5-CF₃ |
| NH | H | H | H | 0 | 3-Br, 5-CF₃ |
| NH | H | H | H | 1 | 3-Br, 5-CF₃ |
| NH | H | H | H | 2 | 3-Br, 5-CF₃ |
| NH | H | H | H | 3 | 3-Br, 5-CF₃ |
| NH | H | H | H | 4 | 3-Br, 5-CF₃ |
| NH | H | H | H | 5 | 3-Br, 5-CF₃ |
| NH | H | H | H | 6 | 3-Br, 5-CF₃ |
| N(CH₃) | H | H | H | 0 | 3-Br, 5-CF₃ |
| N(CH₃) | H | H | H | 1 | 3-Br, 5-CF₃ |
| N(CH₃) | H | H | H | 2 | 3-Br, 5-CF₃ |
| N(CH₃) | H | H | H | 3 | 3-Br, 5-CF₃ |
| N(CH₃) | H | H | H | 4 | 3-Br, 5-CF₃ |

TABLE 19-continued $R^1 = (R^{16})_q$ — pyridine (positions 2,3,4,5,6 with N=1) — $B-[C(R^5)(R^6)]_i-CH(R^7)$

| B | $R^5$ | $R^6$ | $R^7$ | i | $(R^{16})_q$ |
|---|---|---|---|---|---|
| N(CH$_3$) | H | H | H | 5 | 3-Br, 5-CF$_3$ |
| N(CH$_3$) | H | H | H | 6 | 3-Br, 5-CF$_3$ |
| C(=O)O | H | H | H | 0 | 3-Br, 5-CF$_3$ |
| C(=O)O | H | H | H | 1 | 3-Br, 5-CF$_3$ |
| C(=O)O | H | H | H | 2 | 3-Br, 5-CF$_3$ |
| C(=O)O | H | H | H | 3 | 3-Br, 5-CF$_3$ |
| C(=O)O | H | H | H | 4 | 3-Br, 5-CF$_3$ |
| C(=O)O | H | H | H | 5 | 3-Br, 5-CF$_3$ |
| C(=O)O | H | H | H | 6 | 3-Br, 5-CF$_3$ |
| C(=O)NH | H | H | H | 0 | 3-Br, 5-CF$_3$ |
| C(=O)NH | H | H | H | 1 | 3-Br, 5-CF$_3$ |
| C(=O)NH | H | H | H | 2 | 3-Br, 5-CF$_3$ |
| C(=O)NH | H | H | H | 3 | 3-Br, 5-CF$_3$ |
| C(=O)NH | H | H | H | 4 | 3-Br, 5-CF$_3$ |
| C(=O)NH | H | H | H | 5 | 3-Br, 5-CF$_3$ |
| C(=O)NH | H | H | H | 6 | 3-Br, 5-CF$_3$ |
| C(=O)NCH$_3$ | H | H | H | 0 | 3-Br, 5-CF$_3$ |
| C(=O)NCH$_3$ | H | H | H | 1 | 3-Br, 5-CF$_3$ |
| C(=O)NCH$_3$ | H | H | H | 2 | 3-Br, 5-CF$_3$ |
| C(=O)NCH$_3$ | H | H | H | 3 | 3-Br, 5-CF$_3$ |
| C(=O)NCH$_3$ | H | H | H | 4 | 3-Br, 5-CF$_3$ |
| C(=O)NCH$_3$ | H | H | H | 5 | 3-Br, 5-CF$_3$ |
| C(=O)NCH$_3$ | H | H | H | 6 | 3-Br, 5-CF$_3$ |
| NHC(=O) | H | H | H | 0 | 3-Br, 5-CF$_3$ |
| NHC(=O) | H | H | H | 1 | 3-Br, 5-CF$_3$ |
| NHC(=O) | H | H | H | 2 | 3-Br, 5-CF$_3$ |
| NHC(=O) | H | H | H | 3 | 3-Br, 5-CF$_3$ |
| NHC(=O) | H | H | H | 4 | 3-Br, 5-CF$_3$ |
| NHC(=O) | H | H | H | 5 | 3-Br, 5-CF$_3$ |
| NHC(=O) | H | H | H | 6 | 3-Br, 5-CF$_3$ |
| O | H | H | H | 0 | 3,5-(CF$_3$)$_2$ |
| O | H | H | H | 1 | 3,5-(CF$_3$)$_2$ |
| O | H | H | H | 2 | 3,5-(CF$_3$)$_2$ |
| O | H | H | H | 3 | 3,5-(CF$_3$)$_2$ |
| O | H | H | H | 4 | 3,5-(CF$_3$)$_2$ |
| O | H | H | H | 5 | 3,5-(CF$_3$)$_2$ |
| O | H | H | H | 6 | 3,5-(CF$_3$)$_2$ |
| S | H | H | H | 0 | 3,5-(CF$_3$)$_2$ |
| S | H | H | H | 1 | 3,5-(CF$_3$)$_2$ |
| S | H | H | H | 2 | 3,5-(CF$_3$)$_2$ |
| S | H | H | H | 3 | 3,5-(CF$_3$)$_2$ |
| S | H | H | H | 4 | 3,5-(CF$_3$)$_2$ |
| S | H | H | H | 5 | 3,5-(CF$_3$)$_2$ |
| S | H | H | H | 6 | 3,5-(CF$_3$)$_2$ |
| NH | H | H | H | 0 | 3,5-(CF$_3$)$_2$ |
| NH | H | H | H | 1 | 3,5-(CF$_3$)$_2$ |
| NH | H | H | H | 2 | 3,5-(CF$_3$)$_2$ |
| NH | H | H | H | 3 | 3,5-(CF$_3$)$_2$ |
| NH | H | H | H | 4 | 3,5-(CF$_3$)$_2$ |
| NH | H | H | H | 5 | 3,5-(CF$_3$)$_2$ |
| NH | H | H | H | 6 | 3,5-(CF$_3$)$_2$ |
| N(CH$_3$) | H | H | H | 0 | 3,5-(CF$_3$)$_2$ |
| N(CH$_3$) | H | H | H | 1 | 3,5-(CF$_3$)$_2$ |
| N(CH$_3$) | H | H | H | 2 | 3,5-(CF$_3$)$_2$ |
| N(CH$_3$) | H | H | H | 3 | 3,5-(CF$_3$)$_2$ |
| N(CH$_3$) | H | H | H | 4 | 3,5-(CF$_3$)$_2$ |
| N(CH$_3$) | H | H | H | 5 | 3,5-(CF$_3$)$_2$ |
| N(CH$_3$) | H | H | H | 6 | 3,5-(CF$_3$)$_2$ |
| C(=O)O | H | H | H | 0 | 3,5-(CF$_3$)$_2$ |
| C(=O)O | H | H | H | 1 | 3,5-(CF$_3$)$_2$ |
| C(=O)O | H | H | H | 2 | 3,5-(CF$_3$)$_2$ |
| C(=O)O | H | H | H | 3 | 3,5-(CF$_3$)$_2$ |
| C(=O)O | H | H | H | 4 | 3,5-(CF$_3$)$_2$ |
| C(=O)O | H | H | H | 5 | 3,5-(CF$_3$)$_2$ |
| C(=O)O | H | H | H | 6 | 3,5-(CF$_3$)$_2$ |
| C(=O)NH | H | H | H | 0 | 3,5-(CF$_3$)$_2$ |
| C(=O)NH | H | H | H | 1 | 3,5-(CF$_3$)$_2$ |
| C(=O)NH | H | H | H | 2 | 3,5-(CF$_3$)$_2$ |
| C(=O)NH | H | H | H | 3 | 3,5-(CF$_3$)$_2$ |
| C(=O)NH | H | H | H | 4 | 3,5-(CF$_3$)$_2$ |
| C(=O)NH | H | H | H | 5 | 3,5-(CF$_3$)$_2$ |
| C(=O)NH | H | H | H | 6 | 3,5-(CF$_3$)$_2$ |
| C(=O)N(CH$_3$) | H | H | H | 0 | 3,5-(CF$_3$)$_2$ |
| C(=O)N(CH$_3$) | H | H | H | 1 | 3,5-(CF$_3$)$_2$ |
| C(=O)N(CH$_3$) | H | H | H | 2 | 3,5-(CF$_3$)$_2$ |
| C(=O)N(CH$_3$) | H | H | H | 3 | 3,5-(CF$_3$)$_2$ |
| C(=O)N(CH$_3$) | H | H | H | 4 | 3,5-(CF$_3$)$_2$ |
| C(=O)N(CH$_3$) | H | H | H | 5 | 3,5-(CF$_3$)$_2$ |
| C(=O)N(CH$_3$) | H | H | H | 6 | 3,5-(CF$_3$)$_2$ |
| NHC(=O) | H | H | H | 0 | 3,5-(CF$_3$)$_2$ |
| NHC(=O) | H | H | H | 1 | 3,5-(CF$_3$)$_2$ |
| NHC(=O) | H | H | H | 2 | 3,5-(CF$_3$)$_2$ |
| NHC(=O) | H | H | H | 3 | 3,5-(CF$_3$)$_2$ |
| NHC(=O) | H | H | H | 4 | 3,5-(CF$_3$)$_2$ |
| NHC(=O) | H | H | H | 5 | 3,5-(CF$_3$)$_2$ |
| NHC(=O) | H | H | H | 6 | 3,5-(CF$_3$)$_2$ |

TABLE 20

$R^1 =$

- thiophen-2-yl—CONHCH$_2$CH$_2$CH$_2$
- 5-Br-thiophen-2-yl—CONHCH$_2$CH$_2$CH$_2$
- furan-2-yl—CONHCH$_2$CH$_2$CH$_2$
- 5-Br-furan-2-yl—CONHCH$_2$CH$_2$CH$_2$
- 5-CH$_3$-thiophen-2-yl—CONHCH$_2$CH$_2$CH$_2$
- 5-CH$_3$-furan-2-yl—CONHCH$_2$CH$_2$CH$_2$ The process for producing the intermediate in the production of the present compound will be explained below.

The compound represented by Formula VI and the compound represented by Formula [III] can be produced, for example, according to Scheme I.

Starting compounds in Scheme I are commercially available or can be produced, for example, according to processes described in the following references;

J. Org. Chem., 33, 2512, (1968), J. Am. Chem. Soc. 74, 4087 (1952), J. Am. Chem., Soc., 70, 2656 (1948), Chem. Lett., 1987, 627, and Org. Synth., IV 15 (1963), all of which are incorporated herein by reference.

As for protective groups in Scheme I and following Schemes, Protective Groups in Organic Synthesis, Greene and Wuts, 2nd Edition, (1992), John Wiley & Sons, Inc., the complete disclosure of which is incorporated herein by reference.

Scheme I

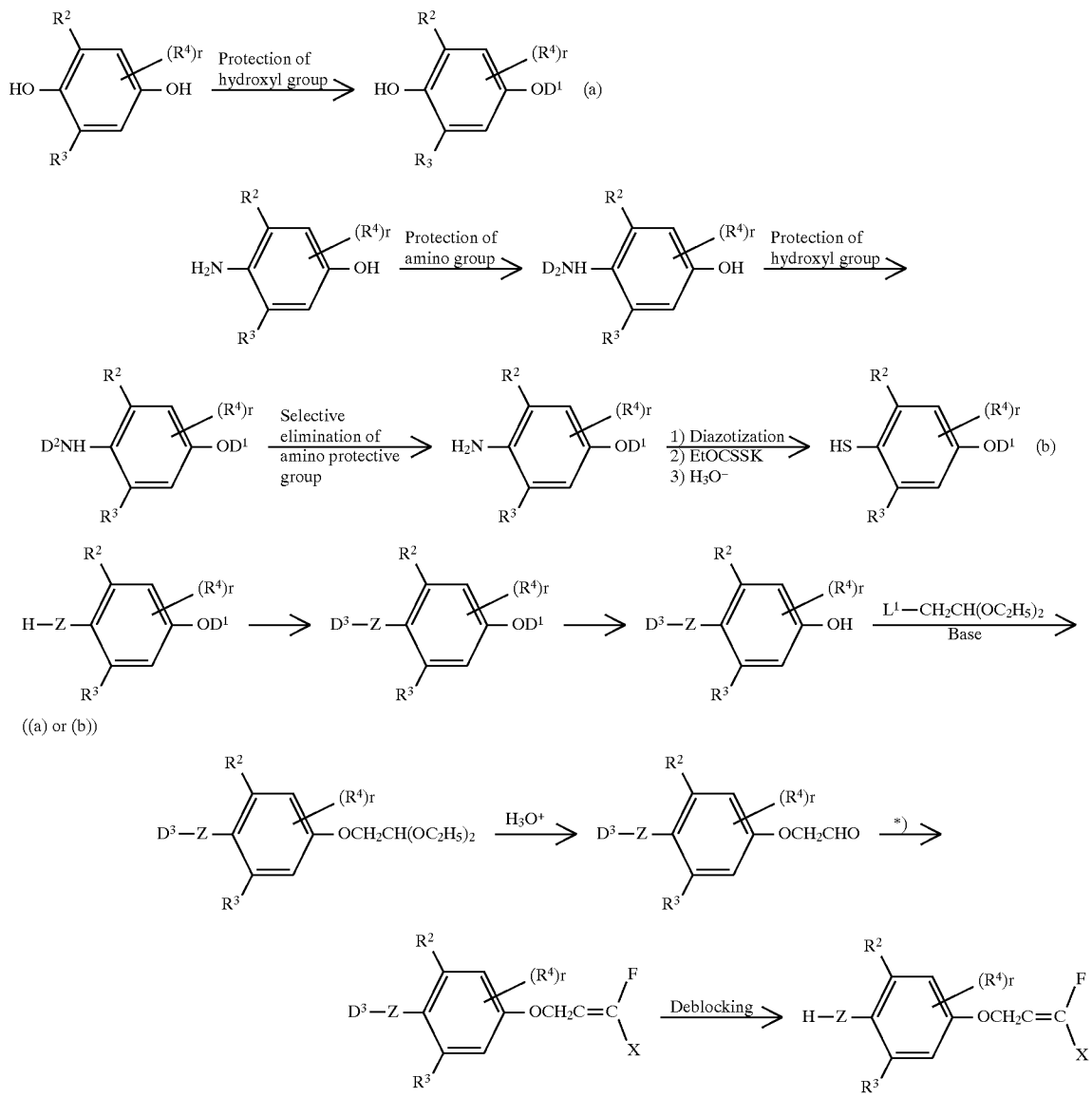

wherein *) represents that the reaction is conducted under the same reaction conditions as those of the above-described production process C, $D^1$, $D^2$ and $D^3$ respectively represent a protective group which can be selectively eliminated (e.g., $D^1$ represents a benzyl group, $D^2$ represents an acetyl group and $D^3$ represents a benzoyl group); and other symbols are as defined above.

The compound represented by Formula VII can be produced, for example, according to Scheme II.

Scheme II

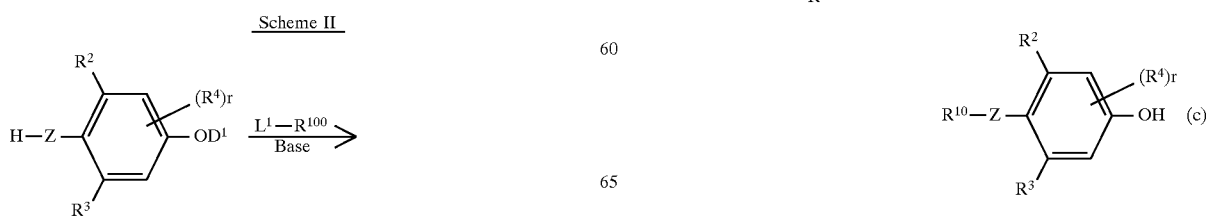

wherein $R^{100}$ represents $R^1$ other than $Q_1$, and other symbols are as defined above.

In Scheme II above, the starting compound can be obtained, for example, according to Scheme I.

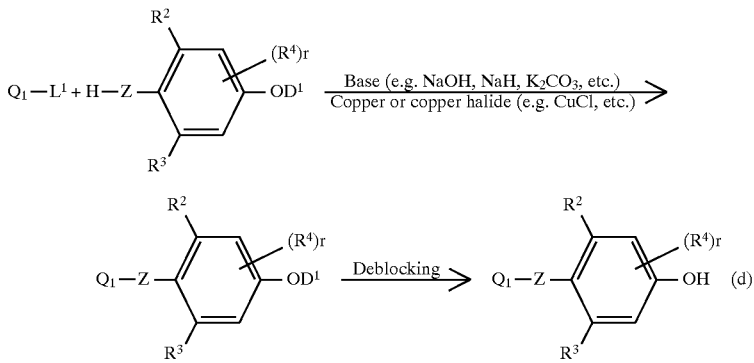

[wherein other symbols are as defined above]

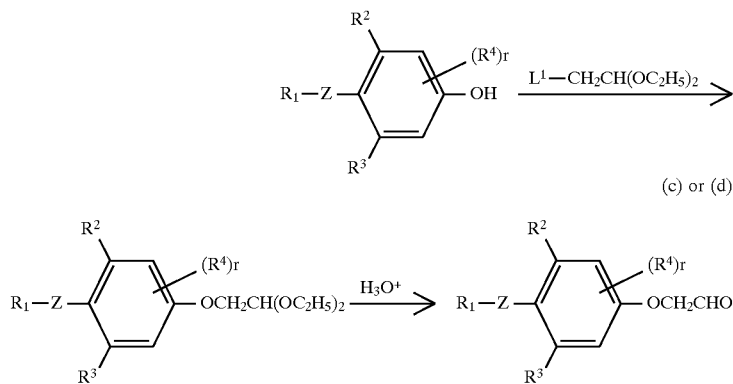

wherein the symbols are as defined above.

The compound wherein $R^1$ is $R_1^1$ ($R_1^1$ represents $Q_2$ or $Q_3$ among $R^1$) among the compounds represented by Formulas IV and V, as the intermediate for production of the present compound, is commercially available or can be produced, for example, by the process of the following Schemes III and IV.

An aldehyde compound represented by the general formula A-CHO (wherein A is as defined above), which can used in the production of the compound represented by Formula V, can be purchased or can be obtained by the process described in the following references, the complete disclosures of which are incorporated herein by reference.

Furancarbaldehyde
  Zh. Org. Khim, 11, 1955;
  Tetrahedron, 39, 3881;
  Chem. Pharm. Bull., 28, 2846, etc.
Thiophenecarbaldehyde
  Tetrahedron, 32, 1403;
  J. Org. Chem., 41, 2835;
  Zh. Obshch. Khin, 34, 4010;
  Bull. Soc. Chim. France., 479 (1963), etc.
Pyrrolecarbaldehyde
  Beilstein, 21, 1279, etc.
Isothiazolecarbaldehyde
  J. Medicin. Chem. 13, 1208;
  J. Chem. Soc., 446 (1964), etc.
Pyrazolecarbaldehyde
  Chem. Ber., 97, 3407;
  J. Chem. Soc., 3314 (1957), etc.
Imidazolecarbaldehyde
  J. Pharm. Soc. Japan., 60, 184;
  J. Amer. Chem. Soc., 71, 2444, etc.
Thiazolecarbaldehyde
  Japanese Patent Kokai (Laid-Open) No. 59-206370;
  Chem. Ab., 62, 7764d;
  Chem. Ber., 101, 3872;
  Japanese Patent Kokal (Laid-Open) No. 59-206370;
Thiadiazolecarbaldehyde
  U.S. Pat. No. 1,113,705 (the complete disclosure of which is incorporated herein by reference).

Scheme III ($R_1^1 = Q_2$ and $i = 0$)

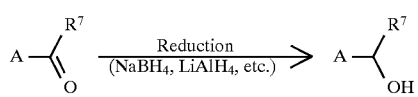

($R_1^1$—OH when $i = 0$)

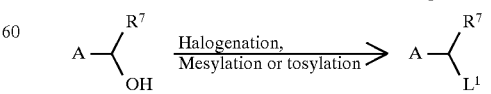

($R_1^1$—$L^1$ when $i = 0$)

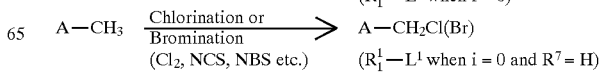

($R_1^1$—$L^1$ when $i = 0$ and $R^7 = H$)

-continued
Scheme III

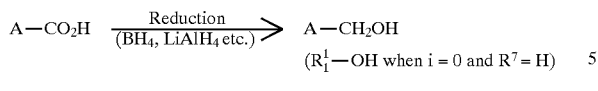

(R$_1^1$—OH when i = 0 and R$^7$ = H)

wherein the symbols are as defined above.

Scheme IV (R$_1^1$=Q, i ≧ 1)

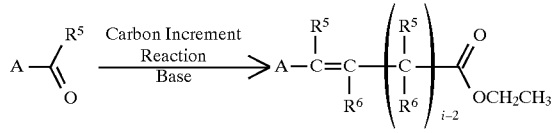

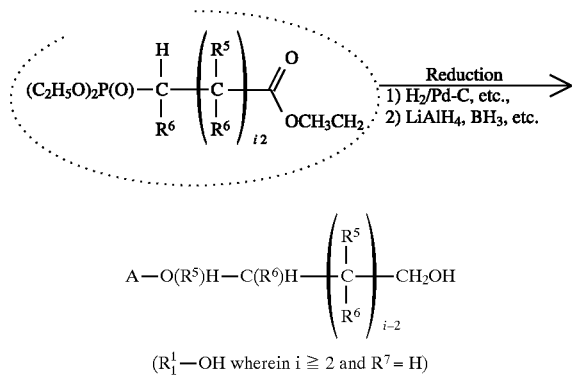

(R$_1^1$—OH wherein i ≧ 2 and R$^7$ = H)

*)Chem. Ber. 95, 581 (1962) etc. (the complete disclosure of which is incorporated herein by reference).

-continued
Scheme IV

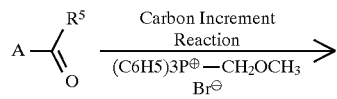

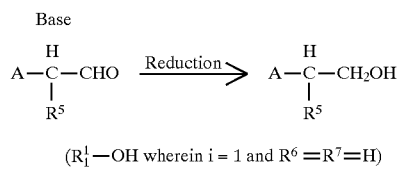

(R$_1^1$—OH wherein i = 1 and R$^6$ = R$^7$ = H)

wherein the symbols sre as defined above. The compound represented by A-L$^4$ (whoretti L$^4$ represents a halogen atom (e.g. chlorine atotn. hromine atom, iodine atom, etc.) among the compound represented by Formula X as the intermediate for production of the present compound, is commercially available or can be produced, for example, by the following process.

Scheme V

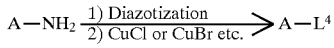

wherein A and L$^4$ are as defined above

The compounds represented by Formulas IX, XI and XIII, as the intermediate for production of the present compound, can be produced, for example, according to Schemes VI to IX.

Scheme VI

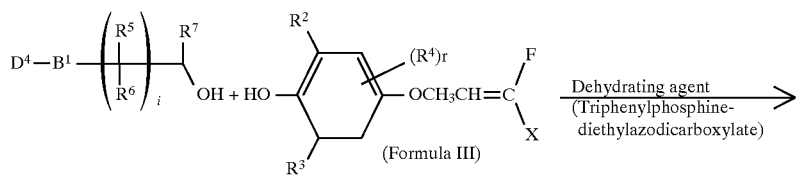

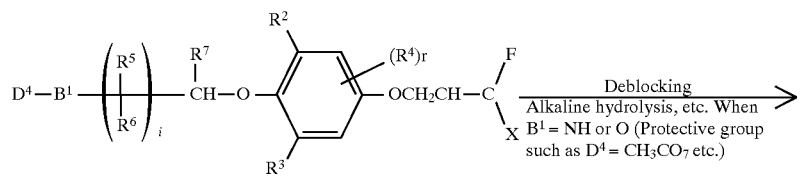

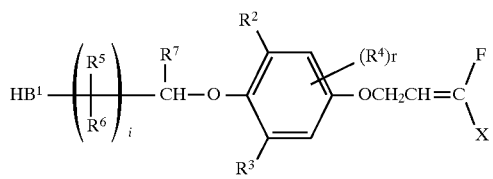

(Formula IX; Formula XI wherein B$^1$ = 0)

-continued
Scheme VI
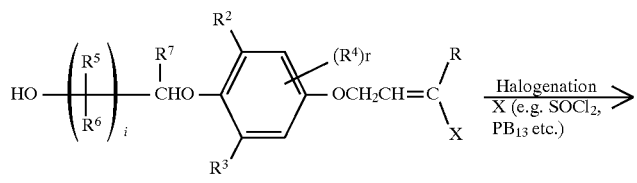
(Formula XI; Formula IX wherein $B^1 = 0$)
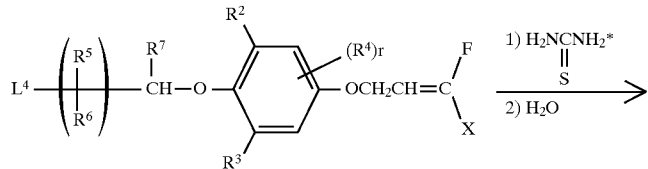
(Formula XIII wherein $L^1 = L^4$)
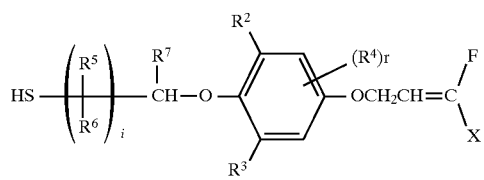
(Formula IX wherein $B^1 = S$)
wherein the symbols are as defined above.
*) J. Amer. Chem. Soc., 33, 440 (1905), the complete disclosure of which is incorporated herein by reference.
Scheme VII
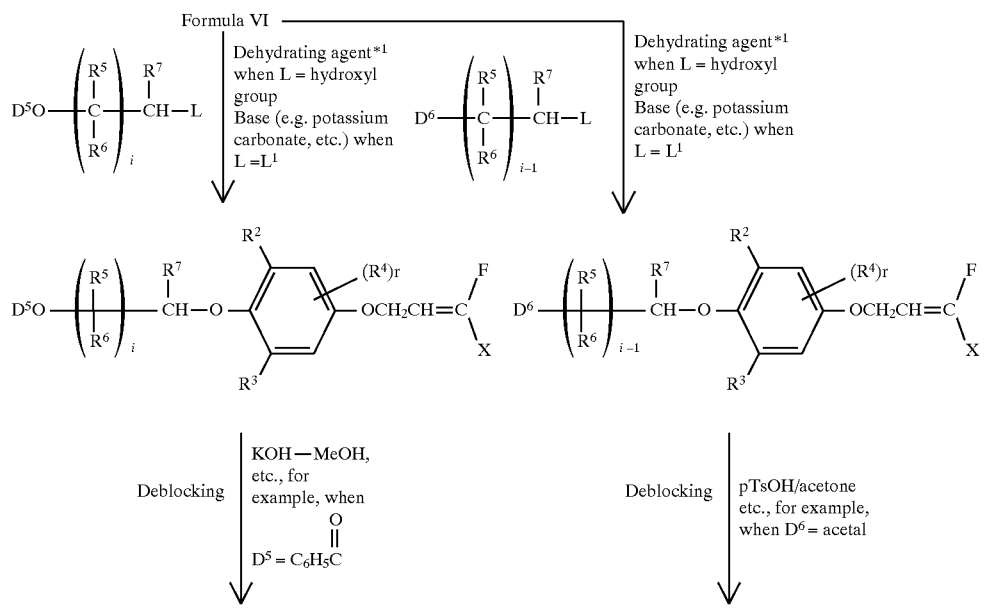

Scheme VII

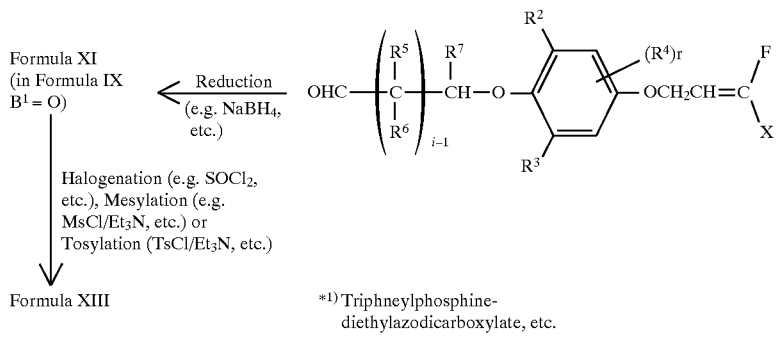

Formula XI (in Formula IX $B^1$ = O) — Reduction (e.g. NaBH$_4$, etc.) →

Halogenation (e.g. SOCl$_2$, etc.), Mesylation (e.g. MsCl/Et$_3$N, etc.) or Tosylation (TsCl/Et$_3$N, etc.)

↓

Formula XIII

*1) Triphneylphosphine-diethylazodicarboxylate, etc.

wherein $M_s$ represents a mesyl group, $T_s$ represents a tosyl group; $D^5$ represents a protective group of an alcohol (e.g. benzoyl group, etc.); $D^6$ represents a protected group of a formyl group (e.g. acetal group, etc.); L represents a hydroxyl group or $L^1$; and $R^2$, $R^3$, $R^4$, $R^5$, $R^6$, $R^7$, r, X, $L^1$ and i are as defined above.

wherein the symbols are as defined above.

The compound represented by Formula XV can be produced, for example, according to Scheme IX.

Scheme VIII

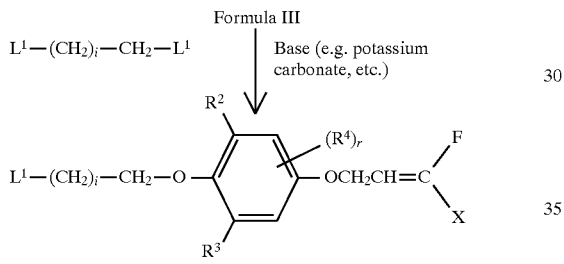

(in Formula XIII, $R^2$ = $R^3$ = $R^4$ = H)

Scheme IX

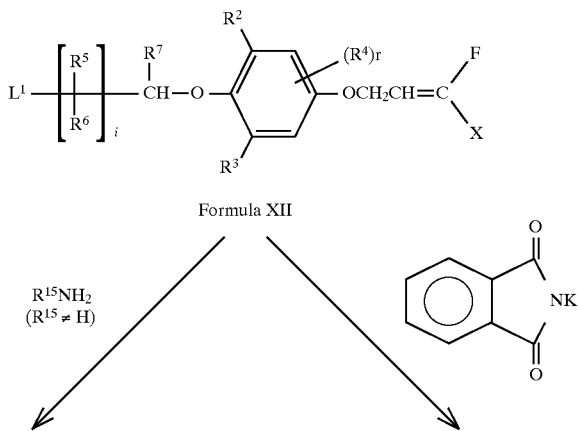

-continued
Scheme IX

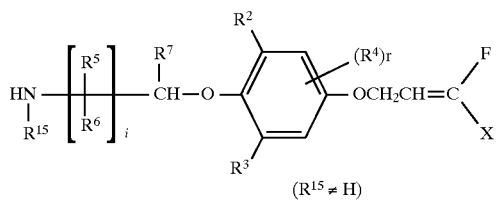
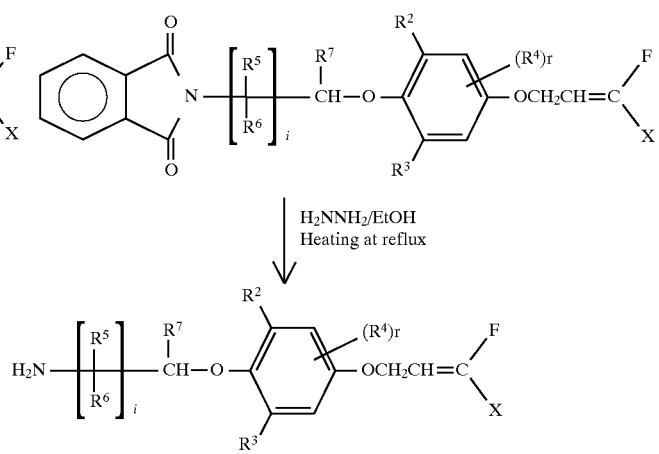

wherein the symbols are as defined above.

The present compounds are satisfactorily effective for the control of various noxious insects, mites and ticks, examples of which are as follows:

Hemiptera:
Delphacidae such as *Laodelphax striatellus, Nilaparvata lugens* and *Sogatella furcifera*. Deltocephalidae such as *Nephotettix cincticeps* and *Nephotettix virescens*, Aphididae, Pentatomidae, Aleyrodidae, Coccidae. Tingidae. Psyllidae, etc Lepidoptera:
Pyralidae such as *Chilo suppressalis, Cnaphalocrocis medinalis, Ostrinia mtbilalis, Parapediasia teterrella, Notarcha derogata* and *Plodia interputictella*, Noctuidae such as *Spodoptera litura, Spodoptera exigua, Spodoptera littoralis, Pseudaletia separata, Mamestra brassicae, Agrotis ipsilon. Trichoplusia spp., Heliothis spp. Helicoverpa spp.* and *Earias spp*, Pieridae such as *Pieris rapae crucivora*, Tortricidae such as *Adoxophyes spp.*, Carposinidae such as *Grapholita rnolesta, Cydia pomonella* and *Carposina niponensis*, Lyonetiidae such as *Lyonetia spp.*, Lymantruidae such as *Lymantria spp.* and *Euproctis spp.*, Yponomeutidae such as *Plutella xylostella*. Gelechiidae such as *Pectinophora gossypiella*, Arctiidae such as *Hyphantria cunea*, Tineidae such as *Tinea translucens* and *Tineola bisselliella*, etc.

Diptera:
Culex such as *Culex pipienspallens* and *Cules triaeniorhynchus*, Aedes such as *Aedes aegypti* and *Aedes albopictus*, Anopheles such as *Anophelinae sinensis*, Chironomidae, Muscidae such as *Musca domestica* and *Muscina stabidans*, Calliphoridae, Sarcophagidae. *Fannia canicularis*. Anthomyiidae such as *Hylemya Platura* and *Hyle,nya antiqua*. Trypetidae, Drosophilidae. Psychodidae, Tabanidae. Simuliidae, Stomoxyinae. Agromyzidae, etc Coleoptera:
Diabrotica such as *Diabrotica virgifera* and *Diabrotica urrdecipunctata*, Scarabaeidae such as *Anomala cuprea* and *Anomala rufocttprea*, Curculioniidae such as *Sitophilas oryzae, Lissorhoptrus oryzophilus* and *Callosobnichus chinensis*, Tenebrionidae such as *Tenebrio molitor* and *Tribolium castaneum*, Chrysomelidae such as *Phyllotreta striolata* and *Aulacophora femoralis*, Anobiidae, *Epilachtia spp.* such as *Epilachina vigintioctopunctata*, Lyctidae, Bostrychidae, Cerambycidae, Paedenisfuscipes, etc.

Dictyoptera:
*Blattella germanica, Periplaneta fuliginosa, Peroplaneta americana, Periplaneta bninnea, Blatta orientalis*, etc.

Thysanoptera:
*Thrips palmi, Thrips hawaiiensis*, etc.

Hymenoptera:
Formicidae, Vespidae, Bethylidae, Tenthredinidae such as *Athalia rosae japonensis*, etc.

Orthoptera:
Gryllotalpidae, Acrididae, etc. Siphonaptera: *Purex irritans* etc.

Anoplura:
*Pediculus humanus capitis, Phthirus pubis*, etc.

Isoptera (terrnites):
*Reticulitermes speratus, Coptotermes formosanus*, etc.

Acarina:
Plant parasitic Tetranychidae such as *Tetranychus uriticae, Panonychus citri, Tetranychus cinnabarinus* and *Panonychus ulmi*, Eriophyidae such as *Acaphylla theae*, and *Aculops pelekassi*, animal parasitic Ixodidae such as *Boophilus microphus*, house dust mites, etc, The present compounds are also effective for the control of various noxious insects, mites and ticks having resistance to conventional insecticides and acaricides.

When the present compounds are used as active ingredients of insecticidal/acaricidal agents, they may be used as such without any addition of other ingredients.

The present compounds are, however, usually formulated into, for example, oil sprays, emulsifiable concentrates, wettable powders, flowable concentrates, granules, dusts, aerosols, fumigants (foggings) and poison baits. These formulations are usually prepared by mixing the present compounds with solid carriers, liquid carriers, gaseous carriers or baits, and if necessary, adding surfactants and other auxiliaries used for formulation.

Each of the formulations usually contains at least one of the present compounds as an active ingredient in an amount of 0.01% to 95% by weight.

Examples of the solid carrier to be used for formulation may include fine powder or granules of clay materials such as kaolin clay, diatomaceous earth, synthetic hydrated silicon oxide, bentonite, Fubasami clay and acid clay; various kinds of talc, ceramics and other inorganic minerals such as sericite, quartz, sulfur, active carbon, calcium carbonate and hydrated silica; and chemical fertilizers such as ammonium sulfate, ammonium phosphate, ammonium nitrate, urea and ammonium chloride.

Examples of the liquid carrier may include water, alcohols such as methanol and ethanol; ketones such as acetone and methyl ethyl ketone; aromatic hydrocarbons such as benzene, toluene, xylene, ethylbenzene and methylnaphthalene; aliphatic hydrocarbons such as hexane, cyclohexane, kerosine and gas oil; esters such as ethyl acetate and butyl acetate; nitriles such as acetonitrile and isobutyronitrile; ethers such as diisopropyl ether and dioxane; acld amides such as N,N-dimethylformamide and N,N-dimethylacetamide; halogenated hydrocarbons such as dichloromethane, trichloroethane and carbon tetrachloride; dimethyl sulfoxide; and vegetable oils such as soybean oil and cottonseed oil.

Examples of the gaseous carrier or propellant may include flon gas, butane gas, LPG (liquefied petroleum gas), dimethy ether and carbon dioxide.

Examples of the surfactant may include alkyl sulfates, alkyl sulfonates, alkyl arylsulfonates, alkyl aryl ethers and their polyoxyethylene derivatives, polyethyleneglycol ethers, polyhydric alcohol esters and sugar alcohol derivatives.

Examples of the auxiliaries used for formulation, such as fixing agents or dispersing agents, may include casein, gelatin, polysaccharides such as starch, gum arabic, ellulose derivatives and alginic acid, lignin derivatives, bentonite, sugars, and synthetic water-soluble polymers such as polyvinyl alcohol, polyvinyl pyrrolidone and polyacrylic acid.

Examples of the stabilizer may include PAP (isopropyl acid phosphate), BHT (2,6-ditert-butyl-4-methylphenol), BHA (mixtures of 2-tert-butyl-4-methoxyphenol and 3-tertbutyl-4-methoxyphenol), vegetable oils, mineral oils, surfactants, fatty acids and their esters. Examples of the base material to be used in the poison baits may include bait materials such as grain powder, vegetable oils, sugars and crystalline cellulose, antioxidants such as dibutylhydroxytoluene and nordihydroguaiaretic acid; preservatives such as dehydroacetic acid, substances for preventing erroneous eating, such as red pepper powder, attractant flavors such as cheese flavor or onion flavor.

The formulations thus obtained are used as such or after diluted with water. The formulations may also be used in combination with other insecticides, nematocides, acaricides, bactericides, fungicides, herbicides, plant growth regulators, synergists, fertilizers, soil conditioners and/or animal feed under non-mixing conditions or pre-mixina conditions.

Examples of the insecticide, nematocide and/or acaricide which can be used may include organophosphorus compounds such as Fenitrothion [O,O-dimethyl O-(3-methyl-4-nitrophenyl)phosphorothioate], Fenthion [O,O-dimethyl O-(3-methyl-4-(methyl-thio)phenyl)phophorothioate], Diazinon [O,O-diethyl-0-2-isopropyl-6-methylpyrirnldin-4-ylphosphorothioate], Chlorpyriphos [O,O-diethyl-O-3,5,6-trichloro-2-pyridylphosphorothioate], Acephate [O,S-dimethylacetylphosphoramidothioate], Methidathion [S-2,3-di-hydro-5-methoxy-2-oxo-1,3,4-thiadiazol-3-ylmethyl O,O-dimethylphos phorodithioate], Disulfoton [O,O-diethyl S-2-ethylthioethylphosphorothioate], DDVP [2,2-dichlorovinyl imethylphosphate], Sulprofos [O-ethyl O-4-(methylthio)phenyl S-propyl phosphorodihioate], Cyanophos [O-4-cyanophenyl O,O-dimethylphosphorothioate], Dioxabenzofos 2-methoxy-4H-1,3,2-benzodioxaphosphinine-2-sulfide], Dimethoate [O,O-dimethyl-S-N-methylcarbamoylmethyl) dithiophosphate], Phenthoate [ethyl 2dimethoxyphosphinothioylthio(phenyl) acetate], Malathion [diethyl(dimethoxyphosphinothioylthio) succinate], Trichlorfon [dimethyl 2,2,2-trichloro-1hydroxyethylphosphonate],azinphos-methyl S-3,4-dihydro-4-oxo-1,2,3-benzotriazin-3-ylmethyl O,O-dimethyl phos phorodithioate], monocrotophos [dimethyl (E)-1-methyl-2(methylcarbamoyl)vinylphosphate], Ethion O,O, O',O'-tetraethyl S,S'-methylenebis(phosphorodithioate)] and Profenofos [O-4-bromo-2-chlorophenyl O-ethyl S-propyl phosphorothioate]; carbamate compounds such sBPMC [2-sec-butylphenylmethylcarbamate], Benfuracarb [ethyl N-[2,3 -dihydro-2,2-dimethylbenzofuran-7-yloxycarbonyl (methyl)aminothio]-N-isopropyl-β-alaninate], Prooxur [2-isopropoxyphenyl N-methylcarbamate], Carbosulfan [2,3-dihydro-2,2-diethyl-7benzo[b]fulranyl N-dibutylantinothio-N-methylcarbamate). Carbaril [1-naphthylmethylcarbamate], Methomyl [S-methyl-N-[(methylcarbamoyl)oxy]thioacetimidate], thiofencarb [2-(ethylthiomethyl)phenylmethylcarbamate], Aldicarb [2-methyl-2-(methylthio)propanaidehyde O-methylcarbamoyloxime]. Oxamyl [N,N-dimethyl-2methylcarbamoyloxyimino-2-(methylthio)acetamide], Fenothiocarb [S-(4-phenoxybutyl)-N, Ndimethylthiocarbamate], Thiodicarb [3,7,9,13-tetramethyl-5,11 -dioxa-2,8,14-trithia-4,7,9,12-tetraazapentadeca-3,12-diene-6,10-dione] and Alanylcarb [ethyl (Z)-N-benzyl-N-{[methyl(1-methylthioethy] idenearninooxycarbonyl)arnino]thio}-β-alaninate]; pyrethroid compounds such as Etofenprox [2-(4-ethoxyphenyl)-2-methylpropyl-3-phenoxybenzylether], Fenvalerate [(RS)-α-cyano-3-phenoxybenzyl (RS)-2-(4-chlorophenyl)-3-methylbutyrate], Esfenvalerate [(S)-α-cyano-3-phenoxybenzyl (S)-2-(4-chlorophenyl)-3-methylbutyrate], Fenpropathrin [(RS)-α-cyano-3-phenoxybenzyl 2,2,3,3tetramethy]cyclopropanecarboxylate], Cypermethrin [(RS)-α-cyano-3-phenoxybenzyl (1RS,3RS)-3-(2,2-dichlorovinyl)-2,2-dimethylcyclopropanecarboxylate], Permethrin [3-phenoxybenzyl (1RS, 3RS)-3-(2,2-dichlorovinyl)-2,2-dimethylcyclopropanecarboxylate], Cyhalothrin [(RS)-α-cyano-3-phenoxybenzyl (Z)-(1RS)-cis-3-(2-chloro-3,3,3-trifluoro prop-1-enyl)-2,2-dimethylcyclopropanecarboxylate], Deltamethrin [(S)-α-cyano-m-phenoxybenzyl (1R,3 R)-3-(2,2-dibromovinyl)-2.2-dimethylcyclopropanecarboxylate], Cycloprothrin [(RS) -α-cyano-3-phenoxybenzyl (RS)-2,2-dichloro-1-(4-ethoxyphenyl)cyclo propanecarboxylate], Fluvalinate [α-cyano-3-phenoxybenzyl N-(2chloro-α, α, α-trifluoro-p-tolyl)-D-valinate], Bifenthrin [2-methylbiphenyl-3-ylmethyl) (Z)-(1RS)-cis-3-(2-chloro-3,3,3-trifluoroprop-1-enyl)-2,2-dimethylcyclopropanecarboxylate], Acrinathrin [(S)-α-cyano-3-phenoxybenzyl (Z)-(1R,3S)-2,2-dimethyl-3-[2-(2,2,2-trifluoro-1-trifluoro-1-trifluoromethylethoxycabonyl)vinyl] cyclopropanrcarboxylate], 2-methyl-2-(4-bromodifluoromethoxyphenyl)propyl (3-phenoxybenzyl) ether, Traromethrin [(S)-α-cyano3-phenoxyl-benzyl (1R, 3R)-3-[(1'RS)(1',1',2',2'-tetrabromoethyl)]-2,2-dimethylcyclopropanecarboxylate] and Silafluofen [4-ethoxylphenyl [3-(4-fluoro-3-phenoxyphenyl)propyl] dimethylsilane]; thiadiazine derivatives such as Buprofezin [2-tertbutylinmnoo-3-isopropyl-5-phenyl-1,3,5-thiadiazirn-4-one]; nitroimidazolidine derivatives such as Imidacloprid [1-(6-chloro-3-pyridylmethyl)-N-nitroimidazolidin-2-ylidenamine]Nereistoxin derivatives such as Cartap [S,S'-(2dimethylaminotrimethylene)bis(thiocarbamate)], Thiocyclam [N,N-dimethyl-1,2,3trithian-5-ylamine] and Bensultap [S.S'-2-dimethylamino-trimethylene di(benzenethlosulfonate)]; N-cyanoamidine derivatives such as acetamiprid [N-cyano-N'-methyl-N'-(6-chloro-3-pyridylmethyl)acetamidine]; chlorinated hydrocarbon compounds such as Endosulfan [6,7,8,9,10,10-hexachloro-1,5,5a,6,9,9a-hexahydro-6,9-methano-2,4,3-benzodioxathiepinoxide], γ-BHC [1,2,3,4,5,6-hexachlorocyclohexane] and Kelthane [1,1-bis(chlorophenyl)-2,2,2-trichloroethanol]; benzoylphenylurea compounds such as Chlorfluazuron [1-(3,5-dichloro-4-(3-chloro-5-trifluoromethyl-pyridin-2-yloxy)phenyl)-3-(2,6-difluorobenzoyl)urea], Teflubenzuron [1-(3,5-dichloro-2,4-difluorophenyl)-3-(2,6-difluorobenzoyl)urea] and Fulphenoxron [1-(4-(2-chloro-4-trifluoromethylphenoxy)-2fluoropheny])-3-(2,6-difluorobenzoyl)urea];formamidine derivatives such as Amitraz [N,N'-[(methylimino)dimethylidine]-di-2,4-xylidine] and Chlordimeform [N'-(4-chlor0-2-methylphenyl)-N,N-dimethylmethanimidamide]; thiourea derivatives such as Diafenthiuron [N-(2,6-diisopropyl-4-phenoxyphenyl)-N'-tert-butylcarbodiimide]; Bromopropylate [isopropyl 4,4'-dibromobenzylate], Tetradifon [4-chlorophenyl 2,4,5-trichlorophenylsulfone], Quinomethionate [S,S(6methylquinoxaline-2,3-diyl) dithiocarbonate], Propargite [2-(4-tert-butylphenoxy) cyclohexyl, prop-2-yl sulfite], Fenbutatinoxide [bis[tris(2-methyl-2-phenylpropyl)tin]oxide], Hexythiazox [(4RS, 5RS)-5-(4-chloro-phenyl)-N-chlorohexyl-4-methyl-2-oxo-1,3-thiazolidine-3-carboxamide], Chlofentezine [3,6-bis(2-chlorophenyl)-1,2,4,5-tetrazine], Pyridaben [2-tert-butyl-5-(4-tert-butylbenzylthio)-4-chloropyrfidazin3(2H)-one], Fenpyroximate [tert-butyl(E)-4-[(1,3-dimethyl-5-phenoxypyrazol-4-yl)methylenearminooxymethyl]benzoate], Tebfenpyrad [N-4-tert-butyl-benzyl)-4-chlor0-3-ethyl-1-methyl-5-pyrazolecarboxamide], polynactin complexes including tetranactin, dinactin and trinactin; Milbemectin, Avennectin, Ivermectin, Azadilactin [AZAD], Pyrimidifen [5-chloro-N-[2-{4-(2-ethoxyethyl)-2,3-dimethylphenoxy}ethyl]-6-ethylpyrimid Chlorfenapyl [4-brom0-2-(4-chlorophenyl)-1-ethoxymethyl-5-trifluoromethylpyrrole-3-carbonitrile], and Tebfenozide [N-tert-butyl-N'-(4-ethylbenzoyl)-3,5-diniethylbenzohydrazide].

When the present compounds are used as active ingredients of insecticidallacaricidal agents for agriculture use, the application amount thereof is usually in the range of 0.1 to 100 g per 10 ares. In the case of emulsifiable concentrates, wettable powders and flowable concentrates, which are used after diluted with water, the application concentration thereof is usually in the range of 1 to 10,000 ppm. In the case of granules and dusts, they are applied as such without any dilution.

When the present compounds are used as active ingredients of insecticidal/acaricidal agents for household use, they are formulated into formulations such as emulsifiable concentrates, wettable powders and flowable concentrates, which are applied after diluted with water to a typical concentration of 0.1 to 500 ppm; or they are formulated into, for example, oil sprays, aerosols, fumigants and poisonous baits, which are applied as such without any dilution.

The present compounds and methods are disclosed in Japanese Application 08/015224, filed Jan. 31, 1996, the complete disclosure of which is incorporated herein by reference.

EXAMPLES

The following Procduction Examples, Formulation Examples and Test Examples of the present invention further illustrate the present invention in detail but are not to be construed to limit the scope thereof.

Firstly, Production Examples of the present compound will be described.

Production Example 1

Production of compound (I) by Process C.

4-(3-(4-Chlorophenoxy)propyloxy)-3,5-dichlorophenoxyacetaldehyde diethylacetal (manufactured in Production Example 1 of intermediate described hereinafter) (1.6 g) was added dropwise to a mixed solution of 1 ml of hydrochloric acid and 9 ml of acetic acid with stirring at room temperature. After stirring at room temperature for 30 minutes, the reaction solution was poured into iced water and extracted twice with 100 ml of diethyl ether. The ether layers were combined. washed with water, washed twice with aqueous 5% sodium hydrogencarbonate, washed with water, dried over anhydrous magnesium sulfate and then concentrated to obtain 0.8 g of 4-(3-(4-chlorophenoxy) propyloxy)-3,5-dichlorophenoxyacetaldehyde as a crude product.

This compound (0.8 g) was dissolved in 5 ml of diethylene glycol dimethyl ether and 0.59 g of triphenylphosphine was added. With stirring the reaction solution at 160° C., a solution prepared by dissolving 0.47 g of a sodium chlorodifluoroacetate in 10 mnl of diethylene glycol dimethyl ether (heated to 70° C.) was added dropwise. After stirring at 160° C. for 1.5 hours, the reaction solution was returned to room temperature, poured into iced water and then extracted twice with 100 ml of diethyl ether. The ether layers were combined, washed with water, dried over anhydrous magnesium sulfate and then concentrated to obtain a crude product. This crude product was subjected to silica gel chromatography to obtain 0.3 g of 4-(3-(4-chlorophenoxy) propyloxy)-3,5-dichloro-1-(3,3difluoro-2-propenyloxy) benzene.

Yield 20% $n_D^{25.5}$ 1.5490

Production Example 2

Production of Compound (5) by Process C.

4-(4-(4-(Trifluoromethyl)phenoxy)butyloxy)-3,5-dichlorophenoxyacetaldehyde diethylacetal (manufactured in Production Example 1 of intermediate described hereinafter) (1.0 g) was added dropwise to a mixed solution of 1 ml of hydrochloric acid and 9 ml of acetic acid with stirring at room temperature. After stirring at room temperature for 20 minutes, the reaction solution was poured into iced water and extracted twice with 100 ml of diethyl ether. The ether layers were combined, washed with water, washed twice with aqueous 5% sodium hydrogencarbonate, washed with water, dried over anhydrous magnesium sulfate and then concentrated to obtain 0.7 g of 4-(4-(4-(trifluoromethyl)phenoxy)butyloxy)-3,5-dichlorophenoxyacetaldehyde as a crude product.

Thiscompound (0.7 g) was dissolved in 20 ml of dichioromethane and 1.1 g of tribromofluoromethane, 1.0 g of triphenylphosphine and 0.26 g of zinc were added, followed by stirring at room temperature for 12 hours. The reaction solution was concentrated and the resulting crude product was subjected to silica gel chromatography to obtain 0.34 g of 4-(4-(4-(trifluoromethyl)phenoxy)butyloxy)-3,5-dichloro-1-(3-bromo-3-fluoro-2-propenyloxy)benzene.

Yield 33% $n_D^{23.0}$ 1.5339

Production Example 3

Production of Compound (6) by Process C.

4-(4-(4-(Trifluoromethyl)phenoxy)butyloxy)-3,5-dichlorophenoxyacetaldehyde (0.7 g) obtained by the same operation as that of the first half part of Production Example 2 and 0.8 g of zinc were added to 20 ml of tetrahydrofuran with stirring 4 5° C. To this solution was added 0.8 g of (dichlorofluoromethyl)tris(dimethylamino)phosphonium chloride [this compound was prepared as follows: Trichlorofluoromethane (2.5 g) was dissolved in 20 ml of diethyl ether and a solution prepared by dissolving 2.2 g of tris (dimethylamino)phosphine in 10 ml of diethyl ether was added dropwise with stirring at 0° C. After stirring at 0° C. for 2 hours, the reaction temperature was returned to room temperature and the solution was further stirred for 20 hours. The deposited crystal was collected by filtration to obtain 3.0 g of (dichlorofluoromethyl)tris(dimethylamino) phosphonium chloricle], followed by stirring at 60° C. for 5 hours. The reaction solution was filtered and the filtrate was concentrated. The resulting crude product was subjected to silica gel chromatography to obtain 0.24 g of 4-(4-(4-(trifluoromethyl)phenoxy)butyloxy)-3, 5 -dichioro-1-(3 -chloro-3 - fluoro-2-propenyloxy)benzene.

Yield 25% $n_D^{21.5}$ 1.5209

Hereinafter, some embodiments of the present compound will be described together with their compound numbers.

(1) 4-(3-(4-Chlorophenoxy)propyloxy)-3,5-dichloro-1-(3,3 -difluoro-2-propenyloxy)benzene $n_D^{25.5}$ 1.5490

(2) 4-(3-(4-(Trifluoromethyl)phenoxy)propyloxy)-3-methyl-5-ethyl-1-(3,3-difluoro-2-propenyloxy)benzene $n_D^{25.5}$ 1.4955

(3) 4-(3-(4-(Trifluoromethyl)phenoxy)propyloxy)-3,5-dichloro-1-(3,3-difluoro-2-propenyloxy)benzene $n_D^{25.5}$ 1.5082

(4) 4-(3-Chlorophenoxy)-2-chloro-1-(3,3-difluoro-2-propenyloxy)benzene $n_D^{22.5}$ 1.5643

(5) 4-(4-(4-(Trifluoromethyl)phenoxy)butyloxy)-3,5-dichloro-1-(3-bromo-3-fluoro-2-propenyloxy)benzene $n_D^{23.0}$ 1.5339

(6) 4-(4-(4-(Trifluoromethyl)phenoxy)butyloxy)-3,5-dichloro-1-(3-chloro-3-fluoro-2-propenyloxy)benzene $n_D^{21.5}$ 1.5209

(7) 4-(4-(4-(Chlorophenoxy)butyloxy)-3,5-dichloro-1-(3-chloro-3-fluoro-2-propenyloxy)benze $n_D^{17.0}$ 1.5654

(8) 4-(4-(4-(Chlorophenoxy)butyloxy)-3,5-dichloro-1-(3-bromo-3-fluoro-2-propenyloxy)benzene $n_D^{17.0}$ 1.5731

(9) 4-(4-(4-(Bromophenoxy)butyloxy)-3,5-dichloro-1-(3-chloro-3-fluoro-2-propenyloxy)benzene

(10) 4-(4-(4-(Bromophenoxy)butyloxy)-3,5-dichloro-1-(3-bromo-3-fluoro-2-propenyloxy)benzene

(11) 4-(4-(4-(Isopropoxyphenoxy)butyloxy)-3,5-dichloro-1-(3-chloro-3-fluoro-2-propenyloxy)benzene

(12) 4-(4-(4-(Isopropoxyphenoxy)butyloxy)-3,5-dichloro-1-(3-bromo-3-fluoro-2-propenyloxy)benzene

(13) 4-(4-(4-(Trifluoromethoxy)phenoxy)butyloxy)-3,5-dichloro-1-(3-chloro-3-fluoro-2-propenyloxy)benzene

(14) 4-(4-(4-(Trifluoromethoxy)phenoxy)butyloxy)-3,5-dichloro-1-(3-bromo-3-fluoro-2-propenyloxy)benzene

(15) 4-(4-(4-(Chlorophenoxy)butyloxy)-3,5-diethyl-1-(3-chloro-3-fluoro-2-propenyloxy)benzene

(16) 4-(4-(4-(Chlorophenoxy)butyloxy)-3,5-diethyl-1-(3-bromo-3-fluoro-2-propenyloxy)benzene

(17) 4-(4-(4-(Trifluoromethyl)phenoxy)butyloxy)-3,5-diethyl-1-(3-chloro-3-fluoro-2-propenyloxy)benzene

(18) 4-(4-(4-(Trifluoromethyl)phenoxy)butyloxy)-3,5-diethyl-1-(3-bromo-3-fluoro-2-propenyloxy)benzene

(19) 4-(4-(4-(Isopropoxyphenoxy)butyloxy)-3,5-diethyl-1-(3-chloro-3-fluoro-2-propenyloxy)benzene

(20) 4-(4-(4-(Isopropoxyphenoxy)butyloxy)-3,5-diethyl-1-(3-bromo-3-fluoro-2-propenyloxy)benzene

(21) 4-(4-(4-(Trifluoromethyl)phenoxy)butyloxy)-3-chioro-5-methyl-1-(3-chloro-3-fluoro-2-propenyloxy)benzene

(22) 4-(4-(4-(Trifluoromethyl)phenoxy)butyloxy)-3-chloro-5-methyl-1-(3-bromo-3-fluoro-2-propenyloxy)benzene

(23) 4-(4-(4-(Trifluoromethyl)phenoxy)butyloxy)-3-ethyl-5-methyl-1-(3-chloro-3-fluoro-2-propenyloxy)benzene

(24) 4-(4-(4-(Trifluoromethyl)phenoxy)butyloxy)-3-ethyl-5-methyl-1-(3-bromo-3-fluoro-2-propenyloxy)benzene

(25) 4-(4-(4-Isopropoxyphenoxy)butyloxy)-3-ethyl-5-methyl-1-(3-chloro-3-fluoro-2-propenyloxy)benzene

(26) 4-(4-(4-Isopropoxyphenoxy)butyloxy)-3-ethyl-5-methyl-1-(3-bromo-3-fluoro-2-propenyloxy)benzene

(27) 4-(3-(4-Chlorophenoxy)propyloxy)-3,5-dichloro-1-(3-chloro-3-fluoro-2-propenyloxy)benzene

(28) 4-(3-(4-Chlorophenoxy)propyloxy)-3,5-dichloro-1-(3-bromo-3-fluoro-2-propenyloxy)benzene

(29) 4-(3-(4-Bromophenoxy)propyloxy)-3,5-dichloro-1-(3-chloro-3-fluoro-2-propenyloxy)benzene

(30) 4-(3-(4-Bromophenoxy)propyloxy)-3,5 -dichloro-1-(3-bromo-3-fluoro-2-propenyloxy)benzene

(31) 4-(3-(4-Isopropoxyphenoxy)propyloxy)-3,5-dichloro-1-(3-chloro-3-fluoro-2-propenyloxy)benzene

(32) 4-(3-(4-Isopropoxyphenoxy)propyloxy)-3,5-dichloro-1-(3-bromo-3-fluoro-2-propenyloxy)benzene

(33) 4-(3-(4-(Trifluoromethoxy)phenoxy)propyloxy)-3,5-dichloro-1-(3-chloro-3-fluoro-2-propenyloxy)benzene

(34) 4-(3-(4-(Trifluoromethoxy)phenoxy)propyloxy)-3,5-dichloro-1-(3-bromo-3-fluoro-2-propenyloxy)benzene

(35) 4-(3-(4-Chlorophenoxy)propyloxy)-3,5-diethyl-1-(3-chloro-3-fluoro-2-propenyloxy)benzene

(36) 4-(3-(4-Chlorophenoxy)propyloxy)-3,5-diethyl-1-(3-bromo-3-fluoro-2-propenyloxy)benzene

(37) 4-(3-(5-(Trifluoromethyl)-2-pyridyloxy)propyloxy)-3,5-dichloro-1-(3-chloro-3-fluoro-2-propenyloxy)benzene $n_D^{17.5}$ 1.5211

(38) 4-(3-(5-(Trifluoromethyl)-2-pyridyloxy)propyloxy)-3,5-dichloro-1-(3-bromo-3fluoro-2-propenyloxy)benzene $n_D^{17.5}$ 1.5319

(39) 4-(3-(4-(Trifluoromethyl)benzoylamino)propyloxy)-3,5-dichloro-1-(3-chloro-3fluoro-2-propenyloxy)benzene

(40) 4-(3-(4-(Trifluoromethyl)benzoylamino)propyloxy)-3,5-dichloro-1-(3-bromo-3-fluoro-2-propenyloxy)benzene

(41) 4-(3-Chloro-5-(trifluoromethyl)-2-pyridyloxy)-3,5 -dichloro-1-(3-chloro-3-fluoro-2-propenyloxy)benzene

(42) 4-(3-Chloro-5-(trifluoromethyl)-2-pyridyloxy)-3,5-dichloro-1-(3-bromo-3-fluoro-2-propenyloxy)benzene

(43) 4-(3,5-Bis(trifluoromethyl)-2-pyridyloxy)-3,5-dichloro-1-(3-chloro-3-fluoro-2-propenyloxy)benzene

(44) 4-(3,5-Bis(trifluoromethyl)-2-pyridyloxy)-3,5-dichloro-1-(3-bromo-3-fluoro-2-propenyloxy)benzene

(45) 4-(5-(Ttrifluoromethyl)-2-pyridyloxy)-3,5-dichloro-1-(3-chloro-3-fluoro-2-propenyloxy)benzene

(46) 4-(5-(Ttrifluoromethyl)-2-pyridyloxy)-3,5-dichloro-1-(3-bromo-3-fluoro-2-propenyloxy)benzene

(47) 4-(3-(4-(Ttrifluoromethyl)phenoxy)propyloxy)-3,5-dichloro-1-(3-bromo-3-fluoro-2-propenyloxy)benzene

(48) 4-(3-(4-(Ttrifluoromethyl)phenoxy)propyloxy)-3,5-dichloro-1-(3-chloro-3-fluoro-2-propenyloxy)benzene

(49) 4-(3-(4-(Ttrifluoromethyl)phenoxy)propyloxy)-3,5-diethyl-1-(3-bromo-3-fluoro-2-propenyloxy)benzene

(50) 4-(3-(4-(Ttrifluoromethyl)phenoxy)propyloxy)-3-ethyl-5-methyl-1-(3-bromo-3-fluoro-2-propenyloxy) benzene

(51) 4-(3-(4-(Ttrifluoromethyl)phenoxy)propyloxy)-3,5-diethyl-1-(3-chloro-3-fluoro-2-propenyloxy)benzene

(52) 4-(3-(4-(Ttrifluoromethyl)phenoxy)propyloxy)-3-ethyl-5-methyl-1-(3-chloro-3-fluoro-2-propenyloxy) benzene

(53) 4-(4-(4-(Chlorophenoxy)butyloxy)-3-ethyl-5-methyl-1-(3-bromo-3-fluoro-2-propenyloxy)benzene

(54) 4-(4-(4-(Chlorophenoxy)butyloxy)-3-ethyl-5-methyl-1-(3-chloro-3-fluoro-2-propenyloxy)benzene
(55) 4-(3-(5-Trifluoromethyl)-2-pyridyloxy)propyloxy)-3,5-diethyl-(3-bromo-3-fluoro-2-propenyloxy)benzene
(56) 4-(3-(5-Trifluoromethyl)-2-pyridyloxy)propyloxy)-3,5-diethyl-(3-chloro-3-fluoro-2-propenyloxy)benzene
(57) 4-(3-(5-Trifluoromethyl)-2-pyrdyloxy)propyloxy)-3-ethyl-5-methyl-(3-bromo-3-fluoro-2-propenyloxy)benzene
(58) 4-(3-(5-Trifluoromethyl)-2-pyridyloxy)propyloxy)-3-ethyl-5-methyl-(3-chloro-3fluoro-2-propenyloxy)benzene
(59) 4-(4-(4-chlorophenoxy)butyloxy)-3-chloro-5-methyl-1-(3-bromo-3-fluoro-2-propenyloxy)benzene
(60) 4-(4-(4-Chlorophenoxy)butyloxy)-3-chloro-5-methyl-1-(3-chloro-3-fluoro-2-propenyloxy)benzene
(61) 4-(4-(4-Isopropoxyphenoxy)butyloxy)-3-chloro-5-methyl-1-(3-bromo-3-fluoro-2-propenyloxy)benzene
(62) 4-(4-(4-Isopropoxyphenoxy)butyloxy)-3-chloro-5-methyl-1-(3-chloro-3-fluoro-2-propenyloxy)benzene
(63) 4-(3-(4-(Trifluoromethyl)phenoxy)propyloxy)-3-chloro-5-methyl-1-(3-bromo-3-fluoro-2-propenyloxy)benzene
(64) 4-(3-(4-(Trifluoromethyl)phenoxy)propyloxy)-3-chloro-5-methyl-1-(3-chloro-3-fluoro-2-propenyloxy)benzene
(65) 4-(3-(5-(Trifluoromethyl)-2-pyridyloxy)propyloxy)-3-chloro-5-methyl-1-(3-bromo-3-fluoro-2-propenyloxy)benzene
(66) 4-(3-(5-(Trifluoromethyl)-2-pyridyloxy)propyloxy)-3-chloro-5-methyl-1-(3-chloro-3-fluoro-2-propenyloxy)benzene Hereinafter, Production Examples of the intermediate represented by Formula VII will be described.

Production Example 1 of Intermediate

Hydroquinone monobenzyl ether (20 g) and 500 ml of carbon tetrachloride were charged in a reaction vessel, and a solution prepared by dissolving 22.0 g of tert-butyl hypochlorite in 20 ml of carbon tetrachloride was added dropwise, slowly, with stirring under ice cooling. Twenty-four hours after the dropwise addition, the reaction solution was poured into water and the organic layer (carbon tetrachloride layer) was separated. The resultant was washed with water, dried over anhydrous magnesium sulfate and then concentrated to obtain a crude product. This crude product was subjected to silica gel chromatography to obtain 22.8 g of 4-benzyloxy-2,6-dichlorophenol (yield: 85 %).

To a mixture of 5.0 g of 4-benzyloxy-2,6-dichlorophenol, 4.7 g of 1-bromo-3-(4-chlorophenoxy)propane and 30 ml of N,N-dimethylformamide was added 2.7 g of potassium carbonate with stirring at room temperature. After stirring at room temperature for 12 hours, the reaction solution was poured into iced water and extracted twice with 200 ml of diethyl ether. The ether layers were combined, washed with water, dried over anhydrous magnesium sulfate and then concentrated to obtain a crude product. This crude product was subjected to silica gel chromatography to give 6.5 g of 4-benzyloxy-1-(3-(4-chlorophenoxy)propyloxy)-2,6-dichlorobenzene(yield: 85 %).

4-Benzyloxy-1-(3-(4-chlorophenoxy)propyloxy)-2,6-dichlorobenzene (6.5 g) and 200 ml of ethyl acetate were charged in a reaction vessel and air in the reaction vessel was substituted with nitrogen. Then, 0.5 g of 10% palladium-carbon was added and nitrogen in the vessel was substituted with hydrogen, followed by vigorously stirring at room temperature for 8 hours. After hydrogen in the vessel was substituted with nitrogen, the reaction solution was filtered with Celite and the filtrate was concentrated to obtain 5.2 g of 4-(3-(4-chlorophenoxy)propyloxy-3,5-dichiorophenol (yield: 93%).

A mixture of 2.0 g of 4-(3-(4-chlorophenoxy)propyloxy-3,5-dichlorophenol, 1.25 g of bromoacetaldehyde diethylacetal, 0.95 g of potassium carbonate and 15 ml of N,N-dimethylformamide was stirred at 1 00° C. for 8 hours. After the completion of the reaction, the temperature of the reaction solution was returned to room temperature and the solution was poured into iced water. After extracting twice with 200 ml of diethyl ether, the ether layers were combined, washed with water, dried over anhydrous magnesium sulfate and then concentrated to obtain a crude product. This crude product was subjected to silica gel column chromatography to give 2.0 g of 4-(3-(4-chlorophenoxy)propyloxy-3,5-dichlorophenoxyacetaldehyde diethylacetal (yield: 75%). 4-(3-(4chlorophenoxy)propyloxy-3,5-dichlorophenoxyacetaldehyde diethylacetal: $n_D^{23.0}$ 1.5402.

Hereinafter, some embodiments of the intermediate represented by Formula III will be described.
(1) 2,6-Dichloro-4-(3-fluoro-3-chloro-2-propenyloxy)phenol
(2) 2,6-Dichloro-4-(3-fluoro-3-bromo-2-propenyloxy)phenol
(3) 2-Ethyl-6-methyl-4-(3-bromo-3-fluoro-2-propenyloxy)phenol
(4) 2-Ethyl-6-methyl-4-(3-chloro-3-fluoro-2-propenyloxy)phenol
(5) 2,6-Diethyl-4-(3-bromo-3-fluoro-2-propenyloxy)phenol
(6) 2,6-Diethyl-4-(3-chloro-3-fluoro-2-propenyloxy)phenol
(7) 2-Chloro-6-methyl-4-(3-bromo-3-fluoro-2-propenyloxy)phenol
(8) 2-Chloro-6-methyl-4-(3-chloro-3-fluoro-2-propenyloxy)phenol The following are formulation examples in which "parts" are by weight and the present compounds are designated by their compound numbers as described above, Formulation Example 1: Emulsifiable Concentrates Ten parts of each of the present compounds (1) to (66) are dissolved in 35 parts of xylene and 35 parts of N,N-dimethylformamide, to which 14 parts of polyoxyethylene styrylphenyl ether and 6 parts of calcium dodecylbcnzene-sulfonate are added, and each mixture is well stirred to give a 10% emulsifiable concentrate of each compound.

Formulation Example 2: Wettable powders

Twenty parts of each of the present compounds (1) to (66) are added to a mixture of 4 parts of sodium lauryl sulfate, 2 parts of calcium lignin sulfonate, 20 parts of synthetic hydrated silicon oxide fine powder and 54 parts of diatomaceous earth, and each mixture is stirred with a mixer to give a 20% wettable powder of each compound.

Formulation Example 3: Granules

To five parts of each of the present compounds (1) to (66) are added 5 parts of synthetic hydrated silicon oxide fine powder, 5 parts of sodium dodecylbenzene-sulfonate, 30 parts of bentonite and 55 parts of clay, and each mixture is well stirred. A suitable amount of water is then added to each mixture, which is further stirred, granulated with a granulator and then air-dried to give a 5% granule of each compound.

Formulation Example 4: Dusts

One part of each of the present compounds (1) to (66) is dissolved in a suitable amount of acetone, to which 5 parts of synthetic hydrated silicon oxide fine powder, 0,3 part of PAP and 93.7 parts of clay are added, and each mixture is stirred with a mixer. The removal of acetone by evaporation gives a 19% dust of each compound.

Formulation Example 5: Flowables

Twenty parts of each of the present compounds (1) to (66) are mixed with 1.5 parts of sorbitan trioleate and 28.5 parts of an aqueous solution containing 2 parts of polyvinyl alcohol, and each mixture is pulverized into fine particles having a particle size of not more than 3 μm with a sand grinder, to which 40 parts of an aqueous solution containing 0.05 part of xanthan gum and 0.1 part of aluminum magnesium silicate is added and then 10 parts of propylene glycol is added. Each mixture is stirred to give a 20% water-based suspension of each compound.

Formulation Example 6: Oil sprays

First, 0.1 part of each of the present compounds (1) to (66) is dissolved in 5 parts of xylene and 5 parts of trichloroethane. Each solution was then mixed with 89.9 parts of deodorized kerosine to give a 0.1% oil spray of each compound.

Formulation Example 7: Oil-based aerosols

First, 0.1 part of each of the present compounds (1) to (66), 0.2 part of tetramethrin, 0.1 part of d-phenothrin, and 10 parts of trichloroethane are dissolved in 59,6 parts of deodorized kerosine, and the solution is put in an aerosol vessel. The vessel is then equipped with a valve, through which 30 parts of a propellant (liquefied petroleum gas) is charged under increased pressure to give an oil-based aerosol of each compound.

Formulation Example 8: Water-based aerosols

An aerosol vessel is filled with 50 parts of pure water and a mixture of 0.2 part of each of the present compounds (1) to (66), 0.2 part of d-allethrin, 0.2 part of d-phenothrin, 5 parts of xylene, 3.4 parts of deodorized kerosine and I part of an emulsifier [ATMOS 300 (registered trade name by Atlas Chemical Co.)]. The vessel is then quipped with a valve, through which 40 parts of a propellant (liquefied petroleum gas) are charged under increased pressure to give a water-based aerosol of each compound.

Formulation Example 9: Mosquito-coils

First, 0.3 g of each of the present compounds (1) to (66) is mixed with 0.3 g of d-allethrin, and each mixture is dissolved in 20 ml of acetone. The solution is uniformly mixed with 99.4 g of a carrier for mosquito-coils (prepared by mixing Tabu powder, pyrethrum marc powder and wood flour in the ratio of 4:3:3) under stirring, Each mixture is well kneaded with 120 ml of water, molded and dried to give a mosquito-coil of each compound.

Formulation Example 10: Electric mosquito-mats

First, 0.4 g of each of the present compounds (1) to (66), 0.3 parts of d-allethrin and 0.4 g of piperonyl butoxide are dissolved in acetone to have a total volume of 10 ml. Then, 0.5 ml of each solution is uniformly absorbed in a substrate for electric mosquito-mats having a size of 2.5 cm×1.5 cm×0.3 cm (prepared by forming a fibrillated mixture of cotton linter and pulp into a sheet) to give an electric mosquito-mat of each compound.

Formulation Example1 11: Heating smoke formulations

First, 100 mg of each of the present compounds (1) to (66) is dissolved in a suitable amount of acetone. Each solution is absorbed in a porous ceramic plate having a size of 4.0 cm×4.0 cm×1.2 cm to give a heating smoke formulation of each compound.

Formulation Example 12: Poison baits

First, 10 mg of each of the present compounds (1) to (66) is dissolved in 0.5 ml of acetone, andeachsolution is uniformly mixed with 5 g of solid bait powder for animals (Breeding Solid Feed Powder CE-2, trade name by Japan Clea Co., Ltd.). The subsequent removal of acetone by air drying gives a 0.5% poison bait of each compound.

The following test examples demonstrate that the present compounds are useful as active ingredients of insecticidal/ acaricidal agents. In these test examples, the present compounds are designated by their compound numbers as describe above.

Test Example 1: Insecticidal test against *Spodopteru litura*

Two ml of a 200-fold water dilution (500 ppm) of an emulsifiable concentrate of the test compound, which had been obtained according to Formulation Example 1, were absorbed in 13 g of an artificial diet for *Spodoptera litura*, which had been prepared in a polyethylene cup having a diameter of 11 cm. Ten fourth-instar larvae of *Spodopiera litura* were released in the cup. After 6 days, the survival of the larvae was examined to determine the mortality. The test was conducted in duplicate. As a result, it was found that the present compounds (1), (3), (5), (6), (7), (8), (37) and (38) exhibited the mortality of 80% or higher.

Test Example 2: Insecticidal test against *Culex pipiens*

An emulsifiable concentrate of the test compound, which had been obtained according to Formulation Example 1, was diluted with water and 0.7 ml of the diluted solution was added to 100 ml of ion-exchange water, where concentration of the active ingredient was adjusted to 3.5 ppm. 20 finalinstar larvae were liberated thereto, and mortality ratio was observed seven days later. As a result, it was found that the present compounds (1), (6), (37) and (38) exhibited the mortality of 100%.

Test Example 3: Insecticidal test against *Aphis gossypii*

A polyethylene cup having a volume of 90 ml was filled with sandy loam where cucumber seeds (Sagami Hanjiro) were sowed and grown in a greenhouse for 10 days to obtain seedlings at the first leaf stage. 10 Adult *Aphis gossypii* were liberated onto the seedlings. After keeping them at 25° C. and letting them lay eggs for one day, 25 ml of a water dilution (500 ppm) of an emulsifiable concentrate of the test compound, which had been obtained according to Formulation example 1, was sprayed onto the potted seedling. After kept at 25° C. for 6 days, the number of living aphids was counted. As a result, it was found that the present compounds (1) exhibited the mortality of 100%.

Test Example 4: Insecticidal test against *Plutella xylostella*

A two hundred ppm solution of an emulsifiable concentrate of the test compound, which had been obtained according to Formulation Example 1 was prepared with water containing a spreading agent, "Rino" (made by Nihon Noyaku Company Limited) at the rate of 0.1% by volume. A twenty-five ml of the solution was sprayed onto a cabbage plant at 5-leaf stage planted in a not in an amount of 25 ml per pot. After the treated plant was air-dried, 10 third instar-larvae of *Plutella xylostella* were liberated onto the plant. After 4 days, the mortality was determined. As a result, it was found that the present compounds (6), (7), (8), (37) and (38) exhibited the mortality of 100%.

Test Example 5: Insecticidal test against *Heliothis virescens*

3 Grams of an artificial diet in a plastic cup of 30 ml was treated with the water dilution (100 ppm) of an emulsifiable concentrate of the test compound, which had been obtained according to Formulation Example 1, at a volume of 0.2 ml. A second-instar larva of *Heliothis virescens* was released on the diet. After 6 or 7 days, the mortality was determined. The test was conducted with 10 larvae per group. As a result, it was found that the present compound (5) exhibited the mortality of 80% or more.

What is claimed is:

1. A fluoropropene compound of Formula I:

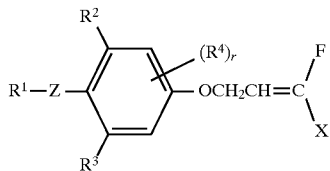

wherein $R^1$ represents;

a $C_1$–$C_{10}$ alkyl group, a $C_1$–$C_5$ haloalkyl group, a $C_2$–$C_{10}$ alkenyl group, a $C_2$–$C_6$ haloalkenyl group, a $C_3$–$C_9$ alkynyl group, a $C_3$–$C_5$ haloalkynyl group, a $C_2$–$C_7$ alkoxyalkyl group or a $C_2$–$C_7$ alkylthioalkyl group;

a $C_3$–$C_6$ cycloalkyl group which may be substituted with a $C_1$–$C_4$ alkyl group a $C_1$–$C_3$ alkoxy group or a $C_1$–$C_3$ haloalkoxy group;

a $C_4$–$C_9$ cycloalkylalkyl group which may be substituted with a $C_1$–$C_4$ alkyl group;

a $C_5$–$C_6$ cycloalkenyl group which may be substituted with a $C_1$–$C_4$ alkyl group;

a $C_6$–$C_8$ cycloalkenylalkyl group which may be substituted with a $C_1$–$C_4$ alkyl group; or $Q_1$, $Q_2$, $Q_3$, $Q_4$, $Q_5$, $Q_6$, $Q_7$, $Q_8$ or $Q_9$ of Formula II:

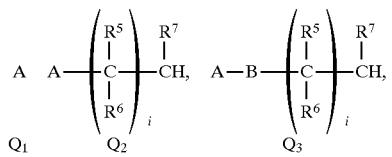

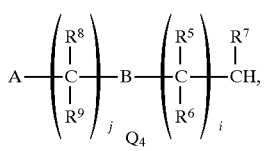

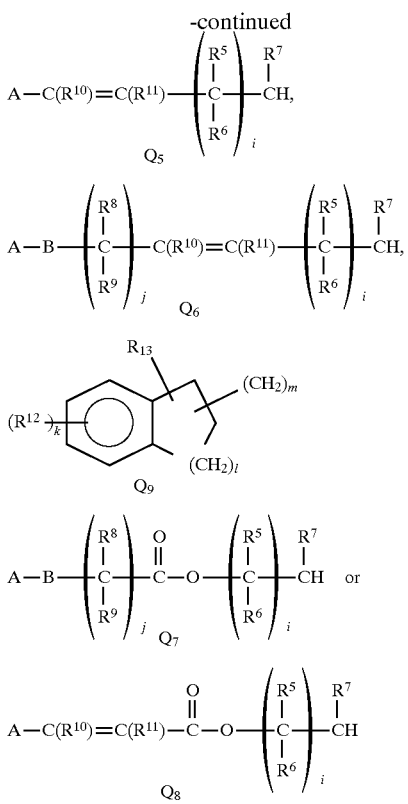

wherein A represents:

a phenyl group which may be substituted with $(R^{16})_q$, a naphthyl group which may be substituted with $(R^{16})_q$ or a heterocyclic group which may be substituted with $(R^{16})_q$, q represents an integer of 0 to 7, and $R^{16}$ represents a halogen atom, a cyano group, a nitro group, a pentafluorosulfanyl group ($F_5S$), a ($C_1$–$C_4$ alkoxy)carbonyl group, a $C_1$–$C_8$ alkyl group, a $C_1$–$C_3$ haloalkyl group, a $C_1$–$C_7$ alkoxy group, a $C_1$–$C_3$ haloalkoxy group, a $C_1$–$C_3$ alkylthio group, a $C_1$–$C_3$ haloalkylthio group, a $C_1$–$C_2$ alkylsulfinyl group, a $C_1$–$C_2$ alkylsulfonyl group, a $C_1$–$C_2$ haloalkylsulfinyl group, a $C_1$–$C_2$ haloalkylsulfonyl group, a $C_3$–$C_6$ alkenyloxy group, a $C_3$–$C_6$ haloalkenyloxy group, a $C_2$–$C_4$ alkenyl group, a $C_2$–$C_4$ haloalkenyl group, a $C_2$–$C_4$ alkynyl group, a $C_2$–$C_4$ haloalkynyl group, a $C_3$–$C_6$ alkynyloxy group, a $C_3$–$C_6$ haloalkynyloxy group, a $C_1$–$C_3$ hydroxyalkyl group, a $C_2$–$C_4$ alkoxyalkyl group, a $C_2$–$C_4$ alkylthioalkyl group, an amino group, a dimethylamino group, an acetamide group, an acetyl group, a haloacetyl group, a fornyl group, a carboxyl group, a ($C_1$–$C_2$ alkyl)aminocarbonyl group, [di($C_1$–$C_2$ alkyl)arnino]carbonyl group, a $C_3$–$C_6$ cycloalkyl group, a $C_5$–$C_6$ cycloalkenyl group, a $C_3$–$C_6$ cycloalkyloxy group or a $C_5$–$C_6$ cycloalkenyloxy group, or a phenyl, phenoxy, benzyl or benzyloxy group all of which may be substituted with at least one substituent group selected from a halogen atom, a $C_1$–$C_4$ alkyl group, a $C_1$–$C_3$ haloalkyl group, a $C_1$–$C_3$ alkoxy group and a $C_1$–$C_3$ haloalkoxy group; or when q is an integer of 2 to 5, two adjacent $R^{16}$ bond together at their terminal ends to form a trimethylene group, a tetramethylene group, a methylenedioxy group which may be substituted with a halogen atom or a $C_1$-$C_3$ alkyl group, or an ethylenedioxy group which may be substituted with a halogen atom or a $C_1$-$C_3$ alkyl group;

B represents an oxygen atom, a $S(O)_n$ group, a $NR^{14}$ group, a $C(=O)G$ group or a $GC(=O)$ group, n represents an integer of 0 to 2, and $R^{14}$ represents a hydrogen atom or a $C_1$-$C_3$ alkyl group;

G represents an oxygen atom or a $NR^{15}$ group, and $R^{15}$ represents a hydrogen atom or a $C_1$-$C_3$ alkyl group;

$R^5$, $R^6$, $R^7$, $R^8$ and $R^9$ independently represent a hydrogen atom, a $C_1$-$C_3$ alkyl group or a trifluoromethyl group;

$R^{10}$ and $R^{11}$ independently represent a hydrogen atom, a $C_1$-$C_3$ alkyl group, a trifluoromethyl group or a halogen atom;

$R^{12}$ represents a halogen atom, a $C_1$-$C_4$ alkyl group, a $C_1$-$C_3$ haloalkyl group, a $C_1$-$C_3$ alkoxy group or a $C_1$-$C_3$ haloalkoxy group;

$R^{13}$ represents a hydrogen atom, a halogen atom or a methyl group;

i represents an integer of 0 to 6;
j represents an integer of 1 to 6;
k represents an integer of 0 to 4;
l represents 1 or 2; and
m represents an integer of 0 to 2;

provided that $R^1$ does not represent a 3,3-dichloro-2-propenyl group, a, 3,3 dibromo-2-propenyl group or a 3-bromo-3-chloro-2-propenyl group;

when A is a naphtyl group which may be substituted with $(R^{16})q$, $R^{16}$ is not a 3,3-dichloro-2-propenyloxy group, a. 3,3-dibromo-2-propenyloxy group or a 3-bromo-3chloro-2-propenyloxy group; and when A is a phenyl group which may be substituted with $(R^{16})q$ for $Q_1$, $Q_3$ and $Q_6$ and $R^{16}$ is a 3,3-dichloro-2-propenyloxy group, a 3,3-dibromo-2-propenyloxy group or a 3-bromo-3-chloro-2-propenyloxy group, q is equal to 1;

Z represents an oxygen atom or a sulfur atom;
X represents a halogen atom;

$R_2$, $R_3$ and $R_4$ independently represent a $C_1$-$C_3$ alkyl group, a $C_1$-$C_3$ haloalkyl group, a halogen atom or a hydrogen atom; and r represents an integer of 0 to 2, provided that $R_2$, $R_3$ and $R_4$ do not simultaneously represent a hydrogen atom.

2. A fluoropropene compound according to claim 1, wherein $R^1$ is $Q_1$ and A is a phenyl group which may be substituted with $(R^{16})q$ or 2-pyridyl group which may be substituted with $(R^{16})q$.

3. A fluoropropene compound according to claim 1, wherein $R^1$ is $Q_2$ and A is a phenyl group which may be substituted with $(R^{16})q$ or 2-pyridyl group which may be substituted with $(R^{16})q$.

4. A fluoropropene compound according to claim 1, wherein $R^1$ is $Q_3$ and A is a phenyl group which may be substituted with $(R^{16})q$ or 2-pyridyl group which may be substituted with $(R^{16})q$.

5. A fluoropropene compound according to claim 1, wherein $R^1$ is $Q_4$, $Q_5$, $Q_6$, $Q_7$, $Q_8$ or $Q_9$ and in which A is a phenyl group which may be substituted with $(R^{16})q$ or 2-pyridyl group which may be substituted with $(R^6)q$.

6. A fluoropropene compound according to claim 2, wherein Z is an oxygen atom, r is 0, and $R^2$ and $R^3$ do not simultaneously represent a hydrogen atom.

7. A fluoropropene compound according to claim 3, wherein Z is an oxygen atom, $R^5$, $R^6$ and $R^7$ represent a hydrogen atom, i is an integer of 0 to 3, r is 0, and $R^2$ and $R^3$ do not simultaneously represent a hydrogen atom.

8. A fluoropropene compound according to claim 4, wherein Z is an oxygen atom, $R^5$, $R^6$ and $R^7$ represent a hydrogen atom, i is an integer of 2 to 4, B is an oxygen atom, a $CO_2$ group or a CONH group, r is 0, and $R^2$ and $R^3$ do not simultaneously represent a hydrogen atom.

9. A fluoropropene compound according to claim 6, wherein X is a chlorine atom or a bromine atom.

10. A fluoropropene compound according to claim 7, wherein X is a chlorine atom or a bromine atom.

11. A fluoropropene compound according to claim 8, wherein X is a chlorine atom or a bromine atom.

12. A fluoropropene compound, which is 4-(4-(4 (Trifluoromethyl)phenoxy)butyloxy)-3,5-dichloro-1-(3-bromo-3-fluoro-2-propenyloxy)benzene, 4(4(4 (Trifluoromethyl)phenoxy)butyloxy)-3,5-dichloro-1-(3-chloro-3-fluoro-2-propbenyloxy)benzene,4-(4-(4-(Chlorophenoxy)butyloxy)-3,5 dichloro-1-(3-chloro-3-fluoro-2-propenyloxy)benzene,4-(4-(4-(Chlorophenoxy)butyloxy)-3,5-dichloro-1-(3-bromo-3-fluoro-2-propenyloxy)benzene,4-(3-(5-(Triflouromethyl)-2-pyridyloxy)propyloxy-3,5-dichloro-1-(3-chloro-3-fluoro-2-propenyloxy)benzene or 4-(3-(5-(Trifluoromethyl)-2-pyridyloxy)propyloxy)-3,5-dichloro-1-(3-bromo-3-fluoro-2-propenyloxy)benzene.

13. An insectcide comprising, as an active ingredient, a fluoropropene compound as defined in any one of the claims 1 and 2–12 and an inert carrier.

14. A method for controlling noxious insects, which comprises applying insecticidally effective amount of a fluoropropene compound as defined in any one of claims 1 and 2–12 to a locus where noxious insects propagate.

15. A method for controlling acarids comprising applying a selected amount of a composition containing a fluoropropene compound as defined in any one of claims 1 and 2–12 as an active ingredient to acarids or to a locus wherein acarids propagate.

16. A compound of Formula III:

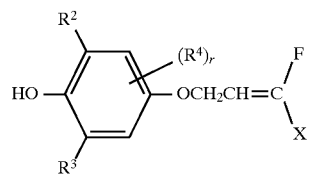

wherein $R^2$, $R^3$, $R^4$, r and X are as defined in claim 1.

* * * * *